US007662960B2

(12) United States Patent
Kahn et al.

(10) Patent No.: US 7,662,960 B2
(45) Date of Patent: Feb. 16, 2010

(54) BETA-STRAND MIMETICS AND METHOD RELATING THERETO

(75) Inventors: Michael Kahn, Kirkland, WA (US); Masakatsu Eguchi, Bellevue, WA (US); Sung Hwan Moon, Kyunggi-do (KR); Jae Uk Chung, Kyunggi-do (KR)

(73) Assignee: Choongwae Pharma Corporation, Seoul (KR)

( * ) Notice: Subject to any disclaimer, the term of this patent is extended or adjusted under 35 U.S.C. 154(b) by 557 days.

(21) Appl. No.: 10/449,822

(22) Filed: May 30, 2003

(65) Prior Publication Data

US 2004/0053331 A1 Mar. 18, 2004

Related U.S. Application Data

(63) Continuation-in-part of application No. 10/013,942, filed on Dec. 11, 2001, now abandoned, which is a continuation-in-part of application No. 09/844,519, filed on Apr. 26, 2001, now abandoned.

(51) Int. Cl.
*C07F 9/02* (2006.01)

(52) U.S. Cl. ...................................................... 544/244

(58) Field of Classification Search ....................... None
See application file for complete search history.

(56) References Cited

U.S. PATENT DOCUMENTS

| | | | | |
|---|---|---|---|---|
| 4,448,960 | A | 5/1984 | Rohr et al. | 544/282 |
| 5,440,013 | A | 8/1995 | Kahn | 530/317 |
| 5,929,237 | A | 7/1999 | Kahn | 544/279 |
| 6,013,458 | A | 1/2000 | Kahn et al. | 435/7.1 |
| 2005/0049234 | A1 * | 3/2005 | Deslongchamps et al. | 514/183 |

FOREIGN PATENT DOCUMENTS

| | | | |
|---|---|---|---|
| EP | 065724 | * | 5/1982 |
| EP | 65724 | B1 | 8/1984 |
| WO | WO 94/03494 | | 2/1994 |
| WO | WO 02/092010 | | 11/2002 |

OTHER PUBLICATIONS

Parsons, J. A. Peptide Hormones. Baltimore: University Park Press, pp. 1-6.*

See Luning, U. "Synthesizing Macrocycles under Thermodynamic Control—Dynamic Combinatorial Libraries and Templates" J. Incl. Phen. Macr. Chem. 2004, 49, 81-84.*

Padwa et al., "Studies Dealing with Thioonium Ion Promoted Mannich Cyclization Reactions" J. Org. Chem. 2000, 65, 235-244.*

Dorwald F. A. Side Reactions in Organic Synthesis, 2005, Wiley: VCH, Weinheim p. IX of Preface.*

Dolle, R.E., "Comprehensive Survey of Combinatorial Library Synthesis: 1999," *Journal of Combinatorial Chemistry 2*(5): 383-433, Sep./Oct. 2000.

Dooley, C.T. et al., "Acetalins: Opioid receptor antagonists determined through the use of synthetic peptide combinatorial libraries," *Proc. Natl. Acad. Sci. USA 90*: 10811-10815, Nov. 1993.

Dooley, C.T. et al., "An All D-Amino Acid Opioid Peptide with Central Analgesic Activity from a Combinatorial Library," *Science 266*: 2019-2022, Dec. 23, 1994.

Dooley and Houghten, "The Use of Positional Scanning Synthetic Peptide Combinatorial Libraries for the Rapid Determination of Opioid Receptor Ligands," *Life Sciences 52*: 1509-1517, 1993.

Eichler, J. et al., "Cyclic Peptide Template Combinatorial Libraries: Synthesis and Identification of Chymotrypsin Inhibitors," *Peptide Research 7*(6): 300-307, 1994.

Gallop, M.A. et al., "Applications of Combinatorial Technologies to Drug Discovery. 1. Background and Peptide Combinatorial Libraries," *Journal of Medicinal Chemistry 37*(9): 1233-1251, 1994.

Graminski and Lerner, "A Rapid Bioassay for Platelet-Derived Growth Factor β-Receptor Tyrosine Kinase Function," *Bio/Technology 12*: 1008-1011, Oct. 1994.

Janda, K.D., "Tagged versus untagged libraries: Methods for the generation and screening of combinatorial chemical libraries," *Proc. Natl. Acad. Sci. USA 91*: 10779-10785, Nov. 1994.

Houghten, R.A. et al., "The Use of Synthetic Peptide Combinatorial Libraries for the Identification of Bioactive Peptides," *BioTechniques 13*(3): 412-421, 1992.

Houghten, R.A. et al., "Generation and use of synthetic peptide combinatorial libraries for basic research and drug discovery," *Nature 354*: 84-86, Nov. 7, 1991.

Lam, K.S. et al., "A new type of synthetic peptide library for identifying ligand-binding activity," *Nature 354*: 82-84, Nov. 7, 1991.

Randolph, J.T. et al., "Major Simplification in Oligosaccharide Syntheses Arising from a Solid-Phase Based Method: An Application to the Synthesis of the Lewis b Antigen," *Journal of the American Chemical Society 117*: 5712-5719, 1995.

(Continued)

*Primary Examiner*—James O Wilson
*Assistant Examiner*—Jeffrey H Murray
(74) *Attorney, Agent, or Firm*—SEED Intellectual Property Law Group PLLC

(57) ABSTRACT

Conformationally constrained compounds of structure:

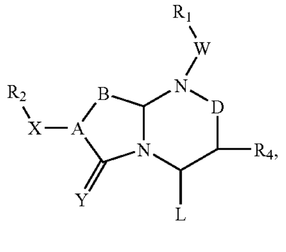

which mimic the secondary structure of β-strand regions of biologically active peptides and proteins are disclosed. Such β-strand mimetic structures have utility over a wide range of fields, including use as diagnostic and therapeutic agents that inhibit protease, kinase and the like. Libraries containing the β-strand mimetic structures of this invention are also disclosed as well as methods for screening the same to identify biologically active members.

4 Claims, 4 Drawing Sheets

OTHER PUBLICATIONS

Tumelty, D. et al., "Immobilised, Activated Peptides as Reagents for Cyclic and Derivatised Peptide Libraries," *J. Chem. Soc., Chem. Commun.* (9): 1067-1068, 1994.

Zaloom and Roberts, "Preparation of Azido Derivatives from Amino Acids and Peptides by Diazo Transfer," *Journal Organic Chemistry 46*: 5173-5176, 1981.

Boer-Terpstra, Tj. et al. "Acetylene Cyclisations of α-acylimmonium ions efficient synthesis of bridgehead nitrogen bicyclic ketones," *Tetrahedron Letters* (11): 939-942, 1977.

Padwa and Waterson, "Studies Dealing with Thionium Ion Promoted Mannich Cyclization Reactions," *Journal of Organic Chemistry 65*: 235-244, 2000.

Wasserman, H.H. et al., "β-Lactams as building blocks in the synthesis of macrocyclic spermine and spermidine alkaloids," *Tetrahedron 58*: 7177-7190, 2002.

Wollweber, H. et al., "Die Kondensation von γ- und δ-Oxo-carbonsäureester mit1 ,2-, 1,3- und 1,4-Alylendiaminen," *Archiv der Pharmazie und Berichte der Deutschen Pharmazeutischen Gesellschaft 304*(10): 774-787, Oct. 1971.

* cited by examiner

BETA-STRAND MIMETICS AND METHOD RELATING THERETO

CROSS-REFERENCE TO RELATED APPLICATION

This application is a continuation-in-part of U.S. patent application Ser. No. 10/013,942 filed on Dec. 11, 2001, now pending, which is a continuation-in-part of U.S. patent application Ser. No. 09/844,519 filed on Apr. 26, 2001, now abandoned. The entire disclosures of these two applications are incorporated herein by reference.

BACKGROUND OF THE INVENTION

1. Field of the Invention

The present invention relates generally to β-strand mimetic structures, to a chemical library relating thereto, and to uses thereof.

2. Description of the Related Art

Random screening of molecules for possible activity as therapeutic agents has occurred for many years and resulted in a number of important drug discoveries. While advances in molecular biology and computational chemistry have led to increased interest in what has been termed "rational drug design," such techniques have not proven as fast or reliable as initially predicted. Thus, in recent years there has been a renewed interest and return to random drug screening. To this end, particular strides having been made in new technologies based on the development of combinatorial chemistry libraries, and the screening of such libraries in search for biologically active members.

In general, combinatorial chemistry libraries are simply a collection of molecules. Such libraries vary by the chemical species within the library, as well as the methods employed to both generate the library members and identify which members interact with biological targets of interest. While this field is still young, methods for generating and screening libraries have already become quite diverse and sophisticated. For example, a recent review of various combinatorial chemical libraries has identified a number of such techniques (Dolle, *J. Com. Chem.,* 2(3): 383-433, 2000), including the use of both tagged and untagged library members (Janda, *Proc. Natl. Acad. Sci. USA* 91: 10779-10785, 1994).

Initially, combinatorial chemistry libraries were generally limited to members of peptide or nucleotide origin. To this end, the techniques of Houghten et al. illustrate an example of what is termed a "dual-defined iterative" method to assemble soluble combinatorial peptide libraries via split synthesis techniques (*Nature* (London) 354: 84-86, 1991*; Biotechniques* 13: 412-421, 1992*; Bioorg. Med. Chem. Lett.* 3: 405-412, 1993). By this technique, soluble peptide libraries containing tens of millions of members have been obtained. Such libraries have been shown to be effective in the identification of opioid peptides, such as methionine- and leucine-enkephalin (Dooley and Houghten, *Life Sci.* 52, 1509-1517, 1993), and a N-acylated peptide library has been used to identify acetalins, which are potent opioid antagonists (Dooley et al., *Proc. Natl. Acad. Sci. USA* 90: 10811-10815, 1993. More recently, an all D-amino acid opioid peptide library has been constructed and screened for analgesic activity against the mu ("μ") opioid receptor (Dooley et al, *Science* 266: 2019-2022, 1994).

While combinatorial libraries containing members of peptide and nucleotide origin are of significant value, there is still a need in the art for libraries containing members of different origin. For example, traditional peptide libraries to a large extent merely vary the amino acid sequence to generate library members. While it is well recognized that the secondary structures of peptides are important to biological activity, such peptide libraries do not impart a constrained secondary structure to its library members.

To this end, some researchers have cyclized peptides with disulfide bridges in an attempt to provide a more constrained secondary structure (Tumelty et al., J. Chem. Soc. 1067-68, 1994; Eichler et al., *Peptide Res.* 7: 300-306, 1994). However, such cyclized peptides are generally still quite flexible and are poorly bioavailable, and thus have met with only limited success.

More recently, non-peptide compounds have been developed which more closely mimic the secondary structure of reverse-turns found in biologically active proteins or peptides. For example, U.S. Pat. No. 5,440,013 to Kahn and published PCT WO94/03494 to Kahn both disclose conformationally constrained, non-peptidic compounds, which mimic the three-dimensional structure of reverse-turns.

While significant advances have been made in the synthesis and identification of conformationally constrained, peptide mimetics, there remains a need in the art for small molecules, which mimic the secondary structure of peptides. There has been also a need in the art for libraries containing such members, as well as techniques for synthesizing and screening the library members against targets of interest, particularly biological targets, to identify bioactive library members. For example U.S. Pat. No. 5,929,237 and its continuation-in-part U.S. Pat. No. 6,013,458 to Kahn also discloses conformationally constrained compounds that mimic the secondary structure of reverse-turn regions of biologically active peptides and proteins.

The present invention also fulfills these needs, and provides further related advantages by providing confomationally constrained compounds which mimic the secondary structure of the β-strand structures of biologically active peptides and proteins.

BRIEF SUMMARY OF THE INVENTION

In brief, the present invention is directed to conformationally constrained compounds that mimic the secondary structure of the β-strand structures of biologically active peptides and proteins. This invention also discloses libraries containing such compounds, as well as the synthesis and screening thereof.

The compounds of the present invention have the following general structure (I):

(I)

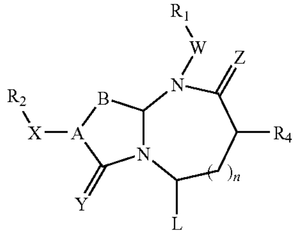

wherein A is —(CH)—, —N— or —$CH_2$—N—, B is —(C═O)— or —$(CH_2)_m$—, W is —(C═O)—, —Y(C═O)—, —NH(C═O)— or nothing, X is —NH—, —NH(C═O)— or nothing, Y is oxygen or sulfur, Z is oxygen or hydrogen, L is hydrogen, $R_5$, —C(O)$NHR_3$ or its equivalents, n=0 or 1 and m=1 or 2; $R_1$, $R_2$, $R_3$, $R_4$ and $R_5$ are the same or different and independently selected from hydrogen, an amino acid side chain moiety or derivative thereof, the remainder of the molecule, a linker and a solid support, and stereoisomers thereof.

In one embodiment of the invention, X is absent, A is —N—, B is —(C=O)—, L is —C(O)NH$R_3$, and other groups are as defined above in structure (I), so that the compounds of the invention have the following structure (I'):

(I')

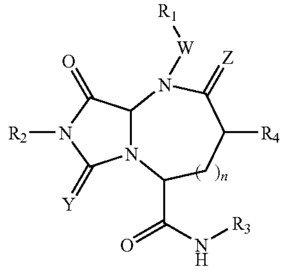

Optionally, W is absent and Z is oxygen.

In one embodiment of the invention, X is absent, A is —N—, B is —$(CH_2)_m$—, L is —C(O)NH$R_3$, and other groups are as defined above in connection with structure (I), so that the compounds of the invention have the following structure (I"):

(I")

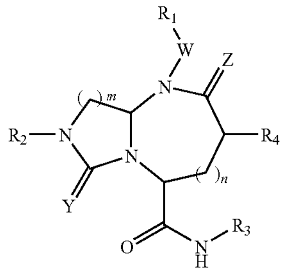

Optionally, W is absent and Z is oxygen.

In one embodiment of the invention, X is —NH—, A is —(CH)—, B is —$(CH_2)_m$—, L is —C(O)NH$R_3$, and the other groups are as defined in connection with structure (I), so that the compounds of the invention have the following structure (I'"):

(I''')

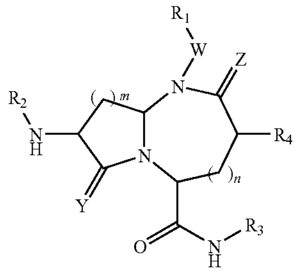

Optionally, when Z is oxygen, then W is absent.

In one embodiment of the invention, A is —$CH_2$—N—, B is —$(CH_2)_m$—, L is —C(O)NH$R_3$, and the other groups are as defined above in connection with structure (I), so that the compounds of the invention have the following structure (I""):

(I'''')

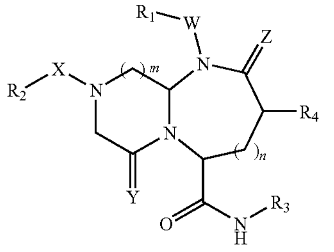

Optionally, Y is oxygen, and/or W is absent, and/or Z is oxygen.

The present invention is also directed to libraries containing compounds of structures (I), (I)'), (I"), (I'"), and (I"") above, as well as methods for synthesizing such libraries and methods for screening the same to identify biologically active compounds. Compositions containing a compound of this invention in combination with a pharmaceutically acceptable carrier or diluent are also disclosed.

These and other aspects of this invention will be apparent upon reference to the following detailed description and the drawings.

DETAILED DESCRIPTION OF THE INVENTION

Figure 1:
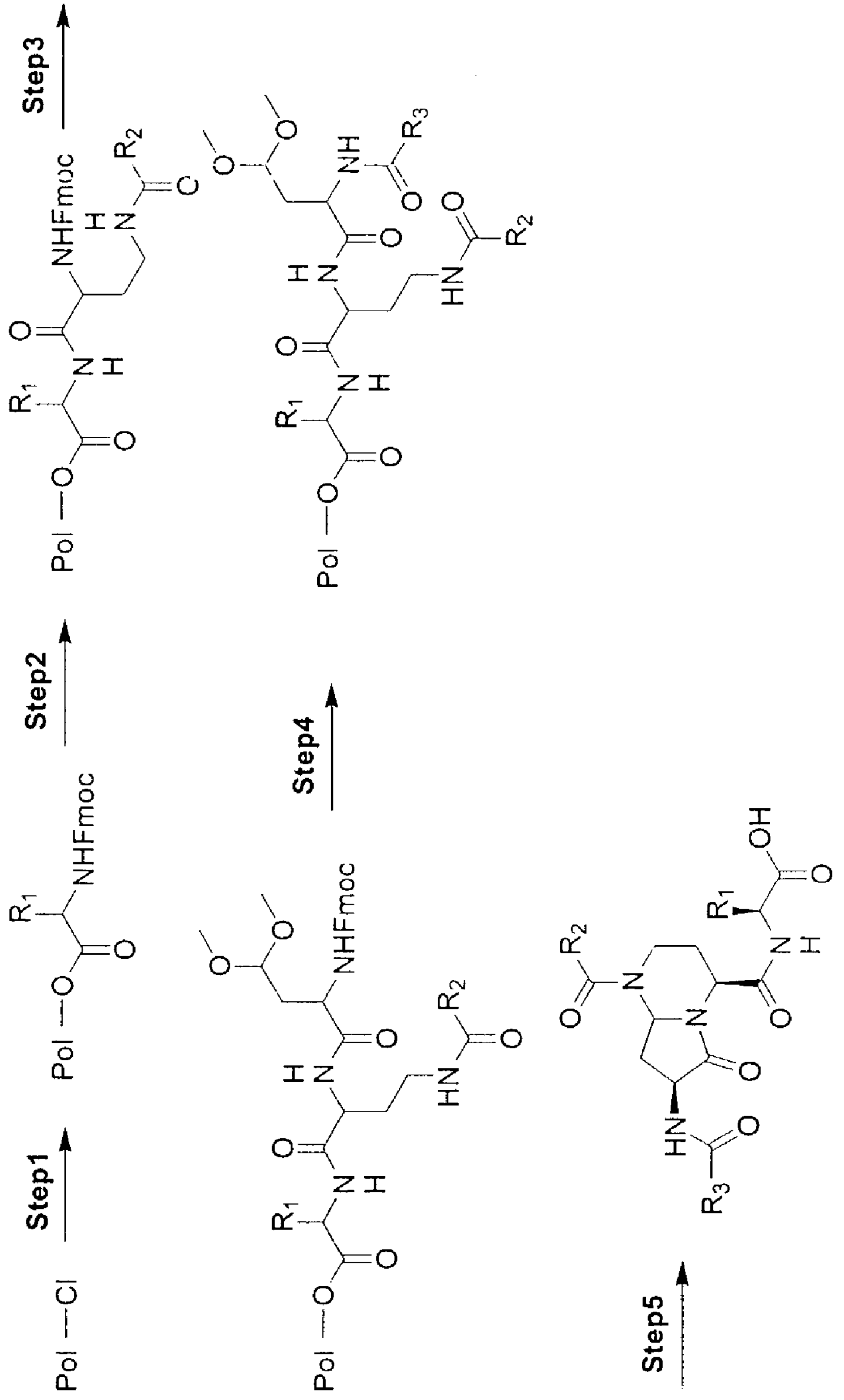
FIGS. 1 and 2 illustrate synthetic methodology for preparing libraries of the present invention, and compounds of the present invention.

Conformationally constrained compounds which mimic the secondary structure of β-strand regions of biologically active peptides and proteins are disclosed. Such β-strand mimetic structures have utility over a wide range of fields, including use as diagnostic and therapeutic agents. Libraries containing the β-strand mimetic structures of this invention are also disclosed as well as methods for screening the same to identify biologically active members.

In one aspect, the present invention is directed to β-strand mimetic structures and chemical libraries containing β-strand mimetic structures. The β-strand mimetic structures of the present invention are useful as bioactive agents, including (but not limited to) use as diagnostic, prophylactic and/or therapeutic agents. The β-strand mimetic structure libraries of this invention are useful in the identification of such bioactive agents. In the practice of the present invention, the libraries may contain from tens to hundreds to thousands (or greater) of individual β-strand mimetic structures (also referred to herein as "members").

In one aspect of the present invention, a β-strand mimetic structure is disclosed having the following structure (I):

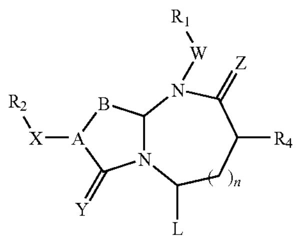

(I)

wherein A is —(CH)—, —N— or —$CH_2$—N—, B is —(C═O)— or —$(CH_2)_m$—, W is —(C═O)—, —Y(C═O)—, —NH(C═O)— or nothing, X is —NH—, —NH(C═O)— or nothing, Y is oxygen or sulfur, Z is oxygen or hydrogen (when Z is hydrogen, then C═Z represents $CH_2$), L is hydrogen, $R_5$, —C(O)$NHR_3$ or its equivalents, n=0 or 1 and m=1 or 2; $R_1$, $R_2$, $R_3$, $R_4$ and $R_5$ are the same or different and independently selected from hydrogen, an amino acid side chain moiety or derivative thereof, the remainder of the molecule, a linker and a solid support, and stereoisomers thereof.

In one aspect of the invention, $R_1$, $R_2$, $R_3$, $R_4$ and $R_5$ are independently selected from the group consisting of amino$C_{2-5}$alkyl, guanidine$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy, phenyl, substituted phenyl (where the substituents are independently selected from one or more of amino, amidino, guanidine, hydrazine, amidrazonyl, $C_{1-4}$alkylamino, $C_{1-4}$dialkylamino, halogen, perfluoro$C_{1-4}$alkyl, $C_{1-4}$alkyl, $C_{1-3}$alkoxy, nitro, carboxy, cyano, sulfuryl, or hydroxyl), benzyl, substituted benzyl (where the substituents on the benzyl are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, or hydroxyl), naphthyl, substituted naphthyl (where the substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), bis-phenyl methyl, substituted bis-phenyl methyl (where the substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), pyridyl, substituted pyridyl, (where the substituents are independently selected from one or more of amino amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), pyridyl$C_{1-4}$alkyl, substituted pyridyl $C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), pyrimidyl$C_{1-4}$alkyl, substituted pyrimidyl$C_{1-4}$alkyl (where the pyrimidine substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro, carboxy, cyano, sulfuryl, or hydroxyl), triazin-2-yl-$C_{1-4}$alkyl, substituted triazin-2-yl-$C_{1-4}$alkyl (where the triazine substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), imidazo$C_{1-4}$alkyl, substituted imidazol $C_{1-4}$alkyl (where the imidazole substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), imidazolinyl$C_{1-4}$alkyl, N-amidinopiperazinyl-N—$C_{0-4}$alkyl, hydroxy$C_{2-5}$alkyl, $C_{1-5}$alkylamino $C_{2-5}$alkyl, hydroxy$C_{2-5}$alkyl, $C_{1-5}$alkylamino$C_{2-5}$alkyl, $C_{1-5}$dialkyl-amino$C_{2-5}$alkyl, N-amidinopiperidinyl$C_{1-4}$alkyl and 4-aminocyclohexyl$C_{0-2}$alkyl.

In one embodiment, $R_1$, $R_2$ and $R_3$ are the same or different and represent the remainder of the compound, and $R_4$ is selected from an amino acid side chain moiety or derivative thereof. In another embodiment, L represents —C(═O)$NHR_3$, and $R_1$, $R_2$ and $R_3$ are the same or different and represent the remainder of the compound or an amino acid side chain moiety or derivative thereof, and $R_4$ is hydrogen.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromo-tyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

Amino Acid Side Chain Moieties

| Amino Acid Side Chain Moiety | Amino Acid |
|---|---|
| —H | Glycine |
| —$CH_3$ | Alanine |
| —$CH(CH_3)_2$ | Valine |
| —$CH_2$ $CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
| 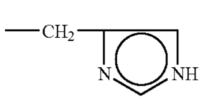 | Histidine |
| —$CH_2COO$- | Aspartic acid |
| —$CH_2CH_2COO$ | Glutamic acid |
| —$CH_2CONH_2$ | Asparagine |
| —$CH_2CH_2CONH_2$ | Glutamine |
| 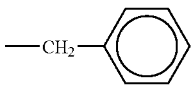 | Phenylalanine |
| 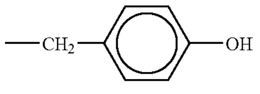 | Tyrosine |

TABLE 1-continued

| Amino Acid Side Chain Moieties | |
|---|---|
| Amino Acid Side Chain Moiety | Amino Acid |
| 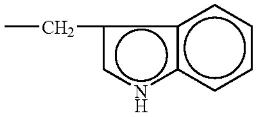 | Tryptophan |
| $—CH_2SH$ | Cysteine |
| $—CH_2CH_2SCH_3$ | Methionine |
| $—CH_2OH$ | Serine |
| $—CH(OH)CH_3$ | Threonine |
| 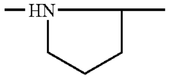 | Proline |
| 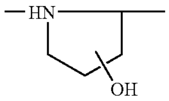 | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and phenylalanine may generally be classified as lower chain alkyl, aryl, or arylalkyl moieties. Derivatives of amino acid side chain moieties include other straight chain or branched, cyclic or noncyclic, substituted or unsubstituted, saturated or unsaturated lower chain alkyl, aryl or arylalkyl moieties.

As used herein, the terms "remainder of the compound" and "remainder of the molecule" are used to mean any moiety, agent, compound, support, molecule, linker, amino acid, peptide or protein covalently attached to the β-strand mimetic structure. The attachment is preferably at either the $R_1$ and/or $R_2$ and/or $R_3$ positions. This term also includes amino acid side chain moieties and derivatives thereof.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituent is selected from (but are not limited to) one or more of the following chemical moieties: —OH, —OR, —COOH, —COOR, $—CONH_2$, $—NH_2$, —NHR, —NRR, —SH, —SR, $—SO_2R$, $—SO_2H$, —SOR and halogen (including F, Cl, Br and I), wherein each occurrence of R is independently selected from straight chain or branched, cyclic or noncyclic, substituted or unsubstituted, saturated or unsaturated lower chain alkyl, aryl and aralkyl moieties. In one aspect the substituent has less than 18 carbon atoms. Moreover, cyclic lower chain alkyl, aryl and arylalkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

In one aspect of he invention, $R_1$, $R_2$ and $R_3$ moieties are selected from —OH, —OR, —COR, —COOR, $—CONH_2$, —CONR, —CONRR, $—NH_2$, —NHR, —NRR, $—SO_2R$ and —COSR, wherein each occurrence of R is as defined above.

In a further embodiment, and in addition to being an amino acid side chain moiety or derivative thereof (or the remainder of the compound in the case of $R_1$, $R_2$ and $R_3$), $R_1$, $R_2$ or $R_3$ may be a linker facilitating the linkage of the compound to another moiety or compound. For example, the compounds of this invention may be linked to one or more known compounds, such as biotin, for use in diagnostic or screening assay. Furthermore, $R_1$, $R_2$ or $R_3$ may be a linker joining the compound to a solid support (such as a support used in solid phase peptide synthesis) or alternatively, may be the support itself. In this embodiment, linkage to another moiety or compound, or to a solid support, is preferable at the $R_1$, $R_2$ or $R_3$ position, and more preferably at the $R_3$ position.

In the embodiment wherein X is absent, A is N, B is —(C═O)— and L is $—C(O)NHR_3$, the β-strand compounds of this invention have the following structure (I'):

(I')

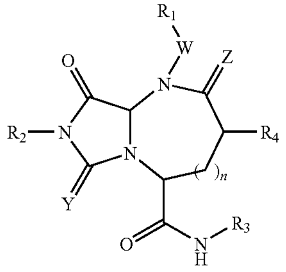

wherein $R_1$, $R_2$, $R_3$, $R_4$, W, Y, Z and n are as defined above. In a preferred embodiment, $R_2$ and $R_3$ represent the remainder of the compound, $R_1$ and $R_4$ are selected from amino acid side chain moieties.

In the embodiment wherein X is absent, A is N, B is $—(CH_2)_m—$ and L is $—C(O)NHR_3$, the β-strand mimetic structures of this invention include the following structure (I"):

(I")

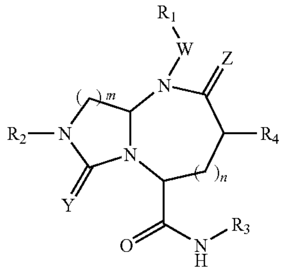

wherein $R_1$, $R_2$, $R_3$, $R_4$, W, Y, Z, m and n are as defined above. In a preferred embodiment, $R_2$ and $R_3$ represent the remainder of the compound, and $R_1$ and $R_4$ are selected from amino acid side chain moieties.

In a more specific embodiment wherein X is —NH—, A is —(CH)—, and B is $—(CH_2)_m—$ and L is $—C(O)NHR_3$, the β-strand mimetic structure has the following structure (I'''):

(I''')

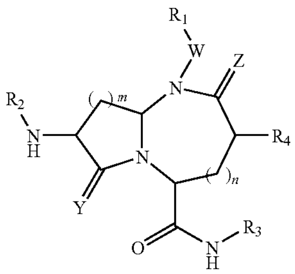

wherein $R_1$, $R_2$, $R_3$, $R_4$, W, Y, Z, m and n are as defined above.

In a more specific embodiment wherein A is $—CH_2—N—$, B is $—(CH_2)_m—$ and L is $—C(O)NHR_3$, the compounds of this invention have the following structure (I''''):

(I'''')

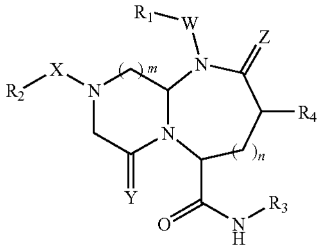

Optionally wherein $R_1$, $R_2$, $R_3$, $R_4$, W, X, Y, Z, m and n are as defined above, W is absent, Z is oxygen, and Y is oxygen.

The β-strand mimetic structures of the present invention may be prepared by utilizing appropriate starting component molecules (hereinafter referred to as "component pieces"). Briefly, in the synthesis of β-strand mimetic structures having structure (I'), first and second component pieces are coupled to form a combined first-second intermediate, and if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the β-strand mimetic structures of this invention. Alternatively, the β-strand mimetic structures of structure (I') may be prepared by sequential coupling of the individual component pieces either stepwise in solution or by solid phase synthesis as commonly practiced in solid phase peptide synthesis.

Within the context of the present invention, a "first component piece" has the following structure 1:

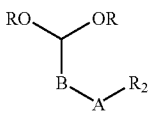

wherein $R_2$, A and B are as defined above, and R is a protective group suitable for use in peptide synthesis. Suitable R groups include alkyl groups and, in a preferred embodiment, R is a methyl group. Such first component pieces may be readily synthesized by reductive amination by mating $CH(OR)_2—(CH_2)_m—CHO$ with $H_2N—R_2$, or by displacement from $CH(OR)_2—(CH_2)_m—Br$.

A "second component piece" of this invention has the following structure 2:

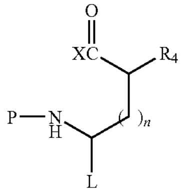

where L and $R_4$ are as defined above, P is an amino protective group suitable for use in peptide synthesis, and X represents the leaving group of the activated carboxylic acid group. Preferred protective groups include t-butyl dimethylsilyl (TBDMS), BOC, FMOC, and Alloc(allyloxycarbonyl). When L is $C(O)NHR_3$, then $—NHR_3$ may be an carboxyl protective group. N-Protected amino acids are commercially available, for example, FMOC amino acids are available from a variety of sources. The conversion of these N-protected amino acids to the second component pieces of this invention may be readily achieved by activation of the carboxylic acid group of the N-protected amino acid. Suitable activated carboxylic acid groups include acid halides where X is a halide such as chloride or bromide, acid anhydrides where X is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC).

In the case of the azido derivative of an amino acid serving as the second component piece, such compounds may be prepared from the corresponding amino acid by the reaction disclosed by Zaloom et al. (*J. Org. Chem.* 46: 5173-76, 1981).

A "third component piece" of this invention has the following structure 3:

$R_1—NH_2$ or $R_3—NH_2$ where $R_1$ and $R_3$ are as defined above. Suitable third component pieces are commercially available from a variety of sources, or may be readily prepared by standard organic synthetic techniques commonly utilized for the synthesis of primary amines.

More specifically, the β-strand mimetic structures of this invention of structure (I') are synthesized by reacting a first component piece with a second component piece to yield a combined first-second intermediate, followed by either reacting the combined first-second intermediate with third component pieces sequentially, or third and fourth component pieces, to provide a combined first-second-third-fourth intermediate, and then cyclizing this intermediate to yield the β-strand mimetic structure.

The general synthesis of a β-strand mimetic structure having structure I' may be accomplished by the following technique. A first component piece 1 is coupled with a second component piece 2 by using a coupling reagent such as phosgene to yield, after N-deprotection, a combined first-second intermediate 1-2 as illustrated below:

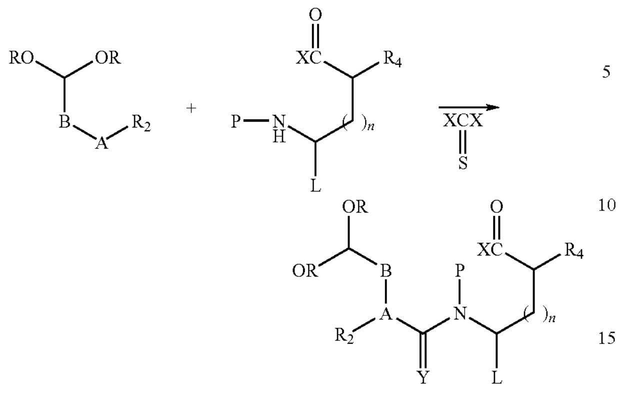

wherein, A, B, L, R, $R_2$, $R_4$, P, X and n are as defined above. $X_2C(=S)$ is an example of a coupling agent, and other type of coupling agents can be employed. The syntheses of representative component pieces of this invention are described in the Examples. The β-strand mimetic compounds of structures (I'') through (I''') may be made by techniques analogous to the modular component synthesis disclosed above, but with appropriate modifications to the component pieces.

In another aspect of this invention, libraries containing the β-strand mimetic structures of the present invention are disclosed. Once assembled, the libraries of the present invention may be screened to identify individual members having bioactivity. Such screening of the libraries for bioactive members may involve; for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members that are capable of interacting with the target of interest are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more specific biological targets of interest. When interaction does occur, the interacting bioactive mimetic (or mimetics) may be identified from the library members. The identification of a single (or limited number) of bioactive mimetic(s) from the library yields β-strand mimetic structures which are themselves biologically active, and thus useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second, third, and optionally fourth component pieces of this invention. More specifically, any amino acid sequence may be added to the N-terminal and/or C-terminal of the conformationally constrained compound. To this end, the mimetics may be synthesized on a solid support (such as PAM resin) by known techniques (see, e.g., John M. Stewart and Janis D. Young, Solid Phase Peptide Synthesis, 1984, Pierce Chemical Comp., Rockford, Ill.) or on a silyl-linked resin by alcohol attachment (see Randolph et al., *J. Am Chem. Soc.* 117: 5712-14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained β-strand is added to the sequence. A suitable conformationally constrained β-strand mimetic structure which has been previously synthesized by solution synthesis techniques may then be added as the next "amino acid" to the solid phase synthesis (i.e., the conformationally constrained β-strand mimetic, which has both an N-terminus and a C-terminus, may be utilized as the next amino acid to be added to the linear peptide). Upon incorporation of the conformationally constrained β-strand mimetic structure into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained β-strand mimetic structures in solution using known solution coupling techniques.

In another aspect of this invention, methods for constructing the libraries are disclosed. Traditional combinatorial chemistry techniques (see, e.g., Gallop et al., *J. Med. Chem.* 37: 1233-1251, 1994) permit a vast number of compounds to be rapidly prepared by the sequential combination of reagents to a basic molecular scaffold. Combinatorial techniques have been used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

In a further aspect of this invention, methods for screening the libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the calorimetric assay disclosed by Lam et al. (*Nature* 354: 82-84, 1991) or Griminski et al. (*Biotechnology* 12: 1008-1011, 1994) (both of which are incorporated herein by reference). In a preferred embodiment, the library members are in solution and the target is immobilized on a solid phase. Alternatively, the library may be immobilized on a solid phase and may be probed by contacting it with the target in solution.

The synthesis of the peptide mimetics of a library of the present invention may be accomplished using the general scheme for preparing a β-strand mimetics library as shown in FIG. 1. The synthesis of selected peptide mimetics of the bicyclic template libraries of the present invention was accomplished using a FlexChem Reactor Block which has a 96 well plate. In the above scheme 'Pol' represents 2-chlorotrityl chloride resin (Novabiochem) and a detailed procedure is provided below.

Step 1 The 2-chlorotrityl chloride resin (1 mmol/g) and a solution Fmoc-$R_1$-Amino Acid (1.5 equiv.) and DIEA (2 equiv.) in DCE were placed in a 96 well Robinson block (Flexchem). The reaction mixture was shaken for 12 hours at room temperature. The resin washed with DMF, MeOH, and the DCM.

Step 2 To the resin swollen by DMF before reaction was added 25% piperidine in DMF. Thereafter, the reaction mixture was shaken for 30 min at room temperature. The deprotection step was repeated and the product mixture was washed with DMF, MeOH, and then DCM. A solution of 4-$R_2$-amino-2-Fmoc-aminobutyric acid (1.5 equiv.), DIC (1.5 equiv.), and HOBT (1.5 equiv.) in NMP was added to the resin. After the reaction mixture was shaken for 12 hours at room temperature, the resin was washed with DMF, MeOH, and then DCM.

Step 3 To the resin swollen by DMF before reaction was added 25% piperidine in DMF. Thereafter, the reaction mixture was shaken for 30 min at room temperature. The deprotection step was repeated and the product mixture was washed with DMF, MeOH, and then DCM. A solution of 2-(9H-fluoren-9-ylmethoxycarbonylamino)-5, 5-dimethoxy-pentanoic acid (1.5 equiv.), DIC (1.5 equiv.), and HOBT (1.5 equiv.) in NMP was added to the resin. The reaction mixture was shaken for 12 hours at room temperature, and then the resin was washed with DMF, MeOH, and then DCM.

Step 4 To the resin swollen by DMF before reaction was added 25% piperidine in DMF. Thereafter, the reaction mixture was shaken for 30 min at room temperature. The deprotection step was repeated and the product mixture was washed with DMF, MeOH, and then DCM. A solution of commercially available $R_3$-acid (1.5 equiv.), DIC (1.5 equiv.), and HOBT (1.5 equiv.) in NMP was added to the resin. The reaction mixture was shaken for 12 hours at room temperature, and then the resin was washed with DMF, MeOH, and then DCM.

Step 5 The resin was treated with formic acid (1.2 mL each well) for 18 hours at room temperature. Thereafter, the resin was removed by filtration, the filtrate was condensed under reduced pressure using SpeedVac (Servant) to give the product as oil. These products were diluted with 50% water/acetonitrile and then lyophilized after freezing.

Table 2 shows a β-strand mimetics library that may be prepared according to the present invention, of which representative preparation is given in Example 9. Compounds of Table 2 illustrate one aspect of the invention, namely compounds wherein A is —(CH)—, B is —$(CH_2)_m$— with m=1, W is —(C═O)—, X is —NH(C═O)—, Y is oxygen, Z is hydrogen so that C═Z represents $CH_2$, L is —C(═O)$NHR_3$, n=0, $R_4$ is hydrogen, and $R_1$, $R_2$, and $R_3$ are the same or different and are independently selected from an amino acid side chain moiety or derivative thereof, the remainder of the molecule, a linker and a solid support, and stereoisomers thereof. In various embodiments of this aspect of the invention, $R_1$, $R_2$, and $R_3$ are independently selected from relatively low molecular weight moieties, i.e., organic groups having molecular weights of between 15 (methyl) and 1,000 g/mol; and/or at least one of $R_1$, $R_2$, and $R_3$ represents an amino acid side chain or derivative thereof. For example, in the compounds of Table 2, $R^3$ represents aspartic acid derivatives. In one aspect, the compounds of the present invention have a molecular weight within the range of about 440 to 750 g/mol, where the compounds of Table 2 provide numerous illustrations of such compounds.

TABLE 2

THE BETA-STRAND MIMETICS LIBRARY

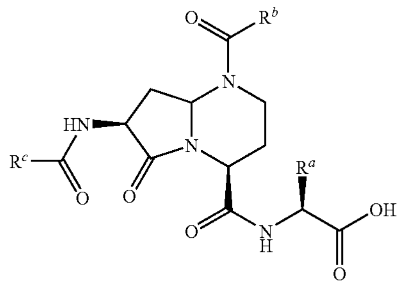

| No. | $R^a$ | $R^b$ | $R^c$ | Mol. Weight | M + H |
|---|---|---|---|---|---|
| 1 | Methyl | Phenyl | 4-Methoxybenzyl | 522 | 522 |
| 2 | Methyl | Phenyl | 3,4-$Cl_2$-benzyl | 547 | 547 |
| 3 | Methyl | Phenyl | 1-Naphthyl | 528 | 528 |
| 4 | Methyl | Phenyl | Piperonyl | 522 | 522 |
| 5 | Methyl | Phenyl | 2,4,5-Trimethoxyphenyl | 568 | 568 |
| 6 | Methyl | Phenyl | 2-Thienylmethyl | 498 | 498 |
| 7 | Methyl | Phenyl | 1-Naphthylmethyl | 542 | 542 |
| 8 | Methyl | Phenyl | Phenethyl | 506 | 506 |
| 9 | Methyl | Phenyl | 3-Methoxyphenyl | 508 | 508 |
| 10 | Methyl | Phenyl | N-Benzoylaminoethyl | 535 | 535 |
| 11 | Methyl | Phenyl | Benzyl | 492 | 492 |
| 12 | Methyl | Phenyl | 4-Nitrobenzyl | 537 | 537 |
| 13 | Isopropyl | Phenyl | 4-Methoxybenzyl | 550 | 550 |
| 14 | Isopropyl | Phenyl | 3,4-$Cl_2$-benzyl | 575 | 575 |
| 15 | Isopropyl | Phenyl | 1-Naphthyl | 556 | 556 |
| 16 | Isopropyl | Phenyl | Piperonyl | 550 | 550 |
| 17 | Isopropyl | Phenyl | 2,4,5-Trimethoxyphenyl | 596 | 596 |
| 18 | Isopropyl | Phenyl | 2-Thienylmethyl | 526 | 526 |
| 19 | Isopropyl | Phenyl | 1-Naphthylmethyl | 570 | 570 |
| 20 | Isopropyl | Phenyl | Phenethyl | 534 | 534 |
| 21 | Isopropyl | Phenyl | 3-Methoxyphenyl | 536 | 536 |

TABLE 2-continued

THE BETA-STRAND MIMETICS LIBRARY

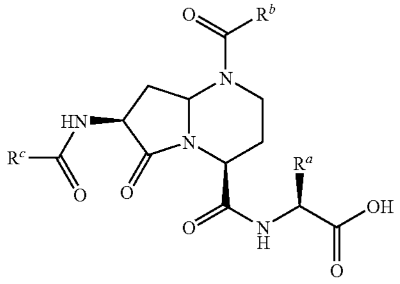

| No. | $R^a$ | $R^b$ | $R^c$ | Mol. Weight | M + H |
|---|---|---|---|---|---|
| 22 | Isopropyl | Phenyl | N-Benzoylaminoethyl | 563 | 563 |
| 23 | Isopropyl | Phenyl | Benzyl | 520 | 520 |
| 24 | Isopropyl | Phenyl | 4-Nitrobenzyl | 565 | 565 |
| 25 | Isobutyl | Phenyl | 4-Methoxybenzyl | 564 | 564 |
| 26 | Isobutyl | Phenyl | 3,4-$Cl_2$-benzyl | 589 | 589 |
| 27 | Isobutyl | Phenyl | 1-Naphthyl | 570 | 570 |
| 28 | Isobutyl | Phenyl | Piperonyl | 564 | 564 |
| 29 | Isobutyl | Phenyl | 2,4,5-Trimethoxyphenyl | 610 | 610 |
| 30 | Isobutyl | Phenyl | 2-Thienylmethyl | 540 | 540 |
| 31 | Isobutyl | Phenyl | 1-Naphthylmethyl | 584 | 584 |
| 32 | Isobutyl | Phenyl | Phenethyl | 548 | 548 |
| 33 | Isobutyl | Phenyl | 3-Methoxyphenyl | 550 | 550 |
| 34 | Isobutyl | Phenyl | N-Benzoylaminoethyl | 577 | 577 |
| 35 | Isobutyl | Phenyl | Benzyl | 534 | 534 |
| 36 | Isobutyl | Phenyl | 4-Nitrobenzyl | 579 | 579 |
| 37 | Benzyl | Phenyl | 4-Methoxybenzyl | 598 | 598 |
| 38 | Benzyl | Phenyl | 3,4-$Cl_2$-benzyl | 623 | 623 |
| 39 | Benzyl | Phenyl | 1-Naphthyl | 604 | 604 |
| 40 | Benzyl | Phenyl | Piperonyl | 598 | 598 |
| 41 | Benzyl | Phenyl | 2,4,5-Trimethoxyphenyl | 644 | 644 |
| 42 | Benzyl | Phenyl | 2-Thienylmethyl | 574 | 574 |
| 43 | Benzyl | Phenyl | 1-Naphthylmethyl | 618 | 618 |
| 44 | Benzyl | Phenyl | Phenethyl | 582 | 582 |
| 45 | Benzyl | Phenyl | 3-Methoxyphenyl | 584 | 584 |
| 46 | Benzyl | Phenyl | N-Benzoylaminoethyl | 611 | 611 |
| 47 | Benzyl | Phenyl | Benzyl | 568 | 568 |
| 48 | Benzyl | Phenyl | 4-Nitrobenzyl | 613 | 613 |
| 49 | Methyl | Methoxy | 4-Methoxybenzyl | 476 | 476 |
| 50 | Methyl | Methoxy | 3,4-$Cl_2$-benzyl | 501 | 501 |
| 51 | Methyl | Methoxy | 1-Naphthyl | 482 | 482 |
| 52 | Methyl | Methoxy | Piperonyl | 476 | 476 |
| 53 | Methyl | Methoxy | 2,4,5-Trimethoxyphenyl | 522 | 522 |
| 54 | Methyl | Methoxy | 2-Thienylmethyl | 452 | 452 |
| 55 | Methyl | Methoxy | 1-Naphthylmethyl | 496 | 496 |
| 56 | Methyl | Methoxy | Phenethyl | 460 | 460 |
| 57 | Methyl | Methoxy | 3-Methoxyphenyl | 462 | 462 |
| 58 | Methyl | Methoxy | N-Benzoylaminoethyl | 489 | 489 |
| 59 | Methyl | Methoxy | Benzyl | 446 | 446 |
| 60 | Methyl | Methoxy | 4-Nitrobenzyl | 491 | 491 |
| 61 | Isopropyl | Methoxy | 4-Methoxybenzyl | 504 | 504 |
| 62 | Isopropyl | Methoxy | 3,4-$Cl_2$-benzyl | 529 | 529 |
| 63 | Isopropyl | Methoxy | 1-Naphthyl | 510 | 510 |
| 64 | Isopropyl | Methoxy | Piperonyl | 504 | 504 |
| 65 | Isopropyl | Methoxy | 2,4,5-Trimethoxyphenyl | 550 | 550 |
| 66 | Isopropyl | Methoxy | 2-Thienylmethyl | 480 | 480 |
| 67 | Isopropyl | Methoxy | 1-Naphthylmethyl | 524 | 524 |
| 68 | Isopropyl | Methoxy | Phenethyl | 488 | 488 |
| 69 | Isopropyl | Methoxy | 3-Methoxyphenyl | 490 | 490 |
| 70 | Isopropyl | Methoxy | N-Benzoylaminoethyl | 517 | 517 |
| 71 | Isopropyl | Methoxy | Benzyl | 474 | 474 |
| 72 | Isopropyl | Methoxy | 4-Nitrobenzyl | 519 | 519 |
| 73 | Isobutyl | Methoxy | 4-Methoxybenzyl | 518 | 518 |
| 74 | Isobutyl | Methoxy | 3,4-$Cl_2$-benzyl | 543 | 543 |
| 75 | Isobutyl | Methoxy | 1-Naphthyl | 524 | 524 |
| 76 | Isobutyl | Methoxy | Piperonyl | 518 | 518 |
| 77 | Isobutyl | Methoxy | 2,4,5-Trimethoxyphenyl | 564 | 564 |
| 78 | Isobutyl | Methoxy | 2-Thienylmethyl | 494 | 494 |
| 79 | Isobutyl | Methoxy | 1 -Naphthylmethyl | 538 | 538 |

TABLE 2-continued

THE BETA-STRAND MIMETICS LIBRARY

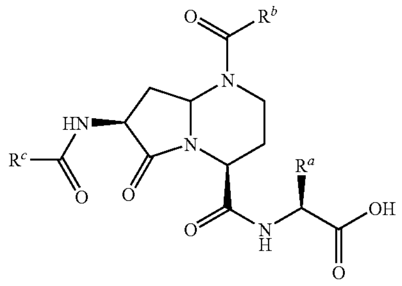

| No. | $R^a$ | $R^b$ | $R^c$ | Mol. Weight | M + H |
|---|---|---|---|---|---|
| 80 | Isobutyl | Methoxy | Phenethyl | 502 | 502 |
| 81 | Isobutyl | Methoxy | 3-Methoxyphenyl | 504 | 504 |
| 82 | Isobutyl | Methoxy | N-Benzoylaminoethyl | 531 | 531 |
| 83 | Isobutyl | Methoxy | Benzyl | 488 | 488 |
| 84 | Isobutyl | Methoxy | 4-Nitrobenzyl | 533 | 533 |
| 85 | Benzyl | Methoxy | 4-Methoxybenzyl | 552 | 552 |
| 86 | Benzyl | Methoxy | 3,4-$Cl_2$-benzyl | 577 | 577 |
| 87 | Benzyl | Methoxy | 1-Naphthyl | 558 | 558 |
| 88 | Benzyl | Methoxy | Piperonyl | 552 | 552 |
| 89 | Benzyl | Methoxy | 2,4,5-Trimethoxyphenyl | 598 | 598 |
| 90 | Benzyl | Methoxy | 2-Thienylmethyl | 528 | 528 |
| 91 | Benzyl | Methoxy | 1-Naphthylmethyl | 572 | 572 |
| 92 | Benzyl | Methoxy | Phenethyl | 536 | 536 |
| 93 | Benzyl | Methoxy | 3-Methoxyphenyl | 538 | 538 |
| 94 | Benzyl | Methoxy | N-Benzoylaminoethyl | 565 | 565 |
| 95 | Benzyl | Methoxy | Benzyl | 522 | 522 |
| 96 | Benzyl | Methoxy | 4-Nitrobenzyl | 567 | 567 |
| 97 | 2-Methylpropyl | Phenyl | 4-Methoxybenzyl | 564 | 564 |
| 98 | 2-Methylpropyl | Phenyl | 3,4-$Cl_2$-benzyl | 589 | 589 |
| 99 | 2-Methylpropyl | Phenyl | 1-Naphthyl | 570 | 570 |
| 100 | 2-Methylpropyl | Phenyl | Piperonyl | 564 | 564 |
| 101 | 2-Methylpropyl | Phenyl | 2,4,5-Trimethoxyphenyl | 610 | 610 |
| 102 | 2-Methylpropyl | Phenyl | 2-Thienylmethyl | 550 | 550 |
| 103 | 2-Methylpropyl | Phenyl | 1-Naphthylmethyl | 584 | 584 |
| 104 | 2-Methylpropyl | Phenyl | Phenethyl | 548 | 548 |
| 105 | 2-Methylpropyl | Phenyl | 3-Methoxyphenyl | 550 | 550 |
| 106 | 2-Methylpropyl | Phenyl | N-Benzoylaminoethyl | 577 | 577 |
| 107 | 2-Methylpropyl | Phenyl | Benzyl | 534 | 534 |
| 108 | 2-Methylpropyl | Phenyl | 4-Nitrobenzyl | 579 | 579 |
| 109 | Methylthioethyl | Phenyl | 4-Methoxybenzyl | 582 | 582 |
| 110 | Methylthioethyl | Phenyl | 3,4-$Cl_2$-benzyl | 607 | 607 |
| 111 | Methylthioethyl | Phenyl | 1-Naphthyl | 588 | 588 |
| 112 | Methylthioethyl | Phenyl | Piperonyl | 582 | 582 |
| 113 | Methylthioethyl | Phenyl | 2,4,5-Trimethoxyphenyl | 628 | 628 |
| 114 | Methylthioethyl | Phenyl | 2-Thienylmethyl | 568 | 568 |
| 115 | Methylthioethyl | Phenyl | 1-Naphthylmethyl | 602 | 602 |
| 116 | Methylthioethyl | Phenyl | Phenethyl | 566 | 566 |
| 117 | Methylthioethyl | Phenyl | 3-Methoxyphenyl | 568 | 568 |
| 118 | Methylthioethyl | Phenyl | N-Benzoylaminoethyl | 595 | 595 |
| 119 | Methyithioethyl | Phenyl | Benzyl | 552 | 552 |
| 120 | Methylthioethyl | Phenyl | 4-Nitrobenzyl | 597 | 597 |
| 121 | 4-Hydroxybenzyl | Phenyl | 4-Methoxybenzyl | 614 | 614 |
| 122 | 4-Hydroxybenzyl | Phenyl | 3,4-$Cl_2$-benzyl | 639 | 639 |
| 123 | 4-Hydroxybenzyl | Phenyl | 1-Naphthyl | 620 | 620 |
| 124 | 4-Hydroxybenzyl | Phenyl | Piperonyl | 614 | 614 |
| 125 | 4-Hydroxybenzyl | Phenyl | 2,4,5-Trimethoxyphenyl | 660 | 660 |
| 126 | 4-Hydroxybenzyl | Phenyl | 2-Thienylmethyl | 600 | 600 |
| 127 | 4-Hydroxybenzyl | Phenyl | 1-Naphthylmethyl | 634 | 634 |
| 128 | 4-Hydroxybenzyl | Phenyl | Phenethyl | 598 | 598 |
| 129 | 4-Hydroxybenzyl | Phenyl | 3-Methoxyphenyl | 600 | 600 |
| 130 | 4-Hydroxybenzyl | Phenyl | N-Benzoylaminoethyl | 627 | 627 |
| 131 | 4-Hydroxybenzyl | Phenyl | Benzyl | 584 | 584 |
| 132 | 4-Hydroxybenzyl | Phenyl | 4-Nitrobenzyl | 629 | 629 |
| 133 | Cyclohexylmethyl | Phenyl | 4-Methoxybenzyl | 604 | 604 |
| 134 | Cyclohexylmethyl | Phenyl | 3,4-$Cl_2$-benzyl | 629 | 629 |
| 135 | Cyclohexylmethyl | Phenyl | 1-Naphthyl | 610 | 610 |
| 136 | Cyclohexylmethyl | Phenyl | Piperonyl | 604 | 604 |
| 137 | Cyclohexylmethyl | Phenyl | 2,4,5-Trimethoxyphenyl | 650 | 650 |

TABLE 2-continued

THE BETA-STRAND MIMETICS LIBRARY

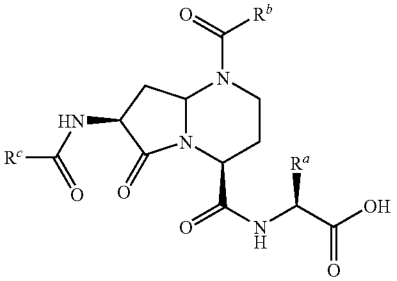

| No. | $R^a$ | $R^b$ | $R^c$ | Mol. Weight | M + H |
|---|---|---|---|---|---|
| 138 | Cyclohexylmethyl | Phenyl | 2-Thienylmethyl | 590 | 590 |
| 139 | Cyclohexylmethyl | Phenyl | 1-Naphthylmethyl | 624 | 624 |
| 140 | Cyclohexylmethyl | Phenyl | Phenethyl | 588 | 588 |
| 141 | Cyclohexylmethyl | Phenyl | 3-Methoxyphenyl | 590 | 590 |
| 142 | Cyclohexylmethyl | Phenyl | N-Benzoylaminoethyl | 617 | 617 |
| 143 | Cyclohexylmethyl | Phenyl | Benzyl | 574 | 574 |
| 144 | Cyclohexylmethyl | Phenyl | 4-Nitrobenzyl | 619 | 619 |
| 145 | 2-Methylpropyl | Methoxy | 4-Methoxybenzyl | 518 | 518 |
| 146 | 2-Methylpropyl | Methoxy | 3,4-$Cl_2$-benzyl | 543 | 543 |
| 147 | 2-Methylpropyl | Methoxy | 1-Naphthyl | 524 | 524 |
| 148 | 2-Methylpropyl | Methoxy | Piperonyl | 518 | 518 |
| 149 | 2-Methylpropyl | Methoxy | 2,4,5-Trimethoxyphenyl | 564 | 564 |
| 150 | 2-Methylpropyl | Methoxy | 2-Tthienylmethyl | 504 | 504 |
| 151 | 2-Methylpropyl | Methoxy | 1-Naphthylmethyl | 538 | 538 |
| 152 | 2-Methylpropyl | Methoxy | Phenethyl | 502 | 502 |
| 153 | 2-Methylpropyl | Methoxy | 3-Methoxyphenyl | 504 | 504 |
| 154 | 2-Methylpropyl | Methoxy | N-Benzoylaminoethyl | 531 | 531 |
| 155 | 2-Methylpropyl | Methoxy | Benzyl | 488 | 488 |
| 156 | 2-Methylpropyl | Methoxy | 4-Nitrobenzyl | 533 | 533 |
| 157 | Methylthioethyl | Methoxy | 4-Methoxybenzyl | 536 | 536 |
| 158 | Methylthioethyl | Methoxy | 3,4-$Cl_2$-benzyl | 561 | 561 |
| 159 | Methylthioethyl | Methoxy | 1-Naphthyl | 542 | 542 |
| 160 | Methylthioethyl | Methoxy | Piperonyl | 536 | 536 |
| 161 | Methylthioethyl | Methoxy | 2,4,5-Trimethoxyphenyl | 582 | 582 |
| 162 | Methylthioethyl | Methoxy | 2-Tthienylmethyl | 522 | 522 |
| 163 | Methylthioethyl | Methoxy | 1-Naphthylmethyl | 556 | 556 |
| 164 | Methylthioethyl | Methoxy | Phenethyl | 520 | 520 |
| 165 | Methylthioethyl | Methoxy | 3-Methoxyphenyl | 522 | 522 |
| 166 | Methylthioethyl | Methoxy | N-Benzoylaminoethyl | 549 | 549 |
| 167 | Methylthioethyl | Methoxy | Benzyl | 506 | 506 |
| 168 | Methylthioethyl | Methoxy | 4-Nitrobenzyl | 551 | 551 |
| 169 | 4-Hydroxybenzyl | Methoxy | 4-Methoxybenzyl | 568 | 568 |
| 170 | 4-Hydroxybenzyl | Methoxy | 3,4-$Cl_2$-benzyl | 593 | 593 |
| 171 | 4-Hydroxybenzyl | Methoxy | 1-Naphthyl | 574 | 574 |
| 172 | 4-Hydroxybenzyl | Methoxy | Piperonyl | 568 | 568 |
| 173 | 4-Hydroxybenzyl | Methoxy | 2,4,5-Trimethoxyphenyl | 614 | 614 |
| 174 | 4-Hydroxybenzyl | Methoxy | 2-Tthienylmethyl | 554 | 554 |
| 175 | 4-Hydroxybenzyl | Methoxy | 1-Naphthylmethyl | 588 | 588 |
| 176 | 4-Hydroxybenzyl | Methoxy | Phenethyl | 552 | 552 |
| 177 | 4-Hydroxybenzyl | Methoxy | 3-Methoxyphenyl | 554 | 554 |
| 178 | 4-Hydroxybenzyl | Methoxy | N-Benzoylaminoethyl | 581 | 581 |
| 179 | 4-Hydroxybenzyl | Methoxy | Benzyl | 538 | 538 |
| 180 | 4-Hydroxybenzyl | Methoxy | 4-Nitrobenzyl | 583 | 583 |
| 181 | Cyclohexylmethyl | Methoxy | 4-Methoxybenzyl | 558 | 558 |
| 182 | Cyclohexylmethyl | Methoxy | 3,4-$Cl_2$-benzyl | 583 | 583 |
| 183 | Cyclohexylmethyl | Methoxy | 1-Naphthyl | 564 | 564 |
| 184 | Cyclohexylmethyl | Methoxy | Piperonyl | 558 | 558 |
| 185 | Cyclohexylmethyl | Methoxy | 2,4,5-Trimethoxyphenyl | 604 | 604 |
| 186 | Cyclohexylmethyl | Methoxy | 2-Thienylmethyl | 544 | 544 |
| 187 | Cyclohexylmethyl | Methoxy | 1-Naphthylmethyl | 578 | 578 |
| 188 | Cyclohexylmethyl | Methoxy | Phenethyl | 542 | 542 |
| 189 | Cyclohexylmethyl | Methoxy | 3-Methoxyphenyl | 544 | 544 |
| 190 | Cyclohexylmethyl | Methoxy | N-Benzoylaminoethyl | 571 | 571 |
| 191 | Cyclohexylmethyl | Methoxy | Benzyl | 528 | 528 |
| 192 | Cyclohexylmethyl | Methoxy | 4-Nitrobenzyl | 573 | 573 |
| 193 | Methyl | Phenyl | 4-Methoxybenzyl | 521 | 521 |
| 194 | Methyl | Phenyl | 3,4-$Cl_2$-benzyl | 546 | 546 |
| 195 | Methyl | Phenyl | 1-Naphthyl | 527 | 527 |

TABLE 2-continued

THE BETA-STRAND MIMETICS LIBRARY

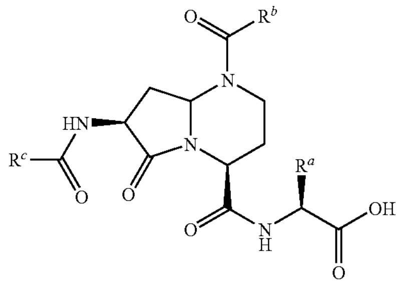

| No. | $R^a$ | $R^b$ | $R^c$ | Mol. Weight | M + H |
|---|---|---|---|---|---|
| 196 | Methyl | Phenyl | Piperonyl | 521 | 521 |
| 197 | Methyl | Phenyl | 2,4,5-Trimethoxyphenyl | 567 | 567 |
| 198 | Methyl | Phenyl | 3-Hydroxybenzyl | 507 | 507 |
| 199 | Methyl | Phenyl | 1-Naphthylmethyl | 541 | 541 |
| 200 | Methyl | Phenyl | Phenethyl | 505 | 505 |
| 201 | Methyl | Phenyl | 3-Methoxyphenyl | 507 | 507 |
| 202 | Methyl | Phenyl | N-Benzoylaminoethyl | 534 | 534 |
| 203 | Methyl | Phenyl | Benzyl | 491 | 491 |
| 204 | Methyl | Phenyl | 4-Nitrobenzyl | 536 | 536 |
| 205 | Isopropyl | Phenyl | 4-Methoxybenzyl | 549 | 549 |
| 206 | Isopropyl | Phenyl | 3,4-$Cl_2$-benzyl | 574 | 574 |
| 207 | Isopropyl | Phenyl | 1-Naphthyl | 555 | 555 |
| 208 | Isopropyl | Phenyl | Piperonyl | 549 | 549 |
| 209 | Isopropyl | Phenyl | 2,4,5-Trimethoxyphenyl | 595 | 595 |
| 210 | Isopropyl | Phenyl | 3-Hydroxybenzyl | 535 | 535 |
| 211 | Isopropyl | Phenyl | 1-Naphthylmethyl | 569 | 569 |
| 212 | Isopropyl | Phenyl | Phenethyl | 533 | 533 |
| 213 | Isopropyl | Phenyl | 3-Methoxyphenyl | 535 | 535 |
| 214 | Isopropyl | Phenyl | N-Benzoylaminoethyl | 562 | 562 |
| 215 | Isopropyl | Phenyl | Benzyl | 519 | 519 |
| 216 | Isopropyl | Phenyl | 4-Nitrobenzyl | 564 | 564 |
| 217 | Isobutyl | Phenyl | 4-Methoxybenzyl | 563 | 563 |
| 218 | Isobutyl | Phenyl | 3,4-$Cl_2$-benzyl | 588 | 588 |
| 219 | Isobutyl | Phenyl | 1-Naphthyl | 569 | 569 |
| 220 | Isobutyl | Phenyl | Piperonyl | 563 | 563 |
| 221 | Isobutyl | Phenyl | 2,4,5-Trimethoxyphenyl | 609 | 609 |
| 222 | Isobutyl | Phenyl | 3-Hydroxybenzyl | 549 | 549 |
| 223 | Isobutyl | Phenyl | 1-Naphthylmethyl | 583 | 583 |
| 224 | Isobutyl | Phenyl | Phenethyl | 547 | 547 |
| 225 | Isobutyl | Phenyl | 3-Methoxyphenyl | 549 | 549 |
| 226 | Isobutyl | Phenyl | N-Benzoylaminoethyl | 576 | 576 |
| 227 | Isobutyl | Phenyl | Benzyl | 533 | 533 |
| 228 | Isobutyl | Phenyl | 4-Nitrobenzyl | 578 | 578 |
| 229 | Benzyl | Phenyl | 4-Methoxybenzyl | 597 | 597 |
| 230 | Benzyl | Phenyl | 3,4-$Cl_2$-benzyl | 622 | 622 |
| 231 | Benzyl | Phenyl | 1-Naphthyl | 603 | 603 |
| 232 | Benzyl | Phenyl | Piperonyl | 597 | 597 |
| 233 | Benzyl | Phenyl | 2,4,5-Trimethoxyphenyl | 643 | 643 |
| 234 | Benzyl | Phenyl | 3-Hydroxybenzyl | 583 | 583 |
| 235 | Benzyl | Phenyl | 1-Naphthylmethyl | 617 | 617 |
| 236 | Benzyl | Phenyl | Phenethyl | 581 | 581 |
| 237 | Benzyl | Phenyl | 3-Methoxyphenyl | 583 | 583 |
| 238 | Benzyl | Phenyl | N-Benzoylaminoethyl | 610 | 610 |
| 239 | Benzyl | Phenyl | Benzyl | 567 | 567 |
| 240 | Benzyl | Phenyl | 4-Nitrobenzyl | 612 | 612 |
| 241 | 2-Methylpropyl | Phenyl | 4-Methoxybenzyl | 563 | 563 |
| 242 | 2-Methylpropyl | Phenyl | 3,4-$Cl_2$-benzyl | 588 | 588 |
| 243 | 2-Methylpropyl | Phenyl | 1-Naphthyl | 569 | 569 |
| 244 | 2-Methylpropyl | Phenyl | Piperonyl | 563 | 563 |
| 245 | 2-Methylpropyl | Phenyl | 2,4,5-Trimethoxyphenyl | 609 | 609 |
| 246 | 2-Methylpropyl | Phenyl | 3-Hydroxybenzyl | 549 | 549 |
| 247 | 2-Methylpropyl | Phenyl | 1-Naphthylmethyl | 583 | 583 |
| 248 | 2-Methylpropyl | Phenyl | Phenethyl | 547 | 547 |
| 249 | 2-Methylpropyl | Phenyl | 3-Methoxyphenyl | 549 | 549 |
| 250 | 2-Methylpropyl | Phenyl | N-Benzoylaminoethyl | 576 | 576 |
| 251 | 2-Methylpropyl | Phenyl | Benzyl | 533 | 533 |
| 252 | 2-Methylpropyl | Phenyl | 4-Nitrobenzyl | 578 | 578 |
| 253 | Methylthioethyl | Phenyl | 4-Methoxybenzyl | 581 | 581 |

TABLE 2-continued

THE BETA-STRAND MIMETICS LIBRARY

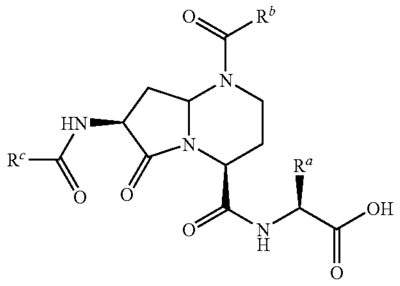

| No. | $R^a$ | $R^b$ | $R^c$ | Mol. Weight | M + H |
|---|---|---|---|---|---|
| 254 | Methylthioethyl | Phenyl | 3,4-$Cl_2$-benzyl | 606 | 606 |
| 255 | Methylthioethyl | Phenyl | 1-Naphthyl | 587 | 587 |
| 256 | Methylthioethyl | Phenyl | Piperonyl | 581 | 581 |
| 257 | Methylthioethyl | Phenyl | 2,4,5-Trimethoxyphenyl | 627 | 627 |
| 258 | Methylthioethyl | Phenyl | 3-Hydroxybenzyl | 567 | 567 |
| 259 | Methylthioethyl | Phenyl | 1-Naphthylmethyl | 601 | 601 |
| 260 | Methylthioethyl | Phenyl | Phenethyl | 565 | 565 |
| 261 | Methylthioethyl | Phenyl | 3-Methoxyphenyl | 567 | 567 |
| 262 | Methylthioethyl | Phenyl | N-Benzoylaminoethyl | 594 | 594 |
| 263 | Methylthioethyl | Phenyl | Benzyl | 551 | 551 |
| 264 | Methylthioethyl | Phenyl | 4-Nitrobenzyl | 596 | 596 |
| 265 | 4-Hydroxybenzyl | Phenyl | 4-Methoxybenzyl | 613 | 613 |
| 266 | 4-Hydroxybenzyl | Phenyl | 3,4-$Cl_2$-benzyl | 638 | 638 |
| 267 | 4-Hydroxybenzyl | Phenyl | 1-Naphthyl | 619 | 619 |
| 268 | 4-Hydroxybenzyl | Phenyl | Piperonyl | 613 | 613 |
| 269 | 4-Hydroxybenzyl | Phenyl | 2,4,5-Trimethoxyphenyl | 659 | 659 |
| 270 | 4-Hydroxybenzyl | Phenyl | 3-Hydroxybenzyl | 599 | 599 |
| 271 | 4-Hydroxybenzyl | Phenyl | 1-Naphthylmethyl | 633 | 633 |
| 272 | 4-Hydroxybenzyl | Phenyl | Phenethyl | 597 | 597 |
| 273 | 4-Hydroxybenzyl | Phenyl | 3-Methoxyphenyl | 599 | 599 |
| 274 | 4-Hydroxybenzyl | Phenyl | N-Benzoylaminoethyl | 626 | 626 |
| 275 | 4-Hydroxybenzyl | Phenyl | Benzyl | 583 | 583 |
| 276 | 4-Hydroxybenzyl | Phenyl | 4-Nitrobenzyl | 628 | 628 |
| 277 | Cyclohexylmethyl | Phenyl | 4-Methoxybenzyl | 603 | 603 |
| 278 | Cyclohexylmethyl | Phenyl | 3,4-$Cl_2$-benzyl | 628 | 628 |
| 279 | Cyclohexylmethyl | Phenyl | 1-Naphthyl | 609 | 609 |
| 280 | Cyclohexylmethyl | Phenyl | Piperonyl | 603 | 603 |
| 281 | Cyclohexylmethyl | Phenyl | 2,4,5-Trimethoxyphenyl | 649 | 649 |
| 282 | Cyclohexylmethyl | Phenyl | 3-Hydroxybenzyl | 589 | 589 |
| 283 | Cyclohexylmethyl | Phenyl | 1-Naphthylmethyl | 623 | 623 |
| 284 | Cyclohexylmethyl | Phenyl | Phenethyl | 587 | 587 |
| 285 | Cyclohexylmethyl | Phenyl | 3-Methoxyphenyl | 589 | 589 |
| 286 | Cyclohexylmethyl | Phenyl | N-Benzoylaminoethyl | 616 | 616 |
| 287 | Cyclohexylmethyl | Phenyl | Benzyl | 573 | 573 |
| 288 | Cyclohexylmethyl | Phenyl | 4-Nitrobenzyl | 618 | 618 |
| 289 | Methyl | Benzyloxy | 4-Methoxybenzyl | 553 | 553 |
| 290 | Methyl | Benzyloxy | 3,4-$Cl_2$-benzyl | 577 | 577 |
| 291 | Methyl | Benzyloxy | 1-Naphthyl | 559 | 559 |
| 292 | Methyl | Benzyloxy | Piperonyl | 553 | 553 |
| 293 | Methyl | Benzyloxy | 2,4,5-Trimethoxyphenyl | 599 | 599 |
| 294 | Methyl | Benzyloxy | 2-Thienylmethyl | 539 | 539 |
| 295 | Methyl | Benzyloxy | 1-Naphthylmethyl | 573 | 573 |
| 296 | Methyl | Benzyloxy | Phenethyl | 537 | 537 |
| 297 | Methyl | Benzyloxy | 3-Methoxyphenyl | 539 | 539 |
| 298 | Methyl | Benzyloxy | N-Benzoylaminoethyl | 566 | 566 |
| 299 | Methyl | Benzyloxy | Benzyl | 523 | 523 |
| 300 | Methyl | Benzyloxy | 4-Nitrobenzyl | 568 | 568 |
| 301 | Isopropyl | Benzyloxy | 4-Methoxybenzyl | 581 | 581 |
| 302 | Isopropyl | Benzyloxy | 3,4-$Cl_2$-benzyl | 605 | 605 |
| 303 | Isopropyl | Benzyloxy | 1-Naphthyl | 587 | 587 |
| 304 | Isopropyl | Benzyloxy | Piperonyl | 581 | 581 |
| 305 | Isopropyl | Benzyloxy | 2,4,5-Trimethoxyphenyl | 627 | 627 |
| 306 | Isopropyl | Benzyloxy | 2-Thienylmethyl | 567 | 567 |
| 307 | Isopropyl | Benzyloxy | 1-Naphthylmethyl | 601 | 601 |
| 308 | Isopropyl | Benzyloxy | Phenethyl | 565 | 565 |
| 309 | Isopropyl | Benzyloxy | 3-Methoxyphenyl | 567 | 567 |
| 310 | Isopropyl | Benzyloxy | N-Benzoylaminoethyl | 594 | 594 |
| 311 | Isopropyl | Benzyloxy | Benzyl | 551 | 551 |

TABLE 2-continued

THE BETA-STRAND MIMETICS LIBRARY

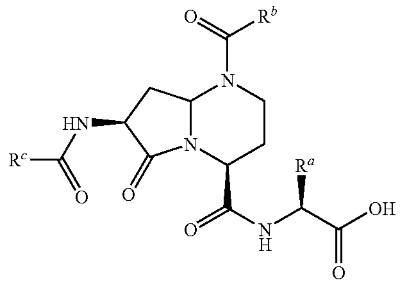

| No. | $R^a$ | $R^b$ | $R^c$ | Mol. Weight | M + H |
|---|---|---|---|---|---|
| 312 | Isopropyl | Benzyloxy | 4-Nitrobenzyl | 596 | 596 |
| 313 | Isobutyl | Benzyloxy | 4-Methoxybenzyl | 595 | 595 |
| 314 | Isobutyl | Benzyloxy | 3,4-$Cl_2$-benzyl | 620 | 620 |
| 315 | Isobutyl | Benzyloxy | 1-Naphthyl | 601 | 601 |
| 316 | Isobutyl | Benzyloxy | Piperonyl | 595 | 595 |
| 317 | Isobutyl | Benzyloxy | 2,4,5-Trimethoxyphenyl | 641 | 641 |
| 318 | Isobutyl | Benzyloxy | 2-Thienylmethyl | 581 | 581 |
| 319 | Isobutyl | Benzyloxy | 1-Naphthylmethyl | 615 | 615 |
| 320 | Isobutyl | Benzyloxy | Phenethyl | 579 | 579 |
| 321 | Isobutyl | Benzyloxy | 3-Methoxyphenyl | 581 | 581 |
| 322 | Isobutyl | Benzyloxy | N-Benzoylaminoethyl | 608 | 608 |
| 323 | Isobutyl | Benzyloxy | Benzyl | 565 | 565 |
| 324 | Isobutyl | Benzyloxy | 4-Nitrobenzyl | 610 | 610 |
| 325 | Benzyl | Benzyloxy | 4-Methoxybenzyl | 629 | 629 |
| 326 | Benzyl | Benzyloxy | 3,4-$Cl_2$-benzyl | 654 | 654 |
| 327 | Benzyl | Benzyloxy | 1-Naphthyl | 635 | 635 |
| 328 | Benzyl | Benzyloxy | Piperonyl | 629 | 629 |
| 329 | Benzyl | Benzyloxy | 2,4,5-Trimethoxyphenyl | 675 | 675 |
| 330 | Benzyl | Benzyloxy | 2-Thienylmethyl | 615 | 615 |
| 331 | Benzyl | Benzyloxy | 1-Naphthylrnethyl | 649 | 649 |
| 332 | Benzyl | Benzyloxy | Phenethyl | 613 | 613 |
| 333 | Benzyl | Benzyloxy | 3-Methoxyphenyl | 615 | 615 |
| 334 | Benzyl | Benzyloxy | N-Benzoylaminoethyl | 642 | 642 |
| 335 | Benzyl | Benzyloxy | Benzyl | 599 | 599 |
| 336 | Benzyl | Benzyloxy | 4-Nitrobenzyl | 644 | 644 |
| 337 | 2-Methylpropyl | Benzyloxy | 4-Methoxybenzyl | 595 | 595 |
| 338 | 2-Methylpropyl | Benzyloxy | 3,4-$Cl_2$-benzyl | 620 | 620 |
| 339 | 2-Methylpropyl | Benzyloxy | 1-Naphthyl | 601 | 601 |
| 340 | 2-Methylpropyl | Benzyloxy | Piperonyl | 595 | 595 |
| 341 | 2-Methylpropyl | Benzyloxy | 2,4,5-Trimethoxyphenyl | 641 | 641 |
| 342 | 2-Methylpropyl | Benzyloxy | 2-Thienylmethyl | 581 | 581 |
| 343 | 2-Methylpropyl | Benzyloxy | 1-Naphthylmethyl | 615 | 615 |
| 344 | 2-Methylpropyl | Benzyloxy | Phenethyl | 579 | 579 |
| 345 | 2-Methylpropyl | Benzyloxy | 3-Methoxyphenyl | 581 | 581 |
| 346 | 2-Methylpropyl | Benzyloxy | N-Benzoylaminoethyl | 608 | 608 |
| 347 | 2-Methylpropyl | Benzyloxy | Benzyl | 565 | 565 |
| 348 | 2-Methylpropyl | Benzyloxy | 4-Nitrobenzyl | 610 | 610 |
| 349 | Methylthioethyl | Benzyloxy | 4-Methoxybenzyl | 613 | 613 |
| 350 | Methylthioethyl | Benzyloxy | 3,4-$Cl_2$-benzyl | 638 | 638 |
| 351 | Methylthioethyl | Benzyloxy | 1-Naphthyl | 619 | 619 |
| 352 | Methylthioethyl | Benzyloxy | Piperonyl | 613 | 613 |
| 353 | Methylthioethyl | Benzyloxy | 2,4,5-Trimethoxyphenyl | 659 | 659 |
| 354 | Methylthioethyl | Benzyloxy | 2-Tthienylmethyl | 599 | 599 |
| 355 | Methylthioethyl | Benzyloxy | 1-Naphthylmethyl | 633 | 633 |
| 356 | Methylthioethyl | Benzyloxy | Phenethyl | 597 | 597 |
| 357 | Methylthioethyl | Benzyloxy | 3-Methoxyphenyl | 599 | 599 |
| 358 | Methylthioethyl | Benzyloxy | N-Benzoylaminoethyl | 626 | 626 |
| 359 | Methylthioethyl | Benzyloxy | Benzyl | 583 | 583 |
| 360 | Methylthioethyl | Benzyloxy | 4-Nitrobenzyl | 628 | 628 |
| 361 | 4-Hydroxybenzyl | Benzyloxy | 4-Methoxybenzyl | 645 | 645 |
| 362 | 4-Hydroxybenzyl | Benzyloxy | 3,4-$Cl_2$-benzyl | 670 | 670 |
| 363 | 4-Hydroxybenzyl | Benzyloxy | 1-Naphthyl | 651 | 651 |
| 364 | 4-Hydroxybenzyl | Benzyloxy | Piperonyl | 645 | 645 |
| 365 | 4-Hydroxybenzyl | Benzyloxy | 2,4,5-Trimethoxyphenyl | 691 | 691 |
| 366 | 4-Hydroxybenzyl | Benzyloxy | 2-Thienylmethyl | 631 | 631 |
| 367 | 4-Hydroxybenzyl | Benzyloxy | 1-Naphthylmethyl | 665 | 665 |
| 368 | 4-Hydroxybenzyl | Benzyloxy | Phenethyl | 629 | 629 |
| 369 | 4-Hydroxybenzyl | Benzyloxy | 3-Methoxyphenyl | 631 | 631 |

TABLE 2-continued

THE BETA-STRAND MIMETICS LIBRARY

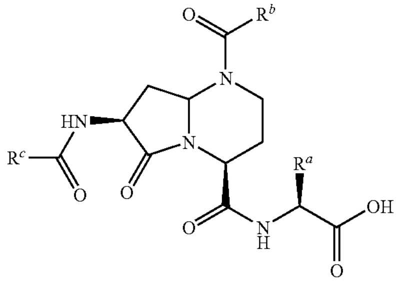

| No. | $R^a$ | $R^b$ | $R^c$ | Mol. Weight | M + H |
|---|---|---|---|---|---|
| 370 | 4-Hydroxybenzyl | Benzyloxy | N-Benzoylaminoethyl | 658 | 658 |
| 371 | 4-Hydroxybenzyl | Benzyloxy | Benzyl | 615 | 615 |
| 372 | 4-Hydroxybenzyl | Benzyloxy | 4-Nitrobenzyl | 660 | 660 |
| 373 | Cyclohexylmethyl | Benzyloxy | 4-Methoxybenzyl | 635 | 635 |
| 374 | Cyclohexylmethyl | Benzyloxy | 3,4-$Cl_2$-benzyl | 660 | 660 |
| 375 | Cyclohexylmethyl | Benzyloxy | 1-Naphthyl | 641 | 641 |
| 376 | Cyclohexylmethyl | Benzyloxy | Piperonyl | 635 | 635 |
| 377 | Cyclohexylmethyl | Benzyloxy | 2,4,5-Trimethoxyphenyl | 681 | 681 |
| 378 | Cyclohexylmethyl | Benzyloxy | 2-Thienylmethyl | 621 | 621 |
| 379 | Cyclohexylmethyl | Benzyloxy | 1-Naphthylmethyl | 655 | 655 |
| 380 | Cyclohexylmethyl | Benzyloxy | Phenethyl | 619 | 619 |
| 381 | Cyclohexylmethyl | Benzyloxy | 3-Methoxyphenyl | 621 | 621 |
| 382 | Cyclohexylmethyl | Benzyloxy | N-Benzoylaminoethyl | 648 | 648 |
| 383 | Cyclohexylmethyl | Benzyloxy | Benzyl | 605 | 605 |
| 384 | Cyclohexylmethyl | Benzyloxy | 4-Nitrobenzyl | 650 | 650 |
| 385 | Methyl | Methoxy | Acetoxymethyl | 422 | 422 |
| 386 | Methyl | Methoxy | 4-(2,5-Cl2pyridyl)methyl | 502 | 502 |
| 387 | Methyl | Methoxy | Chromen-2-one-3-methyl | 500 | 500 |
| 388 | Methyl | Methoxy | Methoxymethyl | 400 | 400 |
| 389 | Methyl | Methoxy | Pyran-2-one-5-methyl | 450 | 450 |
| 390 | Methyl | Methoxy | Ethyl | 384 | 384 |
| 391 | Methyl | Methoxy | 2-Ethyldecanyl | 510 | 510 |
| 392 | Methyl | Methoxy | Pyrazine-2-methyl | 434 | 434 |
| 393 | Methyl | Methoxy | 4-Pyridylmethyl | 433 | 433 |
| 394 | Methyl | Methoxy | 1-Butenyl | 410 | 410 |
| 395 | Methyl | Methoxy | 2-Nitro-5-Chlorophenyl | 511 | 511 |
| 396 | Methyl | Methoxy | Cyanomethyl | 395 | 395 |
| 397 | Isopropyl | Methoxy | Acetoxymethyl | 450 | 450 |
| 398 | Isopropyl | Methoxy | 4-(2,5-Cl2pyridyl)methyl | 530 | 530 |
| 399 | Isopropyl | Methoxy | Chromen-2-one-3-methyl | 528 | 528 |
| 400 | Isopropyl | Methoxy | Methoxymethyl | 428 | 428 |
| 401 | Isopropyl | Methoxy | Pyran-2-one-5-methyl | 478 | 478 |
| 402 | Isopropyl | Methoxy | Ethyl | 412 | 412 |
| 403 | Isopropyl | Methoxy | 2-Ethyldecanyl | 538 | 538 |
| 404 | Isopropyl | Methoxy | Pyrazine-2-methyl 462 | 462 | |
| 405 | Isopropyl | Methoxy | 4-Pyridylmethyl | 461 | 461 |
| 406 | Isopropyl | Methoxy | 1-Butenyl | 438 | 438 |
| 407 | Isopropyl | Methoxy | 2-Nitro-5-Chlorophenyl | 539 | 539 |
| 408 | Isopropyl | Methoxy | Cyanomethyl | 423 | 423 |
| 409 | Isobutyl | Methoxy | Acetoxymethyl | 464 | 464 |
| 410 | Isobutyl | Methoxy | 4-(2,5-Cl2pyridyl)methyl | 544 | 544 |
| 411 | Isobutyl | Methoxy | Chromen-2-one-3-methyl | 542 | 542 |
| 412 | Isobutyl | Methoxy | Methoxymethyl | 442 | 442 |
| 413 | Isobutyl | Methoxy | Pyran-2-one-5-methyl | 492 | 492 |
| 414 | Isobutyl | Methoxy | Ethyl | 426 | 426 |
| 415 | Isobutyl | Methoxy | 2-Ethyldecanyl | 552 | 552 |
| 416 | Isobutyl | Methoxy | Pyrazine-2-methyl | 476 | 476 |
| 417 | Isobutyl | Methoxy | 4-Pyridylmethyl | 475 | 475 |
| 418 | Isobutyl | Methoxy | 1-Butenyl | 452 | 452 |
| 419 | Isobutyl | Methoxy | 2-Nitro-5-Chlorophenyl | 553 | 553 |
| 420 | Isobutyl | Methoxy | Cyanomethyl | 437 | 437 |
| 421 | Benzyl | Methoxy | Acetoxymethyl | 498 | 498 |
| 422 | Benzyl | Methoxy | 4(2,5-Cl2pyridyl)methyl | 578 | 578 |
| 423 | Benzyl | Methoxy | Chromen-2-one-3-methyl | 576 | 576 |

TABLE 2-continued

THE BETA-STRAND MIMETICS LIBRARY

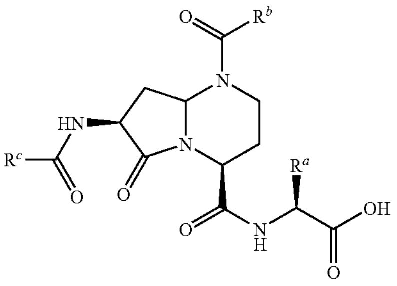

| No. | $R^a$ | $R^b$ | $R^c$ | Mol. Weight | M + H |
|---|---|---|---|---|---|
| 424 | Benzyl | Methoxy | Methoxymethyl | 476 | 476 |
| 425 | Benzyl | Methoxy | Pyran-2-one-5-methyl | 526 | 526 |
| 426 | Benzyl | Methoxy | Ethyl | 460 | 460 |
| 427 | Benzyl | Methoxy | 2-Ethyldecanyl | 586 | 586 |
| 428 | Benzyl | Methoxy | Pyrazine-2-methyl | 510 | 510 |
| 429 | Benzyl | Methoxy | 4-Pyridylmethyl | 509 | 509 |
| 430 | Benzyl | Methoxy | 1-Butenyl | 486 | 486 |
| 431 | Benzyl | Methoxy | 2-Nitro-5-Chlorophenyl | 587 | 587 |
| 432 | Benzyl | Methoxy | Cyanomethyl | 471 | 471 |
| 433 | 2-Methylpropyl | Methoxy | Acetoxymethyl | 464 | 464 |
| 434 | 2-Methylpropyl | Methoxy | 4-(2,5-Cl2pyridyl)methyl | 544 | 544 |
| 435 | 2-Methyipropyl | Methoxy | Chromen-2-one-3-methyl | 542 | 542 |
| 436 | 2-Methylpropyl | Methoxy | Methoxymethyl | 442 | 442 |
| 437 | 2-Methylpropyl | Methoxy | Pyran-2-one-5-methyl | 492 | 492 |
| 438 | 2-Methylpropyl | Methoxy | Ethyl | 426 | 426 |
| 439 | 2-Methylpropyl | Methoxy | 2-Ethyldecanyl | 552 | 552 |
| 440 | 2-Methylpropyl | Methoxy | Pyrazine-2-methyl | 476 | 476 |
| 441 | 2-Methylpropyl | Methoxy | 4-Pyridylmethyl | 475 | 475 |
| 442 | 2-Methylpropyl | Methoxy | 1-Butenyl | 452 | 452 |
| 443 | 2-Methylpropyl | Methoxy | 2-Nitro-5-Chlorophenyl | 553 | 553 |
| 444 | 2-Methylpropyl | Methoxy | Cyanomethyl | 437 | 437 |
| 445 | Methylthioethyl | Methoxy | Acetoxymethyl | 482 | 482 |
| 446 | Methylthioethyl | Methoxy | 4-(2,5-Cl2pyridyl)methyl | 562 | 562 |
| 447 | Methylthioethyl | Methoxy | Chromen-2-one-3-methyl | 560 | 560 |
| 448 | Methylthioethyl | Methoxy | Methoxymethyl | 460 | 460 |
| 449 | Methylthioethyl | Methoxy | Pyran-2-one-5-methyl | 510 | 510 |
| 450 | Methylthioethyl | Methoxy | Ethyl | 444 | 444 |
| 451 | Methylthioethyl | Methoxy | 2-Ethyldecanyl | 570 | 570 |
| 452 | Methylthioethyl | Methoxy | Pyrazine-2-methyl | 494 | 494 |
| 453 | Methylthioethyl | Methoxy | 4-Pyridylmethyl | 493 | 493 |
| 454 | Methylthioethyl | Methoxy | 1 -Butenyl | 470 | 470 |
| 455 | Methylthioethyl | Methoxy | 2-Nitro-5-Chlorophenyl | 571 | 571 |
| 456 | Methylthioethyl | Methoxy | Cyanomethyl | 455 | 455 |
| 457 | 4-Hydroxybenzyl | Methoxy | Acetoxymethyl | 514 | 514 |
| 458 | 4-Hydroxybenzyl | Methoxy | 4-(2,5-Cl2pyridyl)methyl | 594 | 594 |
| 459 | 4-Hydroxybenzyl | Methoxy | Chromen-2-one-3-methyl | 592 | 592 |
| 460 | 4-Hydroxybenzyl | Methoxy | Methoxymethyl | 492 | 492 |
| 461 | 4-Hydroxybenzyl | Methoxy | Pyran-2-one-5-methyl | 542 | 542 |
| 462 | 4-Hydroxybenzyl | Methoxy | Ethyl | 476 | 476 |
| 463 | 4-Hydroxybenzyl | Methoxy | 2-Ethyldecanyl | 602 | 602 |
| 464 | 4-Hydroxybenzyl | Methoxy | Pyrazine-2-methyl | 526 | 526 |
| 465 | 4-Hydroxybenzyl | Methoxy | 4-Pyridylmethyl | 525 | 525 |
| 466 | 4-Hydroxybenzyl | Methoxy | 1-Butenyl | 502 | 502 |
| 467 | 4-Hydroxybenzyl | Methoxy | 2-Nitro-5-Chlorophenyl | 603 | 603 |
| 468 | 4-Hydroxybenzyl | Methoxy | Cyanomethyl | 487 | 487 |
| 469 | 2-Hydroxyethyl | Methoxy | Acetoxymethyl | 452 | 452 |
| 470 | 2-Hydroxyethyl | Methoxy | 4-(2,5-Cl2pyridyl)methyl | 532 | 532 |
| 471 | 2-Hydroxyethyl | Methoxy | Chromen-2-one-3-methyl | 530 | 530 |
| 472 | 2-Hydroxyethyl | Methoxy | Methoxymethyl | 430 | 430 |
| 473 | 2-Hydroxyethyl | Methoxy | Pyran-2-one-5-methyl | 480 | 480 |
| 474 | 2-Hydroxyethyl | Methoxy | Ethyl | 414 | 414 |
| 475 | 2-Hydroxyethyl | Methoxy | 2-Ethyldecanyl | 540 | 540 |
| 476 | 2-Hydroxyethyl | Methoxy | Pyrazine-2-methyl | 464 | 464 |
| 477 | 2-Hydroxyethyl | Methoxy | 4-Pyridylmethyl | 463 | 463 |

TABLE 2-continued

THE BETA-STRAND MIMETICS LIBRARY

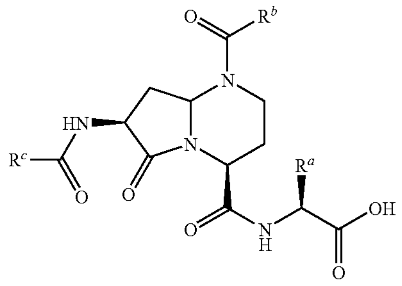

| No. | $R^a$ | $R^b$ | $R^c$ | Mol. Weight | M + H |
|---|---|---|---|---|---|
| 478 | 2-Hydroxyethyl | Methoxy | 1-Butenyl | 440 | 440 |
| 479 | 2-Hydroxyethyl | Methoxy | 2-Nitro-5-Chlorophenyl | 541 | 541 |
| 480 | 2-Hydroxyethyl | Methoxy | Cyanomethyl | 425 | 425 |
| 481 | Methyl | Phenyl | 2,4-Pentadienyl | 469 | 469 |
| 482 | Methyl | Phenyl | 4-(2,5-Cl2pyridyl)methyl | 548 | 548 |
| 483 | Methyl | Phenyl | Chromen-2-one-3-methyl | 547 | 547 |
| 484 | Methyl | Phenyl | Methoxymethyl | 446 | 446 |
| 485 | Methyl | Phenyl | Pyran-2-one-5-methyl | 496 | 496 |
| 486 | Methyl | Phenyl | Ethyl | 430 | 430 |
| 487 | Methyl | Phenyl | 2-Ethyldecanyl | 501 | 501 |
| 488 | Methyl | Phenyl | Pyrazine-2-methyl | 480 | 480 |
| 489 | Methyl | Phenyl | 4-Pyridylmethyl | 479 | 479 |
| 490 | Methyl | Phenyl | 1-Butenyl | 457 | 457 |
| 491 | Methyl | Phenyl | 2-Nitro-5-Chlorophenyl | 558 | 558 |
| 492 | Methyl | Phenyl | Cyanomethyl | 441 | 441 |
| 493 | Isopropyl | Phenyl | 2,4-Pentadienyl | 497 | 497 |
| 494 | Isopropyl | Phenyl | 4-(2,5-Cl2pyridyl)methyl | 576 | 576 |
| 495 | Isopropyl | Phenyl | Chromen-2-one-3-methyl | 575 | 575 |
| 496 | Isopropyl | Phenyl | Methoxymethyl | 475 | 475 |
| 497 | Isopropyl | Phenyl | Pyran-2-one-5-methyl | 525 | 525 |
| 498 | Isopropyl | Phenyl | Ethyl | 459 | 459 |
| 499 | Isopropyl | Phenyl | 2-Ethyldecanyl | 529 | 529 |
| 500 | Isopropyl | Phenyl | Pyrazine-2-methyl | 509 | 509 |
| 501 | Isopropyl | Phenyl | 4-Pyridylmethyl | 508 | 508 |
| 502 | Isopropyl | Phenyl | 1-Butenyl | 485 | 485 |
| 503 | Isopropyl | Phenyl | 2-Nitro-5-Chlorophenyl | 586 | 586 |
| 504 | Isopropyl | Phenyl | Cyanomethyl | 470 | 470 |
| 505 | Isobutyl | Phenyl | 2,4-Pentadienyl | 511 | 511 |
| 506 | Isobutyl | Phenyl | 4-(2,5-Cl2pyridyl)methyl | 590 | 590 |
| 507 | Isobutyl | Phenyl | Chromen-2-one-3-methyl | 589 | 589 |
| 508 | Isobutyl | Phenyl | Methoxymethyl | 489 | 489 |
| 509 | Isobutyl | Phenyl | Pyran-2-one-5-methyl | 539 | 539 |
| 510 | Isobutyl | Phenyl | Ethyl | 473 | 473 |
| 511 | Isobutyl | Phenyl | 2-Ethyldecanyl | 543 | 543 |
| 512 | Isobutyl | Phenyl | Pyrazine-2-methyl | 523 | 523 |
| 513 | Isobutyl | Phenyl | 4-Pyridylmethyl | 522 | 522 |
| 514 | Isobutyl | Phenyl | 1-Butenyl | 499 | 499 |
| 515 | Isobutyl | Phenyl | 2-Nitro-5-Chlorophenyl | 600 | 600 |
| 516 | Isobutyl | Phenyl | Cyanomethyl | 484 | 484 |
| 517 | Benzyl | Phenyl | 2,4-Pentadienyl | 545 | 545 |
| 518 | Benzyl | Phenyl | 4-(2,5-Cl2pyridyl)methyl | 624 | 624 |
| 519 | Benzyl | Phenyl | Chromen-2-one-3-methyl | 623 | 623 |
| 520 | Benzyl | Phenyl | Methoxymethyl | 523 | 523 |
| 521 | Benzyl | Phenyl | Pyran-2-one-5-methyl | 573 | 573 |
| 522 | Benzyl | Phenyl | Ethyl | 507 | 507 |
| 523 | Benzyl | Phenyl | 2-Ethyldecanyl | 577 | 577 |
| 524 | Benzyl | Phenyl | Pyrazine-2-methyl | 557 | 557 |
| 525 | Benzyl | Phenyl | 4-Pyridylmethyl | 556 | 556 |
| 526 | Benzyl | Phenyl | 1-Butenyl | 533 | 533 |
| 527 | Benzyl | Phenyl | 2-Nitro-5-Chlorophenyl | 634 | 634 |
| 528 | Benzyl | Phenyl | Cyanomethyl | 518 | 518 |
| 529 | 2-Methylpropyl | Phenyl | 2,4-Pentadienyl | 511 | 511 |
| 530 | 2-Methylpropyl | Phenyl | 4-(2,5-$Cl_2$pyridyl)methyl | 590 | 590 |

TABLE 2-continued

THE BETA-STRAND MIMETICS LIBRARY

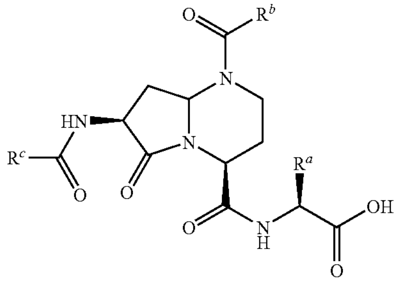

| No. | $R^a$ | $R^b$ | $R^c$ | Mol. Weight | M + H |
|---|---|---|---|---|---|
| 531 | 2-Methylpropyl | Phenyl | Chromen-2-one-3-methyl | 589 | 589 |
| 532 | 2-Methylpropyl | Phenyl | Methoxymethyl | 489 | 489 |
| 533 | 2-Methylpropyl | Phenyl | Pyran-2-one-5-methyl | 539 | 539 |
| 534 | 2-Methylpropyl | Phenyl | Ethyl | 473 | 473 |
| 535 | 2-Methylpropyl | Phenyl | 2-Ethyldecanyl | 543 | 543 |
| 536 | 2-Methylpropyl | Phenyl | Pyrazine-2-methyl | 523 | 523 |
| 537 | 2-Methylpropyl | Phenyl | 4-Pyridylmethyl | 522 | 522 |
| 538 | 2-Methylpropyl | Phenyl | 1-Butenyl | 499 | 499 |
| 539 | 2-Methylpropyl | Phenyl | 2-Nitro-5-Chlorophenyl | 600 | 600 |
| 540 | 2-Methylpropyl | Phenyl | Cyanomethyl | 484 | 484 |
| 541 | Methylthioethyl | Phenyl | 2,4-Pentadienyl | 529 | 529 |
| 542 | Methylthioethyl | Phenyl | 4-(2,5-Cl2pyridyl)methyl | 609 | 609 |
| 543 | Methylthioethyl | Phenyl | Chromen-2-one-3-methyl | 607 | 607 |
| 544 | Methylthioethyl | Phenyl | Methoxymethyl | 507 | 507 |
| 545 | Methylthioethyl | Phenyl | Pyran-2-one-5-methyl | 557 | 557 |
| 546 | Methylthioethyl | Phenyl | Ethyl | 491 | 491 |
| 547 | Methyithioethyl | Phenyl | 2-Ethyldecanyl | 561 | 561 |
| 548 | Methylthioethyl | Phenyl | Pyrazine-2-methyl | 541 | 541 |
| 549 | Methylthioethyl | Phenyl | 4-Pyridylmethyl | 540 | 540 |
| 550 | Methylthioethyl | Phenyl | 1-Butenyl | 517 | 517 |
| 551 | Methyithioethyl | Phenyl | 2-Nitro-5-Chlorophenyl | 618 | 618 |
| 552 | Methylthioethyl | Phenyl | Cyanomethyl | 502 | 502 |
| 553 | 4-Hydroxybenzyl | Phenyl | 2,4-Pentadienyl | 561 | 561 |
| 554 | 4-Hydroxybenzyl | Phenyl | 4-(2,5-Cl2pyridyl)methyl | 640 | 640 |
| 555 | 4-Hydroxybenzyl | Phenyl | Chromen-2-one-3-methyl | 639 | 639 |
| 556 | 4-Hydroxybenzyl | Phenyl | Methoxymethyl | 539 | 539 |
| 557 | 4-Hydroxybenzyl | Phenyl | Pyran-2-one-5-methyl | 589 | 589 |
| 558 | 4-Hydroxybenzyl | Phenyl | Ethyl | 523 | 523 |
| 559 | 4-Hydroxybenzyl | Phenyl | 2-Ethyldecanyl | 593 | 593 |
| 560 | 4-Hydroxybenzyl | Phenyl | Pyrazine-2-methyl | 573 | 573 |
| 561 | 4-Hydroxybenzyl | Phenyl | 4-Pyridylmethyl | 572 | 572 |
| 562 | 4-Hydroxybenzyl | Phenyl | 1-Butenyl | 549 | 549 |
| 563 | 4-Hydroxybenzyl | Phenyl | 2-Nitro-5-Chlorophenyl | 650 | 650 |
| 564 | 4-Hydroxybenzyl | Phenyl | Cyanomethyl | 534 | 534 |
| 565 | 2-Hydroxyethyl | Phenyl | 2,4-Pentadienyl | 499 | 499 |
| 566 | 2-Hydroxyethyl | Phenyl | 4-(2,5-Cl2pyridyl)methyl | 578 | 578 |
| 567 | 2-Hydroxyethyl | Phenyl | Chromen-2-one-3-methyl | 577 | 577 |
| 568 | 2-Hydroxyethyl | Phenyl | Methoxymethyl | 476 | 476 |
| 569 | 2-Hydroxyethyl | Phenyl | Pyran-2-one-5-methyl | 527 | 527 |
| 570 | 2-Hydroxyethyl | Phenyl | Ethyl | 460 | 460 |
| 571 | 2-Hydroxyethyl | Phenyl | 2-Ethyldecanyl | 531 | 531 |
| 572 | 2-Hydroxyethyl | Phenyl | Pyrazine-2-methyl | 511 | 511 |
| 573 | 2-Hydroxyethyl | Phenyl | 4-Pyridylmethyl | 510 | 510 |
| 574 | 2-Hydroxyethyl | Phenyl | 1-Butenyl | 487 | 487 |
| 575 | 2-Hydroxyethyl | Phenyl | 2-Nitro-5-Chlorophenyl | 588 | 588 |
| 576 | 2-Hydroxyethyl | Phenyl | Cyanomethyl | 471 | 471 |
| 577 | Methyl | Methyl | 2,4-Pentadienyl | 406 | 406 |
| 578 | Methyl | Methyl | 4-(2,5-Cl2pyridyl)methyl | 486 | 486 |
| 579 | Methyl | Methyl | Chromen-2-one-3-methyl | 484 | 484 |
| 580 | Methyl | Methyl | Methoxymethyl | 384 | 384 |
| 581 | Methyl | Methyl | Pyran-2-one-5-methyl | 434 | 434 |
| 582 | Methyl | Methyl | Ethyl | 368 | 368 |
| 583 | Methyl | Methyl | 2-Ethyldecanyl | 438 | 438 |

TABLE 2-continued

THE BETA-STRAND MIMETICS LIBRARY

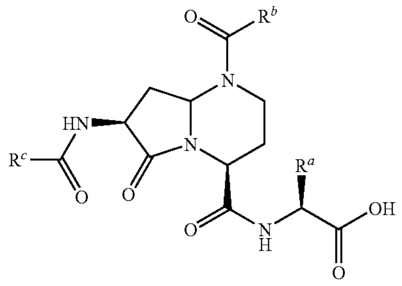

| No. | $R^a$ | $R^b$ | $R^c$ | Mol. Weight | M + H |
|---|---|---|---|---|---|
| 584 | Methyl | Methyl | Pyrazine-2-methyl | 418 | 418 |
| 585 | Methyl | Methyl | 4-Pyridylmethyl | 417 | 417 |
| 586 | Methyl | Methyl | 1-Butenyl | 394 | 394 |
| 587 | Methyl | Methyl | 2-Nitro-5-Chlorophenyl | 495 | 495 |
| 588 | Methyl | Methyl | Cyanomethyl | 434 | 434 |
| 589 | Isopropyl | Methyl | 2,4-Pentadienyl | 434 | 434 |
| 590 | Isopropyl | Methyl | 4-(2,5-Cl2pyridyl)methyl | 514 | 514 |
| 591 | Isopropyl | Methyl | Chromen-2-one-3-methyl | 512 | 512 |
| 592 | Isopropyl | Methyl | Methoxytmethyl | 412 | 412 |
| 593 | Isopropyl | Methyl | Pyran-2-one-5-methyl | 462 | 462 |
| 594 | Isopropyl | Methyl | Ethyl | 396 | 396 |
| 595 | Isopropyl | Methyl | 2-Ethyldecanyl | 466 | 466 |
| 596 | Isopropyl | Methyl | Pyrazine-2-methyl | 446 | 446 |
| 597 | Isopropyl | Methyl | 4-Pyridylmethyl | 445 | 445 |
| 598 | Isopropyl | Methyl | 1-Butenyl | 422 | 422 |
| 599 | Isopropyl | Methyl | 2-Nitro-5-Chlorophenyl | 523 | 523 |
| 600 | Isopropyl | Methyl | Cyanomethyl | 462 | 462 |
| 601 | Isobutyl | Methyl | 2,4-Pentadienyl | 448 | 448 |
| 602 | Isobutyl | Methyl | 4-(2,5-Cl2pyridyl)methyl | 528 | 528 |
| 603 | Isobutyl | Methyl | Chromen-2-one-3-methyl | 526 | 526 |
| 604 | Isobutyl | Methyl | Methoxymethyl | 426 | 426 |
| 605 | Isobutyl | Methyl | Pyran-2-one-5-methyl | 476 | 476 |
| 606 | Isobutyl | Methyl | Ethyl | 410 | 410 |
| 607 | Isobutyl | Methyl | 2-Ethyldecanyl | 480 | 480 |
| 608 | Isobutyl | Methyl | Pyrazine-2-methyl | 460 | 460 |
| 609 | Isobutyl | Methyl | 4-Pyridylmethyl | 459 | 459 |
| 610 | Isobutyl | Methyl | 1-Butenyl | 436 | 436 |
| 611 | Isobutyl | Methyl | 2-Nitro-5-Chlorophenyl | 537 | 537 |
| 612 | Isobutyl | Methyl | Cyanomethyl | 476 | 476 |
| 613 | Benzyl | Methyl | 2,4-Pentadienyl | 482 | 482 |
| 614 | Benzyl | Methyl | 4-(2,5-Cl2pyridyl)methyl | 562 | 562 |
| 615 | BenzyI | Methyl | Chromen-2-one-3-methyl | 560 | 560 |
| 616 | Benzyl | Methyl | Methoxyniethyl | 460 | 460 |
| 617 | Benzyl | Methyl | Pyran-2-one-5-methyl | 510 | 510 |
| 618 | Benzyl | Methyl | Ethyl | 444 | 444 |
| 619 | Benzyl | Methyl | 2-Ethyldecanyl | 514 | 514 |
| 620 | Benzyl | Methyl | Pyrazine-2-methyl | 494 | 494 |
| 621 | Benzyl | Methyl | 4-Pyridylmethyl | 493 | 493 |
| 622 | Benzyl | Methyl | 1-Butenyl | 470 | 470 |
| 623 | Benzyl | Methyl | 2-Nitro-5-Chlorophenyl | 571 | 571 |
| 624 | Benzyl | Methyl | Cyanomethyl | 510 | 510 |
| 625 | 2-Methylpropyl | Methyl | 2,4-Pentadienyl | 448 | 448 |
| 626 | 2-Methylpropyl | Methyl | 4-(2,5-Cl2pyridyl)methyl | 528 | 528 |
| 627 | 2-Methylpropyl | Methyl | Chromen-2-one-3-methyl | 526 | 526 |
| 628 | 2-Methylpropyl | Methyl | Methoxymethyl | 426 | 426 |
| 629 | 2-Methylpropyl | Methyl | Pyran-2-one-5-methyl | 476 | 476 |
| 630 | 2-Methylpropyl | Methyl | Ethyl | 410 | 410 |
| 631 | 2-Methylpropyl | Methyl | 2-Ethyldecanyl | 480 | 480 |
| 632 | 2-Methylpropyl | Methyl | Pyrazine-2-methyl | 460 | 460 |
| 633 | 2-Methylpropyl | Methyl | 4-Pyridylmethyl | 459 | 459 |
| 634 | 2-Methylpropyl | Methyl | 1-Butenyl | 436 | 436 |
| 635 | 2-Methylpropyl | Methyl | 2-Nitro-5-Chlorophenyl | 537 | 537 |
| 636 | 2-Methylpropyl | Methyl | Cyanomethyl | 476 | 476 |
| 637 | Methylthioethyl | Methyl | 2,4-Pentadienyl | 466 | 466 |

TABLE 2-continued

THE BETA-STRAND MIMETICS LIBRARY

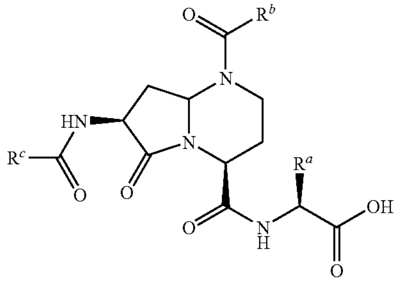

| No. | $R^a$ | $R^b$ | $R^c$ | Mol. Weight | M + H |
|---|---|---|---|---|---|
| 638 | Methylthioethyl | Methyl | 4-(2,5-Cl2pyridyl)methyl | 546 | 546 |
| 639 | Methylthioethyl | Methyl | Chromen-2-one-3-methyl | 544 | 544 |
| 640 | Methylthioethyl | Methyl | Methoxymethyl | 444 | 444 |
| 641 | Methylthioethyl | Methyl | Pyran-2-one-5-methyl | 494 | 494 |
| 642 | Methylthioethyl | Methyl | Ethyl | 428 | 428 |
| 643 | Methylthioethyl | Methyl | 2-Ethyldecanyl | 498 | 498 |
| 644 | Methylthioethyl | Methyl | Pyrazine-2-methyl | 478 | 478 |
| 645 | Methylthioethyl | Methyl | 4-Pyridylmethyl | 477 | 477 |
| 646 | Methylthioethyl | Methyl | 1-Butenyl | 454 | 454 |
| 647 | Methylthioethyl | Methyl | 2-Nitro-5-Chlorophenyl | 555 | 555 |
| 648 | Methylthioethyl | Methyl | Cyanomethyl | 494 | 494 |
| 649 | 4-Hydroxybenzyl | Methyl | 2,4-Pentadienyl | 498 | 498 |
| 650 | 4-Hydroxybenzyl | Methyl | 4-(2,5-Cl2pyridyl)methyl | 578 | 578 |
| 651 | 4-Hydroxybenzyl | Methyl | Chromen-2-one-3-methyl | 576 | 576 |
| 652 | 4-Hydroxybenzyl | Methyl | Methoxymethyl | 476 | 476 |
| 653 | 4-Hydroxybenzyl | Methyl | Pyran-2-one-5-methyl | 526 | 526 |
| 654 | 4-Hydroxybenzyl | Methyl | Ethyl | 460 | 460 |
| 655 | 4-Hydroxybenzyl | Methyl | 2-Ethyldecanyl | 530 | 530 |
| 656 | 4-Hydroxybenzyl | Methyl | Pyrazine-2-methyl | 510 | 510 |
| 657 | 4-Hydroxybenzyl | Methyl | 4-Pyridylmethyl | 509 | 509 |
| 658 | 4-Hydroxybenzyl | Methyl | 1-Butenyl | 486 | 486 |
| 659 | 4-Hydroxybenzyl | Methyl | 2-Nitro-5-Chlorophenyl | 587 | 587 |
| 660 | 4-Hydroxybenzyl | Methyl | Cyanomethyl | 526 | 526 |
| 661 | 2-Hydroxyethyl | Methyl | 2,4-Pentadienyl | 436 | 436 |
| 662 | 2-Hydroxyethyl | Methyl | 4-(2,5-Cl2pyridyl)methyl | 516 | 516 |
| 663 | 2-Hydroxyethyl | Methyl | Chromen-2-one-3-methyl | 514 | 514 |
| 664 | 2-Hydroxyethyl | Methyl | Methoxymethyl | 414 | 414 |
| 665 | 2-Hydroxyethyl | Methyl | Pyran-2-one-5-methyl | 464 | 464 |
| 666 | 2-Hydroxyethyl | Methyl | Ethyl | 398 | 398 |
| 667 | 2-Hydroxyethyl | Methyl | 2-Ethyldecanyl | 468 | 468 |
| 668 | 2-Hydroxyethyl | Methyl | Pyrazine-2-methyl | 448 | 448 |
| 669 | 2-Hydroxyethyl | Methyl | 4-Pyridylmethyl | 447 | 447 |
| 670 | 2-Hydroxyethyl | Methyl | 1-Butenyl | 424 | 424 |
| 671 | 2-Hydroxyethyl | Methyl | 2-Nitro-5-Chlorophenyl | 525 | 525 |
| 672 | 2-Hydroxyethyl | Methyl | Cyanomethyl | 464 | 464 |
| 673 | Cyclohexylmethyl | Methoxy | 4-Methoxybenzyl | 559 | 559 |
| 674 | 4-Phenylbenzyl | Methoxy | 4-Methoxybenzyl | 629 | 629 |
| 675 | 4-$NO_2$-benzyl | Methoxy | 4-Methoxybenzyl | 598 | 598 |
| 676 | 3,4-$Cl_2$-benzyl | Methoxy | 4-Methoxybenzyl | 621 | 621 |
| 677 | Cyclopentyl(spiro) | Methoxy | 4-Methoxybenzyl | 531 | 531 |
| 678 | 4-Methylbenzyl | Methoxy | 4-Methoxybenzyl | 567 | 567 |
| 679 | 1-Naphthylmethyl | Methoxy | 4-Methoxybenzyl | 603 | 603 |
| 680 | 4-F-benzyl | Methoxy | 4-Methoxybenzyl | 571 | 571 |
| 681 | 3,4-$F_2$-Benzyl | Methoxy | 4-Methoxybenzyl | 589 | 589 |
| 682 | Cyclohexyl | Methoxy | 4-Methoxybenzyl | 545 | 545 |
| 683 | 2-Cl-benzyl | Methoxy | 4-Methoxybenzyl | 587 | 587 |
| 684 | 4-Cl-benzyl | Methoxy | 4-Methoxybenzyl | 587 | 587 |
| 685 | Cyclohexylmethyl | Methoxy | 3,4-$Cl_2$-phenyl | 583 | 583 |
| 686 | 4-Phenylbenzyl | Methoxy | 3,4-$Cl_2$-phenyl | 654 | 654 |
| 687 | 4-$NO_2$-benzyl | Methoxy | 3,4-$Cl_2$-phenyl | 622 | 622 |
| 688 | 3,4-$Cl_2$-benzyl | Methoxy | 3,4-$Cl_2$-phenyl | 646 | 646 |
| 689 | Cyclopentyl(spiro) | Methoxy | 3,4-$Cl_2$-phenyl | 555 | 555 |
| 690 | 4-Methylbenzyl | Methoxy | 3,4-$Cl_2$-phenyl | 591 | 591 |
| 691 | 1-Naphthylmethyl | Methoxy | 3,4-$Cl_2$-phenyl | 627 | 627 |
| 692 | 4-F-benzyl | Methoxy | 3,4-$Cl_2$-phenyl | 595 | 595 |

TABLE 2-continued

THE BETA-STRAND MIMETICS LIBRARY

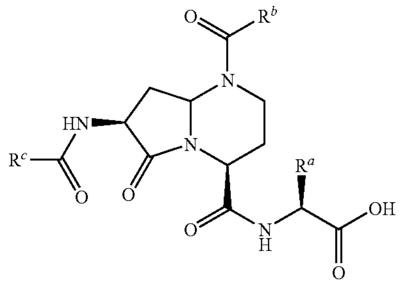

| No. | $R^a$ | $R^b$ | $R^c$ | Mol. Weight | M + H |
|---|---|---|---|---|---|
| 693 | 3,4-$F_2$-Benzyl | Methoxy | 3,4-$Cl_2$-phenyl | 613 | 613 |
| 694 | Cyclohexyl | Methoxy | 3,4-$Cl_2$-phenyl | 569 | 569 |
| 695 | 2-Cl-benzyl | Methoxy | 3,4-$Cl_2$-phenyl | 612 | 612 |
| 696 | 4-Cl-benzyl | Methoxy | 3,4-$Cl_2$-phenyl | 612 | 612 |
| 697 | Cyclohexylmethyl | Methoxy | 1-Naphthyl | 565 | 565 |
| 698 | 4-Phenylbenzyl | Methoxy | 1-Naphthyl | 635 | 635 |
| 699 | 4-$NO_2$-benzyl | Methoxy | 1-Naphthyl | 604 | 604 |
| 700 | 3,4-$Cl_2$-benzyl | Methoxy | 1-Naphthyl | 627 | 627 |
| 701 | Cyclopentyl(spiro) | Methoxy | 1-Naphthyl | 537 | 537 |
| 702 | 4-Methylbenzyl | Methoxy | 1-Naphthyl | 573 | 573 |
| 703 | 1-Naphthylmethyl | Methoxy | 1-Naphthyl | 609 | 609 |
| 704 | 4-F-benzyl | Methoxy | 1-Naphthyl | 577 | 577 |
| 705 | 3,4-$F_2$-Benzyl | Methoxy | 1-Naphthyl | 595 | 595 |
| 706 | Cyclohexyl | Methoxy | 1-Naphthyl | 551 | 551 |
| 707 | 2-Cl-benzyl | Methoxy | 1-Naphthyl | 593 | 593 |
| 708 | 4-Cl-benzyl | Methoxy | 1-Naphthyl | 593 | 593 |
| 709 | Cyclohexylmethyl | Methoxy | Piperonyl | 559 | 559 |
| 710 | 4-Phenylbenzyl | Methoxy | Piperonyl | 629 | 629 |
| 711 | 4-$NO_2$-benzyl | Methoxy | Piperonyl | 598 | 598 |
| 712 | 3,4-$Cl_2$-benzyl | Methoxy | Piperonyl | 621 | 621 |
| 713 | Cyclopentyl(spiro) | Methoxy | Piperonyl | 531 | 531 |
| 714 | 4-Methylbenzyl | Methoxy | Piperonyl | 567 | 567 |
| 715 | 1-Naphthylmethyl | Methoxy | Piperonyl | 603 | 603 |
| 716 | 4-F-benzyl | Methoxy | Piperonyl | 571 | 571 |
| 717 | 3,4-$F_2$-Benzyl | Methoxy | Piperonyl | 589 | 589 |
| 718 | Cyclohexyl | Methoxy | Piperonyl | 545 | 545 |
| 719 | 2-Cl-benzyl | Methoxy | Piperonyl | 587 | 587 |
| 720 | 4-Cl-benzyl | Methoxy | Piperonyl | 587 | 587 |
| 721 | Cyclohexylmethyl | Methoxy | 2,4,5-Trimethoxyphenyl | 605 | 605 |
| 722 | 4-Phenylbenzyl | Methoxy | 2,4,5-Trimethoxyphenyl | 675 | 675 |
| 723 | 4-$NO_2$-benzyl | Methoxy | 2,4,5-Trimethoxyphenyl | 644 | 644 |
| 724 | 3,4-$Cl_2$-benzyl | Methoxy | 2,4,5-Trimethoxyphenyl | 668 | 668 |
| 725 | Cyclopentyl(spiro) | Methoxy | 2,4,5-Trimethoxyphenyl | 577 | 577 |
| 726 | 4-Methylbenzyl | Methoxy | 2,4,5-Trimethoxyphenyl | 613 | 613 |
| 727 | 1-Naphthylmethyl | Methoxy | 2,4,5-Trimethoxyphenyl | 649 | 649 |
| 728 | 4-F-benzyl | Methoxy | 2,4,5-Trimethoxyphenyl | 617 | 617 |
| 729 | 3,4-$F_2$-Benzyl | Methoxy | 2,4,5-Trimethoxyphenyl | 635 | 635 |
| 730 | Cyclohexyl | Methoxy | 2,4,5-Trimethoxyphenyl | 591 | 591 |
| 731 | 2-Cl-benzyl | Methoxy | 2,4,5-Trimethoxyphenyl | 633 | 633 |
| 732 | 4-Cl-benzyl | Methoxy | 2,4,5-Trimethoxyphenyl | 633 | 633 |
| 733 | Cyclohexylmethyl | Methoxy | 3-Hydroxybenzyl | 545 | 545 |
| 734 | 4-Phenylbenzyl | Methoxy | 3-Hydroxybenzyl | 615 | 615 |
| 735 | 4-$NO_2$-benzyl | Methoxy | 3-Hydroxybenzyl | 584 | 584 |
| 736 | 3,4-$Cl_2$-benzyl | Methoxy | 3-Hydroxybenzyl | 607 | 607 |
| 737 | Cyclopentyl(spiro) | Methoxy | 3-Hydroxybenzyl | 517 | 517 |
| 738 | 4-Methylbenzyl | Methoxy | 3-Hydroxybenzyl | 553 | 553 |
| 739 | 1-Naphthylmethyl | Methoxy | 3-Hydroxybenzyl | 589 | 589 |
| 740 | 4-F-benzyl | Methoxy | 3-Hydroxybenzyl | 557 | 557 |
| 741 | 3,4-$F_2$-Benzyl | Methoxy | 3-Hydroxybenzyl | 575 | 575 |
| 742 | Cyclohexyl | Methoxy | 3-Hydroxybenzyl | 531 | 531 |
| 743 | 2-Cl-benzyl | Methoxy | 3-Hydroxybenzyl | 573 | 573 |
| 744 | 4-Cl-benzyl | Methoxy | 3-Hydroxybenzyl | 573 | 573 |
| 745 | Cyclohexylmethyl | Methoxy | 1-Naphthylmethyl | 579 | 579 |
| 746 | 4-Phenylbenzyl | Methoxy | 1-Naphthylmethyl | 649 | 649 |
| 747 | 4-$NO_2$-benzyl | Methoxy | 1-Naphthylmethyl | 618 | 618 |
| 748 | 3,4-$Cl_2$-benzyl | Methoxy | 1-Naphthylmethyl | 642 | 642 |
| 749 | Cyclopentyl(spiro) | Methoxy | 1-Naphthylmethyl | 551 | 551 |
| 750 | 4-Methylbenzyl | Methoxy | 1-Naphthylmethyl | 587 | 587 |

TABLE 2-continued

THE BETA-STRAND MIMETICS LIBRARY

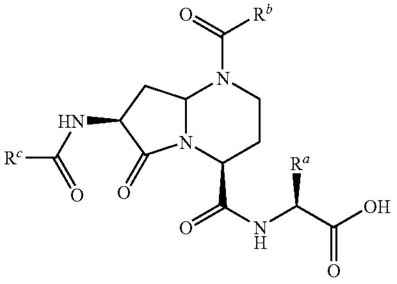

| No. | $R^a$ | $R^b$ | $R^c$ | Mol. Weight | M + H |
|---|---|---|---|---|---|
| 751 | 1-Naphthylmethyl | Methoxy | 1-Naphthylmethyl | 623 | 623 |
| 752 | 4-F-benzyl | Methoxy | 1-Naphthylmethyl | 591 | 591 |
| 753 | 3,4-$F_2$-Benzyl | Methoxy | 1-Naphthylmethyl | 609 | 609 |
| 754 | Cyclohexyl | Methoxy | 1-Naphthylmethyl | 565 | 565 |
| 755 | 2-Cl-benzyl | Methoxy | 1-Naphthylmethyl | 607 | 607 |
| 756 | 4-Cl-benzyl | Methoxy | 1-Naphthylmethyl | 607 | 607 |
| 757 | Cyclohexylmethyl | Methoxy | Phenethyl | 543 | 543 |
| 758 | 4-Phenylbenzyl | Methoxy | Phenethyl | 613 | 613 |
| 759 | 4-$NO_2$-benzyl | Methoxy | Phenethyl | 582 | 582 |
| 760 | 3,4-$Cl_2$-benzyl | Methoxy | Phenethyl | 605 | 605 |
| 761 | Cyclopentyl(spiro) | Methoxy | Phenethyl | 515 | 515 |
| 762 | 4-Methylbenzyl | Methoxy | Phenethyl | 551 | 551 |
| 763 | 1-Naphthylmethyl | Methoxy | Phenethyl | 587 | 587 |
| 764 | 4-F-benzyl | Methoxy | Phenethyl | 555 | 555 |
| 765 | 3,4-$F_2$-Benzyl | Methoxy | Phenethyl | 573 | 573 |
| 766 | Cyclohexyl | Methoxy | Phenethyl | 529 | 529 |
| 767 | 2-Cl-benzyl | Methoxy | Phenethyl | 571 | 571 |
| 768 | 4-Cl-benzyl | Methoxy | Phenethyl | 571 | 571 |
| 769 | Cyclohexylmethyl | Methoxy | 3-Methoxyphenyl | 545 | 545 |
| 770 | 4-Phenylbenzyl | Methoxy | 3-Methoxyphenyl | 615 | 615 |
| 771 | 4-$NO_2$-benzyl | Methoxy | 3-Methoxyphenyl | 584 | 584 |
| 772 | 3,4-$Cl_2$-benzyl | Methoxy | 3-Methoxyphenyl | 607 | 607 |
| 773 | Cyclopentyl-(spiro) | Methoxy | 3-Methoxyphenyl | 517 | 517 |
| 774 | 4-Methylbenzyl | Methoxy | 3-Methoxyphenyl | 553 | 553 |
| 775 | 1-Naphthylmethyl | Methoxy | 3-Methoxyphenyl | 589 | 589 |
| 776 | 4-F-benzyl | Methoxy | 3-Methoxyphenyl | 557 | 557 |
| 777 | 3,4-$F_2$-Benzyl | Methoxy | 3-Methoxyphenyl | 575 | 575 |
| 778 | Cyclohexyl | Methoxy | 3-Methoxyphenyl | 531 | 531 |
| 779 | 2-Cl-benzyl | Methoxy | 3-Methoxyphenyl | 573 | 573 |
| 780 | 4-Cl-benzyl | Methoxy | 3-Methoxyphenyl | 573 | 573 |
| 781 | Cyclohexylmethyl | Methoxy | N-Benzoylaminoethyl | 572 | 572 |
| 782 | 4-Phenylbenzyl | Methoxy | N-Benzoylaminoethyl | 642 | 642 |
| 783 | 4-$NO_2$-benzyl | Methoxy | N-Benzoylaminoethyl | 611 | 611 |
| 784 | 3,4-$Cl_2$-benzyl | Methoxy | N-Benzoylaminoethyl | 634 | 634 |
| 785 | Cyclopentyl-(spiro) | Methoxy | N-Benzoylaminoethyl | 544 | 544 |
| 786 | 4-Methylbenzyl | Methoxy | N-Benzoylaminoethyl | 580 | 580 |
| 787 | 1-Naphthylmethyl | Methoxy | N-Benzoylaminoethyl | 616 | 616 |
| 788 | 4-F-benzyl | Methoxy | N-Benzoylaminoethyl | 584 | 584 |
| 789 | 3,4-$F_2$-Benzyl | Methoxy | N-Benzoylaminoethyl | 602 | 602 |
| 790 | Cyclohexyl | Methoxy | N-Benzoylaminoethyl | 558 | 558 |
| 791 | 2-Cl-benzyl | Methoxy | N-Benzoylaminoethyl | 600 | 600 |
| 792 | 4-Cl-benzyl | Methoxy | N-Benzoylaminoethyl | 600 | 600 |
| 793 | Cyclohexylmethyl | Methoxy | Benzyl | 529 | 529 |
| 794 | 4-Phenylbenzyl | Methoxy | Benzyl | 599 | 599 |
| 795 | 4-$NO_2$-benzyl | Methoxy | Benzyl | 568 | 568 |
| 796 | 3,4-$Cl_2$-benzyl | Methoxy | Benzyl | 591 | 591 |
| 797 | Cyclopentyl-(spiro) | Methoxy | Benzyl | 501 | 501 |
| 798 | 4-Methylbenzyl | Methoxy | Benzyl | 537 | 537 |
| 799 | 1-Naphthylmethyl | Methoxy | Benzyl | 573 | 573 |
| 800 | 4-F-benzyl | Methoxy | Benzyl | 541 | 541 |
| 801 | 3,4-$F_2$-Benzyl | Methoxy | Benzyl | 559 | 559 |
| 802 | Cyclohexyl | Methoxy | Benzyl | 515 | 515 |
| 803 | 2-Cl-benzyl | Methoxy | Benzyl | 557 | 557 |
| 804 | 4-Cl-benzyl | Methoxy | Benzyl | 557 | 557 |
| 805 | Cyclohexylmethyl | Methoxy | 4-$NO_2$-benzyl | 574 | 574 |

TABLE 2-continued

THE BETA-STRAND MIMETICS LIBRARY

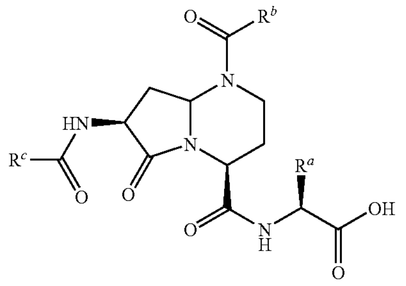

| No. | $R^a$ | $R^b$ | $R^c$ | Mol. Weight | M + H |
|---|---|---|---|---|---|
| 806 | 4-Phenylbenzyl | Methoxy | 4-$NO_2$-benzyl | 644 | 644 |
| 807 | 4-$NO_2$-benzyl | Methoxy | 4-$NO_2$-benzyl | 613 | 613 |
| 808 | 3,4-$Cl_2$-benzyl | Methoxy | 4-$NO_2$-benzyl | 636 | 636 |
| 809 | Cyclopentyl-(spiro) | Methoxy | 4-$NO_2$-benzyl | 546 | 546 |
| 810 | 4-Methylbenzyl | Methoxy | 4-$NO_2$-benzyl | 582 | 582 |
| 811 | 1-Naphthylmethyl | Methoxy | 4-$NO_2$-benzyl | 618 | 618 |
| 812 | 4-F-benzyl | Methoxy | 4-$NO_2$-benzyl | 586 | 586 |
| 813 | 3,4-$F_2$-Benzyl | Methoxy | 4-$NO_2$-benzyl | 604 | 604 |
| 814 | Cyclohexyl | Methoxy | 4-$NO_2$-benzyl | 560 | 560 |
| 815 | 2-Cl-benzyl | Methoxy | 4-$NO_2$-benzyl | 602 | 602 |
| 816 | 4-Cl-benzyl | Methoxy | 4-$NO_2$-benzyl | 602 | 602 |
| 817 | Cyclohexylmethyl | Methoxy | 2,4-Pentadienyl | 505 | 505 |
| 818 | 4-Phenylbenzyl | Methoxy | 2,4-Pentadienyl | 575 | 575 |
| 819 | 4-$NO_2$-benzyl | Methoxy | 2,4-Pentadienyl | 544 | 544 |
| 820 | 3,4-$Cl_2$-benzyl | Methoxy | 2,4-Pentadienyl | 567 | 567 |
| 821 | Cyclopentyl-(spiro) | Methoxy | 2,4-Pentadienyl | 477 | 477 |
| 822 | 4-Methylbenzyl | Methoxy | 2,4-Pentadienyl | 513 | 513 |
| 823 | 1-Naphthylmethyl | Methoxy | 2,4-Pentadienyl | 549 | 549 |
| 824 | 4-F-benzyl | Methoxy | 2,4-Pentadienyl | 517 | 517 |
| 825 | 3,4-$F_2$-Benzyl | Methoxy | 2,4-Pentadienyl | 535 | 535 |
| 826 | Cyclohexyl | Methoxy | 2,4-Pentadienyl | 491 | 491 |
| 827 | 2-Cl-benzyl | Methoxy | 2,4-Pentadienyl | 533 | 533 |
| 828 | 4-Cl-benzyl | Methoxy | 2,4-Pentadienyl | 533 | 533 |
| 829 | Cyclohexylmethyl | Methoxy | 3-(2,6-$Cl_2$-pyridyl)methyl | 584 | 584 |
| 830 | 4-Phenylbenzyl | Methoxy | 3-(2,6-$Cl_2$-pyridyl)methyl | 655 | 655 |
| 831 | 4-$NO_2$-benzyl | Methoxy | 3-(2,6-$Cl_2$-pyridyl)methyl | 623 | 623 |
| 832 | 3,4-$Cl_2$-benzyl | Methoxy | 3-(2,6-$Cl_2$-pyridyl)methyl | 647 | 647 |
| 833 | Cyclopentyl(spiro) | Methoxy | 3-(2,6-$Cl_2$-pyridyl)methyl | 556 | 556 |
| 834 | 4-Methylbenzyl | Methoxy | 3-(2,6-$Cl_2$-pyridyl)methyl | 592 | 592 |
| 835 | 1-Naphthylmethyl | Methoxy | 3-(2,6-$Cl_2$-pyridyl)methyl | 628 | 628 |
| 836 | 4-F-benzyl | Methoxy | 3-(2,6-$Cl_2$-pyridyl)methyl | 596 | 596 |
| 837 | 3,4-$F_2$-Benzyl | Methoxy | 3-(2,6-$Cl_2$-pyridyl)methyl | 614 | 614 |
| 838 | Cyclohexyl | Methoxy | 3-(2,6-$Cl_2$-pyridyl)methyl | 570 | 570 |
| 839 | 2-Cl-benzyl | Methoxy | 3-(2,6-$Cl_2$-pyridyl)methyl | 613 | 613 |
| 840 | 4-Cl-benzyl | Methoxy | 3-(2,6-$Cl_2$-pyridyl)methyl | 613 | 613 |
| 841 | Cyclohexylmethyl | Methoxy | Chromen-2-one-3-methyl | 583 | 583 |
| 842 | 4-Phenylbenzyl | Methoxy | Chromen-2-one-3-methyl | 653 | 653 |
| 843 | 4-$NO_2$-benzyl | Methoxy | Chromen-2-one-3-methyl | 622 | 622 |
| 844 | 3,4-$Cl_2$-benzyl | Methoxy | Chromen-2-one-3-methyl | 645 | 645 |
| 845 | Cyclopentyl-(spiro) | Methoxy | Chromen-2-one-3-methyl | 555 | 555 |
| 846 | 4-Methylbenzyl | Methoxy | Chromen-2-one-3-methyl | 591 | 591 |
| 847 | 1-Naphthylmethyl | Methoxy | Chromen-2-one-3-methyl | 627 | 627 |
| 848 | 4-F-benzyl | Methoxy | Chromen-2-one-3-methyl | 595 | 595 |
| 849 | 3,4-$F_2$-Benzyl | Methoxy | Chromen-2-one-3-methyl | 613 | 613 |
| 850 | Cyclohexyl | Methoxy | Chromen-2-one-3-methyl | 569 | 569 |
| 851 | 2-Cl-benzyl | Methoxy | Chromen-2-one-3-methyl | 611 | 611 |
| 852 | 4-Cl-benzyl | Methoxy | Chromen-2-one-3-methyl | 611 | 611 |
| 853 | Cyclohexylmethyl | Methoxy | Methoxymethyl | 483 | 483 |
| 854 | 4-Phenylbenzyl | Methoxy | Methoxymethyl | 553 | 553 |
| 855 | 4-$NO_2$-benzyl | Methoxy | Methoxymethyl | 521 | 521 |
| 856 | 3,4-$Cl_2$-benzyl | Methoxy | Methoxymethyl | 545 | 545 |
| 857 | Cyclopentyl-(spiro) | Methoxy | Methoxymethyl | 454 | 454 |

TABLE 2-continued

THE BETA-STRAND MIMETICS LIBRARY

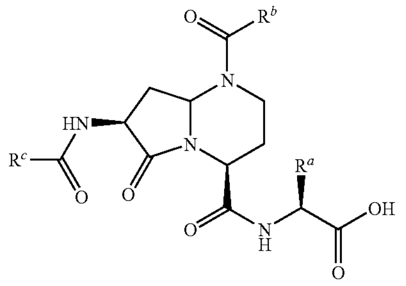

| No. | $R^a$ | $R^b$ | $R^c$ | Mol. Weight | M + H |
|---|---|---|---|---|---|
| 858 | 4-Methylbenzyl | Methoxy | Methoxymethyl | 491 | 491 |
| 859 | 1-Naphthylmethyl | Methoxy | Methoxymethyl | 527 | 527 |
| 860 | 4-F-benzyl | Methoxy | Methoxymethyl | 494 | 494 |
| 861 | 3,4-$F_2$-Benzyl | Methoxy | Methoxymethyl | 512 | 512 |
| 862 | Cyclohexyl | Methoxy | Methoxymethyl | 469 | 469 |
| 863 | 2-Cl-benzyl | Methoxy | Methoxymethyl | 511 | 511 |
| 864 | 4-Cl-benzyl | Methoxy | Methoxymethyl | 511 | 511 |

Figure 2:
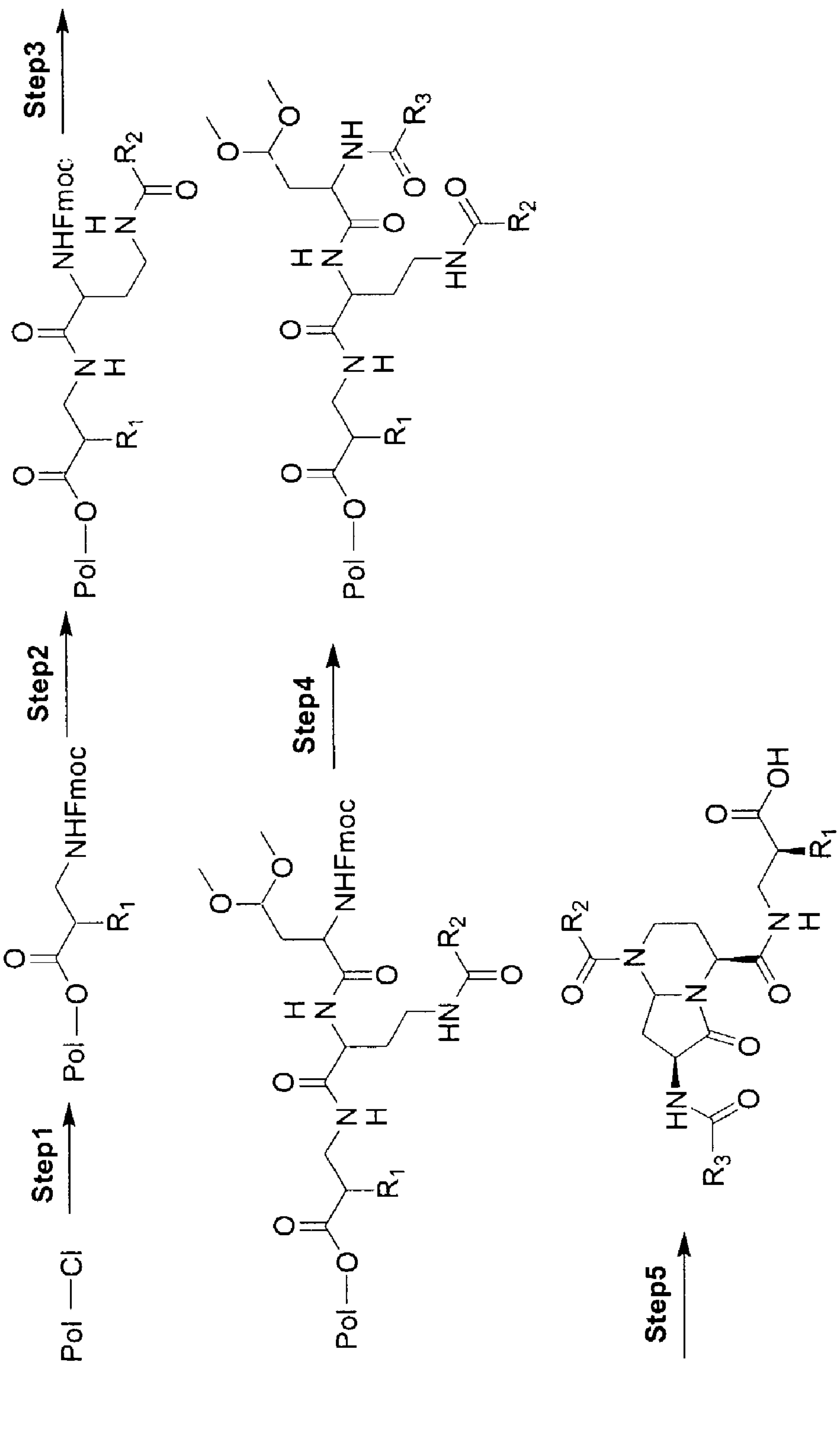

The synthesis of peptide mimetics in a library of the present invention accomplished using the general scheme of β-strand mimetics library as n FIG. 2. The synthesis of selected peptide mimetics of a bicyclic e library of the present invention was accomplished using a FlexChem Block which has a 96 well plate. In the above scheme 'Pol' represents 2-chlorotrityl chloride resin (Novabiochem) and a detailed procedure is provided below.

Step 1 The 2-chlorotrityl chloride resin (1 mmol/g) and a solution Fmoc-$R_1$-beta-Amino Acid (1.5 equiv.) and DIEA (2 equiv.) in DCE were in a 96 well Robinson block (Flexchem). The reaction mixture was shaken for 12 hours at room temperature. The resin was washed with DMF, MeOH, and DCM.

Step2 To the resin swollen by DMF before reaction was added 25% piperidine in DMF. Thereafter, the reaction mixture was shaken for 30 min at room temperature. The deprotection step was repeated and then the product mixture was washed with DMF, MeOH, and then DCM. A solution of 4-$R_2$-amino-2-Fmoc-aminobutyric acid (1.5 equiv.), DIC (1.5 equiv.), HOBT (1.5 equiv.) in NMP was added to the resin. After the reaction mixture was shaken for 12 hours at room temperature, the resin was washed with DMF, MeOH, and then DCM.

Step 3 To the resin swollen by DMF before reaction was added 25% piperidine in DMF. Thereafter, the reaction mixture was shaken for 30 min at room temperature. The deprotection step was repeated and the product mixture was washed with DMF, MeOH, and then DCM. A solution of 2-(9H-fluoren-9-ylmethoxycarbonylamino)-5,5-dimethoxy-pentanoic acid (1.5 equiv.), DIC (1.5 equiv.), and HOBT (1.5 equiv.) in NMP was added to the resin. After the reaction mixture was shaken for 12 hours at room temperature, the resin was washed with DMF, MeOH, and then DCM.

Step 4 To the resin swollen by DMF before reaction was added 25% piperidine in DMF. Thereafter, the reaction mixture was shaken for 30 min at room temperature. The deprotection step was repeated and then the product mixture was washed with DMF, MeOH, and then DCM. A solution of commercially available $R_3$-acid (1.5 equiv.), DIC (1.5 equiv.), and HOBT (1.5 equiv.) in NMP was added to the resin. After the reaction mixture was shaken for 12 hours at room temperature, the resin was washed with DMF, MeOH, and then DCM.

Step 5 The resin was treated with formic acid (1.2 mL each well) for 18 hours at room temperature. Thereafter, the resin was removed by filtration, and the filtrate was condensed under reduced pressure using SpeedVac (Servant) to give the product as oil. These products were diluted with 50% water/acetonitrile and then lyophilized after freezing.

Table 3 shows a β-strand mimetics library which can be prepared according to the present invention, of which representative preparation is given in Example 10. Compounds of Table 3 illustrate one aspect of the invention, namely compounds wherein A is —(CH)—, B is $—(CH_2)_m—$ with m=1, W is nothing, i.e., it is a direct bond between Rb and N of the heterocyclic ring, X is —NH(C═O)—, Y is oxygen, Z is hydrogen so that C═Z represents $CH_2$, L is $—C(═O)NHR_3$, n=0, $R_4$ is hydrogen, and $R_1$, $R_2$, and $R_3$ are the same or different and are independently selected from an amino acid side chain moiety or derivative thereof, the remainder of the molecule, a linker and a solid support, and stereoisomers thereof. In various embodiments of this aspect of the invention, $R_1$, $R_2$, and $R_3$ are independently selected from relatively low molecular weight moieties, i.e., organic groups having molecular weights of between 15 (methyl) and 1,000 g/mol; and/or at least one of $R_1$, $R_2$, and $R_3$ represents an amino acid side chain or derivative thereof. For example, in the compounds of Table 3, $R^3$ represents glutaric acid derivatives. In one aspect, the compounds of the present invention have a molecular weight within the range of about 450 to 800 g/mol, where the compounds of Table 3 provide numerous illustrations of such compounds.

TABLE 3

THE BETA-STRAND MIMETICS LIBRARY

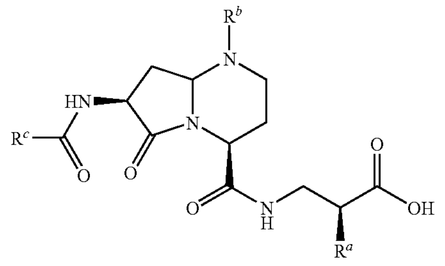

| No. | $R^a$ | $R^b$ | $R^c$ | Mol. Weight | M + H |
|---|---|---|---|---|---|
| 865 | Propyl | Phenyl | 4-Methoxybenzyl | 565 | 565 |
| 866 | Propyl | Phenyl | 3,4-$Cl_2$-benzyl | 585 | 585 |
| 867 | Propyl | Phenyl | 1-Naphthyl | 589 | 589 |
| 868 | Propyl | Phenyl | Piperonyl | 549 | 549 |
| 869 | Propyl | Phenyl | 2,4,5-Trimethoxyphenyl | 571 | 571 |
| 870 | Propyl | Phenyl | 3-Hydroxybenzyl | 551 | 551 |
| 871 | Propyl | Phenyl | 1-Naphthylmethyl | 565 | 565 |
| 872 | Propyl | Phenyl | Phenethyl | 578 | 578 |
| 873 | Propyl | Phenyl | 3-Methoxyphenyl | 611 | 611 |
| 874 | Propyl | Phenyl | N-Benzoylaminoethyl | 535 | 535 |
| 875 | Propyl | Phenyl | Benzyl | 551 | 551 |
| 876 | Propyl | Phenyl | 4-$NO_2$-benzyl | 580 | 580 |
| 877 | Propyl | Methoxy | 4-Methoxybenzyl | 519 | 519 |
| 878 | Propyl | Methoxy | 3,4-$Cl_2$-benzyl | 539 | 539 |
| 879 | Propyl | Methoxy | 1-Naphthyl | 543 | 543 |
| 880 | Propyl | Methoxy | Piperonyl | 503 | 503 |
| 881 | Propyl | Methoxy | 2,4,5-Trimethoxyphenyl | 525 | 525 |
| 882 | Propyl | Methoxy | 3-Hydroxybenzyl | 505 | 505 |
| 883 | Propyl | Methoxy | 1-Naphthylmethyl | 519 | 519 |
| 884 | Propyl | Methoxy | Phenethyl | 532 | 532 |
| 885 | Propyl | Methoxy | 3-Methoxyphenyl | 565 | 565 |
| 886 | Propyl | Methoxy | N-Benzoylaminoethyl | 489 | 489 |
| 887 | Propyl | Methoxy | Benzyl | 505 | 505 |
| 888 | Propyl | Methoxy | 4-$NO_2$-benzyl | 534 | 534 |
| 889 | Isobutyl | Phenyl | 4-Methoxybenzyl | 593 | 593 |
| 890 | Isobutyl | Phenyl | 3,4-$Cl_2$-benzyl | 613 | 613 |
| 891 | Isobutyl | Phenyl | 1-Naphthyl | 618 | 618 |
| 892 | Isobutyl | Phenyl | Piperonyl | 577 | 577 |
| 893 | Isobutyl | Phenyl | 2,4,5-Trimethoxyphenyl | 599 | 599 |
| 894 | Isobutyl | Phenyl | 3-Hydroxybenzyl | 579 | 579 |
| 895 | Isobutyl | Phenyl | 1-Naphthylmethyl | 593 | 593 |
| 896 | Isobutyl | Phenyl | Phenethyl | 606 | 606 |
| 897 | Isobutyl | Phenyl | 3-Methoxyphenyl | 639 | 639 |
| 898 | Isobutyl | Phenyl | N-Benzoylaminoethyl | 563 | 563 |
| 899 | Isobutyl | Phenyl | Benzyl | 579 | 579 |
| 900 | Isobutyl | Phenyl | 4-$NO_2$-benzyl | 608 | 608 |
| 901 | Isobutyl | Methoxy | 4-Methoxybenzyl | 547 | 547 |
| 902 | Isobutyl | Methoxy | 3,4-$Cl_2$-benzyl | 567 | 567 |
| 903 | Isobutyl | Methoxy | 1-Naphthyl | 571 | 571 |
| 904 | Isobutyl | Methoxy | Piperonyl | 531 | 531 |
| 905 | Isobutyl | Methoxy | 2,4,5-Trimethoxyphenyl | 553 | 553 |
| 906 | Isobutyl | Methoxy | 3-Hydroxybenzyl | 533 | 533 |
| 907 | Isobutyl | Methoxy | 1-Naphthylmethyl | 547 | 547 |
| 908 | Isobutyl | Methoxy | Phenethyl | 560 | 560 |
| 909 | Isobutyl | Methoxy | 3-Methoxyphenyl | 593 | 593 |
| 910 | Isobutyl | Methoxy | N-Benzoylaminoethyl | 517 | 517 |
| 911 | Isobutyl | Methoxy | Benzyl | 533 | 533 |
| 912 | Isobutyl | Methoxy | 4-$NO_2$-benzyl | 562 | 562 |
| 913 | 4-Br-benzyl | Phenyl | 4-Methoxybenzyl | 692 | 692 |
| 914 | 4-Br-benzyl | Phenyl | 3,4-$Cl_2$-benzyl | 712 | 712 |
| 915 | 4-Br-benzyl | Phenyl | 1-Naphthyl | 716 | 716 |
| 916 | 4-Br-benzyl | Phenyl | Piperonyl | 676 | 676 |
| 917 | 4-Br-benzyl | Phenyl | 2,4,5-Trimethoxyphenyl | 698 | 698 |
| 918 | 4-Br-benzyl | Phenyl | 3-Hydroxybenzyl | 678 | 678 |
| 919 | 4-Br-benzyl | Phenyl | 1-Naphthylmethyl | 692 | 692 |
| 920 | 4-Br-benzyl | Phenyl | Phenethyl | 705 | 705 |
| 921 | 4-Br-benzyl | Phenyl | 3-Methoxyphenyl | 738 | 738 |
| 922 | 4-Br-benzyl | Phenyl | N-Benzoylaminoethyl | 662 | 662 |
| 923 | 4-Br-benzyl | Phenyl | Benzyl | 678 | 678 |

TABLE 3-continued

THE BETA-STRAND MIMETICS LIBRARY

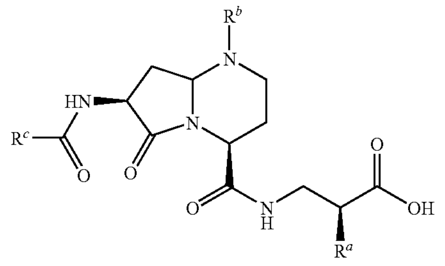

| No. | $R^a$ | $R^b$ | $R^c$ | Mol. Weight | M + H |
|---|---|---|---|---|---|
| 924 | 4-Br-benzyl | Phenyl | 4-$NO_2$-benzyl | 707 | 707 |
| 925 | 4-Br-benzyl | Methoxy | 4-Methoxybenzyl | 646 | 646 |
| 926 | 4-Br-benzyl | Methoxy | 3,4-$Cl_2$-benzyl | 666 | 666 |
| 927 | 4-Br-benzyl | Methoxy | 1-Naphthyl | 670 | 670 |
| 928 | 4-Br-benzyl | Methoxy | Piperonyl | 630 | 630 |
| 929 | 4-Br-benzyl | Methoxy | 2,4,5-Trimethoxyphenyl | 652 | 652 |
| 930 | 4-Br-benzyl | Methoxy | 3-Hydroxybenzyl | 631 | 631 |
| 931 | 4-Br-benzyl | Methoxy | 1-Naphthylmethyl | 645 | 645 |
| 932 | 4-Br-benzyl | Methoxy | Phenethyl | 659 | 659 |
| 933 | 4-Br-benzyl | Methoxy | 3-Methoxyphenyl | 692 | 692 |
| 934 | 4-Br-benzyl | Methoxy | N-Benzoylaminoethyl | 615 | 615 |
| 935 | 4-Br-benzyl | Methoxy | Benzyl | 631 | 631 |
| 936 | 4-Br-benzyl | Methoxy | 4-$NO_2$-benzyl | 660 | 660 |
| 937 | Benzyl | Phenyl | 4-Methoxybenzyl | 613 | 613 |
| 938 | Benzyl | Phenyl | 3,4-$Cl_2$-benzyl | 633 | 633 |
| 939 | Benzyl | Phenyl | 1-Naphthyl | 638 | 638 |
| 940 | Benzyl | Phenyl | Piperonyl | 597 | 597 |
| 941 | Benzyl | Phenyl | 2,4,5-Trimethoxyphenyl | 619 | 619 |
| 942 | Benzyl | Phenyl | 3-Hydroxybenzyl | 599 | 599 |
| 943 | Benzyl | Phenyl | 1-Naphthylmethyl | 613 | 613 |
| 944 | Benzyl | Phenyl | Phenethyl | 626 | 626 |
| 945 | Benzyl | Phenyl | 3-Methoxyphenyl | 659 | 659 |
| 946 | Benzyl | Phenyl | N-Benzoylaminoethyl | 583 | 583 |
| 947 | Benzyl | Phenyl | Benzyl | 599 | 599 |
| 948 | Benzyl | Phenyl | 4-$NO_2$-benzyl | 628 | 628 |
| 949 | Benzyl | Methoxy | 4-Methoxybenzyl | 567 | 567 |
| 950 | Benzyl | Methoxy | 3,4-$Cl_2$-benzyl | 587 | 587 |
| 951 | Benzyl | Methoxy | 1-Naphthyl | 591 | 591 |
| 952 | Benzyl | Methoxy | Piperonyl | 551 | 551 |
| 953 | Benzyl | Methoxy | 2,4,5-Trimethoxyphenyl | 573 | 573 |
| 954 | Benzyl | Methoxy | 3-Hydroxybenzyl | 553 | 553 |
| 955 | Benzyl | Methoxy | 1-Naphthylmethyl | 567 | 567 |
| 956 | Benzyl | Methoxy | Phenethyl | 580 | 580 |
| 957 | Benzyl | Methoxy | 3-Methoxyphenyl | 613 | 613 |
| 958 | Benzyl | Methoxy | N-Benzoylaminoethyl | 537 | 537 |
| 959 | Benzyl | Methoxy | Benzyl | 553 | 553 |
| 960 | Benzyl | Methoxy | 4-$NO_2$-benzyl | 582 | 582 |
| 961 | Propyl | Benzyloxy | 2,4-Pentadienyl | 541 | 541 |
| 962 | Propyl | Benzyloxy | 3-(2,6-$Cl_2$-pyridyl)methyl | 620 | 620 |
| 963 | Propyl | Benzyloxy | Chromen-2-one-3-methyl | 619 | 619 |
| 964 | Propyl | Benzyloxy | Methoxymethyl | 519 | 519 |
| 965 | Propyl | Benzyloxy | Pyran-2-one-4-methyl | 569 | 569 |
| 966 | Propyl | Benzyloxy | Ethyl | 503 | 503 |
| 967 | Propyl | Benzyloxy | 2-Ethyldecanyl | 629 | 629 |
| 968 | Propyl | Benzyloxy | Pyrazin-2-methyl | 553 | 553 |
| 969 | Propyl | Benzyloxy | 4-Pyridylmethyl | 552 | 552 |
| 970 | Propyl | Benzyloxy | 4-Butenyl | 529 | 529 |
| 971 | Propyl | Benzyloxy | 2-$NO_2$-5-Cl-phenyl | 630 | 630 |
| 972 | Propyl | Benzyloxy | Cyanomethyl | 514 | 514 |
| 973 | Propyl | Methoxy | 2,4-Pentadienyl | 465 | 465 |
| 974 | Propyl | Methoxy | 3-(2,6-$Cl_2$-pyridyl)methyl | 544 | 544 |
| 975 | Propyi | Methoxy | Chromen-2-one-3-methyl | 543 | 543 |
| 976 | Propyl | Methoxy | Methoxymethyl | 442 | 442 |
| 977 | Propyl | Methoxy | Pyran-2-one-4-methyl | 492 | 492 |
| 978 | Propyl | Methoxy | Ethyl | 426 | 426 |
| 979 | Propyl | Methoxy | 2-Ethyldecanyl | 553 | 553 |
| 980 | Propyl | Methoxy | Pyrazin-2-methyl | 476 | 476 |

TABLE 3-continued

THE BETA-STRAND MIMETICS LIBRARY

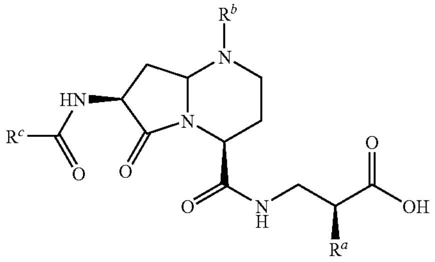

| No. | $R^a$ | $R^b$ | $R^c$ | Mol. Weight | M + H |
|---|---|---|---|---|---|
| 981 | Propyl | Methoxy | 4-Pyridylmethyl | 476 | 476 |
| 982 | Propyl | Methoxy | 4-Butenyl | 453 | 453 |
| 983 | Propyl | Methoxy | 2-$NO_2$-5-Cl-phenyl | 554 | 554 |
| 984 | Propyl | Methoxy | Cyanomethyl | 437 | 437 |
| 985 | Isobutyl | Benzyloxy | 2,4-Pentadienyl | 569 | 569 |
| 986 | Isobutyl | Benzyloxy | 3-(2,6-$Cl_2$-pyridyl)methyl | 649 | 649 |
| 987 | Isobutyl | Benzyloxy | Chromen-2-one-3-methyl | 647 | 647 |
| 988 | Isobutyl | Benzyloxy | Methoxymethyl | 547 | 547 |
| 989 | Isobutyl | Benzyloxy | Pyran-2-one-4-methyl | 597 | 597 |
| 990 | Isobutyl | Benzyloxy | Ethyl | 531 | 531 |
| 991 | Isobutyl | Benzyloxy | 2-Ethyldecanyl | 657 | 657 |
| 992 | Isobutyl | Benzyloxy | Pyrazin-2-methyl | 581 | 581 |
| 993 | Isobutyl | Benzyloxy | 4-Pyridylmethyl | 580 | 580 |
| 994 | Isobutyl | Benzyloxy | 4-Butenyl | 557 | 557 |
| 995 | Isobutyl | Benzyloxy | 2-$NO_2$-5-Cl-phenyl | 658 | 658 |
| 996 | Isobutyl | Benzyloxy | Cyanomethyl | 542 | 542 |
| 997 | Isobutyl | Methoxy | 2,4-Pentadienyl | 493 | 493 |
| 998 | Isobutyl | Methoxy | 3-(2,6-$Cl_2$-pyridyl)methyl | 572 | 572 |
| 999 | Isobutyl | Methoxy | Chromen-2-one-3-methyl | 571 | 571 |
| 1000 | Isobutyl | Methoxy | Methoxymethyl | 471 | 471 |
| 1001 | Isobutyl | Methoxy | Pyran-2-one-4-methyl | 521 | 521 |
| 1002 | Isobutyl | Methoxy | Ethyl | 455 | 455 |
| 1003 | Isobutyl | Methoxy | 2-Ethyldecanyl | 581 | 581 |
| 1004 | Isobutyl | Methoxy | Pyrazin-2-methyl | 505 | 505 |
| 1005 | Isobutyl | Methoxy | 4-Pyridylmethyl | 504 | 504 |
| 1006 | Isobutyl | Methoxy | 4-Butenyl | 481 | 481 |
| 1007 | Isobutyl | Methoxy | 2-$NO_2$-5-Cl-phenyl | 582 | 582 |
| 1008 | Isobutyl | Methoxy | Cyanomethyl | 466 | 466 |
| 1009 | Benzyl | Benzyloxy | 2,4-Pentadienyl | 589 | 589 |
| 1010 | Benzyl | Benzyloxy | 3-(2,6-$Cl_2$-pyridyl)methyl | 669 | 669 |
| 1011 | Benzyl | Benzyloxy | Chromen-2-one-3-methyl | 667 | 667 |
| 1012 | Benzyl | Benzyloxy | Methoxymethyl | 567 | 567 |
| 1013 | Benzyl | Benzyloxy | Pyran-2-one-4-methyl | 617 | 617 |
| 1014 | Benzyl | Benzyloxy | Ethyl | 551 | 551 |
| 1015 | Benzyl | Benzyloxy | 2-Ethyldecanyl | 677 | 677 |
| 1016 | Benzyl | Benzyloxy | Pyrazin-2-methyl | 601 | 601 |
| 1017 | Benzyl | Benzyloxy | 4-Pyridylmethyl | 600 | 600 |
| 1018 | Benzyl | Benzyloxy | 4-Butenyl | 577 | 577 |
| 1019 | Benzyl | Benzyloxy | 2-$NO_2$-5-Cl-phenyl | 678 | 678 |
| 1020 | Benzyl | Benzyloxy | Cyanomethyl | 562 | 562 |
| 1021 | Benzyl | Methoxy | 2,4-Pentadienyl | 513 | 513 |
| 1022 | Benzyl | Methoxy | 3-(2,6-$Cl_2$-pyridyl)methyl | 592 | 592 |
| 1023 | Benzyl | Methoxy | Chromen-2-one-3-methyl | 591 | 591 |
| 1024 | Benzyl | Methoxy | Methoxymethyl | 491 | 491 |
| 1025 | Benzyl | Methoxy | Pyran-2-one-4-methyl | 541 | 541 |
| 1026 | Benzyl | Methoxy | Ethyl | 475 | 475 |
| 1027 | Benzyl | Methoxy | 2-Ethyldecanyl | 601 | 601 |
| 1028 | Benzyl | Methoxy | Pyrazin-2-methyl | 525 | 525 |
| 1029 | Benzyl | Methoxy | 4-Pyridylmethyl | 524 | 524 |
| 1030 | Benzyl | Methoxy | 4-Butenyl | 501 | 501 |
| 1031 | Benzyl | Methoxy | 2-$NO_2$-5-Cl-phenyl | 602 | 602 |
| 1032 | Benzyl | Methoxy | Cyanomethyl | 486 | 486 |
| 1033 | Phenylpropyl | Benzyloxy | 2,4-Pentadienyl | 617 | 617 |
| 1034 | Phenylpropyl | Benzyloxy | 3-(2,6-$Cl_2$-pyridyl)methyl | 697 | 697 |

TABLE 3-continued

THE BETA-STRAND MIMETICS LIBRARY

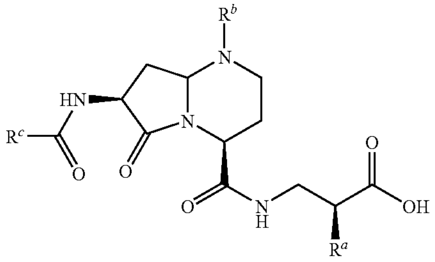

| No. | $R^a$ | $R^b$ | $R^c$ | Mol. Weight | M + H |
|---|---|---|---|---|---|
| 1035 | Phenylpropyl | Benzyloxy | Chromen-2-one-3-methyl | 695 | 695 |
| 1036 | Phenylpropyl | Benzyloxy | Methoxymethyl | 595 | 595 |
| 1037 | Phenylpropyl | Benzyloxy | Pyran-2-one-4-methyl | 645 | 645 |
| 1038 | Phenylpropyl | Benzyloxy | Ethyl | 579 | 579 |
| 1039 | Phenylpropyl | Benzyloxy | 2-Ethyldecanyl | 705 | 705 |
| 1040 | Phenylpropyl | Benzyloxy | Pyrazin-2-methyl | 629 | 629 |
| 1041 | Phenylpropyl | Benzyloxy | 4-Pyridylmethyl | 628 | 628 |
| 1042 | Phenylpropyl | Benzyloxy | 4-Butenyl | 605 | 605 |
| 1043 | Phenylpropyl | Benzyloxy | 2-$NO_2$-5-Cl-phenyl | 706 | 706 |
| 1044 | Phenylpropyl | Benzyloxy | Cyanomethyl | 590 | 590 |
| 1045 | Phenylpropyl | Methoxy | 2,4-Pentadienyl | 541 | 541 |
| 1046 | Phenylpropyl | Methoxy | 3-(2,6-$Cl_2$-pyridyl)methyl | 620 | 620 |
| 1047 | Phenylpropyl | Methoxy | Chromen-2-one-3-methyl | 619 | 619 |
| 1048 | Phenylpropyl | Methoxy | Methoxymethyl | 519 | 519 |
| 1049 | Phenylpropyl | Methoxy | Pyran-2-one-4-methyl | 569 | 569 |
| 1050 | Phenylpropyl | Methoxy | Ethyl | 503 | 503 |
| 1051 | Phenylpropyl | Methoxy | 2-Ethyldecanyl | 629 | 629 |
| 1052 | Phenylpropyl | Methoxy | Pyrazin-2-methyl | 553 | 553 |
| 1053 | Phenylpropyl | Methoxy | 4-Pyridylmethyl | 552 | 552 |
| 1054 | Phenylpropyl | Methoxy | 4-Butenyl | 529 | 529 |
| 1055 | Phenylpropyl | Methoxy | 2-$NO_2$-5-Cl-phenyl | 630 | 630 |
| 1056 | Phenylpropyl | Methoxy | Cyanomethyl | 514 | 514 |
| 1057 | Methyl | Methoxy | 4-Methoxybenzyl | 491 | 491 |
| 1058 | Methyl | Methoxy | 3,4-$Cl_2$-benzyl | 515 | 515 |
| 1059 | Methyl | Methoxy | 1-Naphthyl | 497 | 497 |
| 1060 | Methyl | Methoxy | Piperonyl | 490 | 490 |
| 1061 | Methyl | Methoxy | 2,4,5-Trimethoxyphenyl | 537 | 537 |
| 1062 | Methyl | Methoxy | 3-Hydroxybenzyl | 476 | 476 |
| 1063 | Methyl | Methoxy | 1-Naphthylmethyl | 511 | 511 |
| 1064 | Methyl | Methoxy | Phenethyl | 475 | 475 |
| 1065 | Methyl | Methoxy | 3-Methoxyphenyl | 476 | 476 |
| 1066 | Methyl | Methoxy | N-Benzoylaminoethyl | 504 | 504 |
| 1067 | Methyl | Methoxy | Benzyl | 460 | 460 |
| 1068 | Methyl | Methoxy | 4-$NO_2$-benzyl | 505 | 505 |
| 1069 | Amino | Methoxy | 4-Methoxybenzyl | 492 | 492 |
| 1070 | Amino | Methoxy | 3,4-$Cl_2$-benzyl | 516 | 516 |
| 1071 | Amino | Methoxy | 1-Naphthyl | 498 | 498 |
| 1072 | Amino | Methoxy | Piperonyl | 491 | 491 |
| 1073 | Amino | Methoxy | 2,4,5-Trimethoxyphenyl | 538 | 538 |
| 1074 | Amino | Methoxy | 3-Hydroxybenzyl | 477 | 477 |
| 1075 | Amino | Methoxy | 1-Naphthylmethyl | 512 | 512 |
| 1076 | Amino | Methoxy | Phenethyl | 476 | 476 |
| 1077 | Amino | Methoxy | 3-Methoxyphenyl | 477 | 477 |
| 1078 | Amino | Methoxy | N-Benzoylaminoethyl | 505 | 505 |
| 1079 | Amino | Methoxy | Benzyl | 461 | 461 |
| 1080 | Amino | Methoxy | 4-$NO_2$-benzyl | 506 | 506 |
| 1081 | 3-Propenyl | Methoxy | 4-Methoxybenzyl | 517 | 517 |
| 1082 | 3-Propenyl | Methoxy | 3,4-$Cl_2$-benzyl | 541 | 541 |
| 1083 | 3-Propenyl | Methoxy | 1-Naphthyl | 523 | 523 |
| 1084 | 3-Propenyl | Methoxy | Piperonyl | 517 | 517 |
| 1085 | 3-Propenyl | Methoxy | 2,4,5-Trimethoxyphenyl | 563 | 563 |
| 1086 | 3-Propenyl | Methoxy | 3-Hydroxybenzyl | 503 | 503 |
| 1087 | 3-Propenyl | Methoxy | 1-Naphthylmethyl | 537 | 537 |
| 1088 | 3-Propenyl | Methoxy | Phenethyl | 501 | 501 |
| 1089 | 3-Propenyl | Methoxy | 3-Methoxyphenyl | 503 | 503 |
| 1090 | 3-Propenyl | Methoxy | N-Benzoylaminoethyl | 530 | 530 |
| 1091 | 3-Propenyl | Methoxy | Benzyl | 487 | 487 |

TABLE 3-continued

THE BETA-STRAND MIMETICS LIBRARY

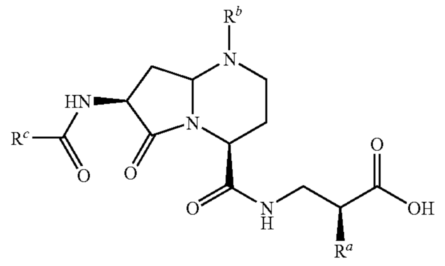

| No. | $R^a$ | $R^b$ | $R^c$ | Mol. Weight | M + H |
|---|---|---|---|---|---|
| 1092 | 3-Propenyl | Methoxy | 4-$NO_2$-benzyl | 532 | 532 |
| 1093 | Ethanoic acid | Methoxy | 4-Methoxybenzyl | 535 | 535 |
| 1094 | Ethanoic acid | Methoxy | 3,4-$Cl_2$-benzyl | 559 | 559 |
| 1095 | Ethanoic acid | Methoxy | 1-Naphthyl | 541 | 541 |
| 1096 | Ethanoic acid | Methoxy | Piperonyl | 534 | 534 |
| 1097 | Ethanoic acid | Methoxy | 2,4,5-Trimethoxyphenyl | 581 | 581 |
| 1098 | Ethanoic acid | Methoxy | 3-Hydroxybenzyl | 521 | 521 |
| 1099 | Ethanoic acid | Methoxy | 1-Naphthylmethyl | 555 | 555 |
| 1100 | Ethanoic acid | Methoxy | Phenethyl | 519 | 519 |
| 1101 | Ethanoic acid | Methoxy | 3-Methoxyphenyl | 521 | 521 |
| 1102 | Ethanoic acid | Methoxy | N-Benzoylaminoethyl | 548 | 548 |
| 1103 | Ethanoic acid | Methoxy | Benzyl | 505 | 505 |
| 1104 | Ethanoic acid | Methoxy | 4-$NO_2$-benzyl | 549 | 549 |
| 1105 | Propionic acid | Methoxy | 4-Methoxybenzyl | 549 | 549 |
| 1106 | Propionic acid | Methoxy | 3,4-$Cl_2$-benzyl | 573 | 573 |
| 1107 | Propionic acid | Methoxy | 1-Naphthyl | 555 | 555 |
| 1108 | Propionic acid | Methoxy | Piperonyl | 549 | 549 |
| 1109 | Propionic acid | Methoxy | 2,4,5-Trimethoxyphenyl | 595 | 595 |
| 1110 | Propionic acid | Methoxy | 3-Hydroxybenzyl | 535 | 535 |
| 1111 | Propionic acid | Methoxy | 1-Naphthylmethyl | 569 | 569 |
| 1112 | Propionic acid | Methoxy | Phenethyl | 533 | 533 |
| 1113 | Propionic acid | Methoxy | 3-Methoxyphenyl | 535 | 535 |
| 1114 | Propionic acid | Methoxy | N-Benzoylaminoethyl | 562 | 562 |
| 1115 | Propionic acid | Methoxy | Benzyl | 519 | 519 |
| 1116 | Propionic acid | Methoxy | 4-$NO_2$-benzyl | 564 | 564 |
| 1117 | 4-Vinylbenzyl | Methoxy | 4-Methoxybenzyl | 593 | 593 |
| 1118 | 4-Vinyibenzyl | Methoxy | 3,4-$Cl_2$-benzyl | 617 | 617 |
| 1119 | 4-Vinylbenzyl | Methoxy | 1 -Naphthyl | 599 | 599 |
| 1120 | 4-Vinylbenzyl | Methoxy | Piperonyl | 593 | 593 |
| 1121 | 4-Vinylbenzyl | Methoxy | 2,4,5-Trimethoxyphenyl | 639 | 639 |
| 1122 | 4-Vinylbenzyl | Methoxy | 3-Hydroxybenzyl | 579 | 579 |
| 1123 | 4-Vinylbenzyl | Methoxy | 1-Naphthylmethyl | 613 | 613 |
| 1124 | 4-Vinylbenzyl | Methoxy | Phenethyl | 577 | 577 |
| 1125 | 4-Vinylbenzyl | Methoxy | 3-Methoxyphenyl | 579 | 579 |
| 1126 | 4-Vinylbenzyl | Methoxy | N-Benzoylaminoethyl | 606 | 606 |
| 1127 | 4-Vinylbenzyl | Methoxy | Benzyl | 563 | 563 |
| 1128 | 4-Vinylbenzyl | Methoxy | 4-$NO_2$-benzyl | 608 | 608 |
| 1129 | Piperonylmethyl | Methoxy | 4-Methoxybenzyl | 611 | 611 |
| 1130 | Piperonylmethyl | Methoxy | 3,4-$Cl_2$-benzyl | 635 | 635 |
| 1131 | Piperonylmethyl | Methoxy | 1-Naphthyl | 617 | 617 |
| 1132 | Piperonylmethyl | Methoxy | Piperonyl | 611 | 611 |
| 1133 | Piperonylmethyl | Methoxy | 2,4,5-Trimethoxyphenyl | 657 | 657 |
| 1134 | Piperonylmethyl | Methoxy | 3-Hydroxybenzyl | 597 | 597 |
| 1135 | Piperonylmethyl | Methoxy | 1-Naphthylmethyl | 631 | 631 |
| 1136 | Piperonylmethyl | Methoxy | Phenethyl | 595 | 595 |
| 1137 | Piperonylmethyl | Methoxy | 3-Methoxyphenyl | 597 | 597 |
| 1138 | Piperonylmethyl | Methoxy | N-Benzoylaminoethyl | 624 | 624 |
| 1139 | Piperonylmethyl | Methoxy | Benzyl | 581 | 581 |
| 1140 | Piperonylmethyl | Methoxy | 4-$NO_2$-benzyl | 626 | 626 |
| 1141 | 4-F-benzyl | Methoxy | 4-Methoxybenzyl | 585 | 585 |
| 1142 | 4-F-benzyl | Methoxy | 3,4-$Cl_2$-benzyl | 609 | 609 |
| 1143 | 4-F-benzyl | Methoxy | 1-Naphthyl | 591 | 591 |
| 1144 | 4-F-benzyl | Methoxy | Piperonyl | 585 | 585 |
| 1145 | 4-F-benzyl | Methoxy | 2,4,5-Trimethoxyphenyl | 631 | 631 |
| 1146 | 4-F-benzyl | Methoxy | 3-Hydroxybenzyl | 571 | 571 |
| 1147 | 4-F-benzyl | Methoxy | 1-Naphthylmethyl | 605 | 605 |
| 1148 | 4-F-benzyl | Methoxy | Phenethyl | 569 | 569 |
| 1149 | 4-F-benzyl | Methoxy | 3-Methoxyphenyl | 571 | 571 |
| 1150 | 4-F-benzyl | Methoxy | N-Benzoylaminoethyl | 598 | 598 |

TABLE 3-continued

THE BETA-STRAND MIMETICS LIBRARY

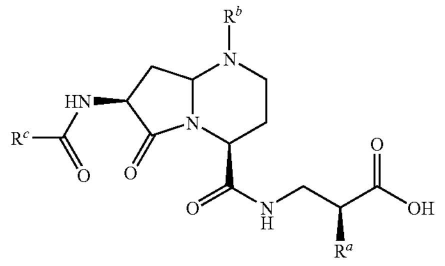

| No. | $R^a$ | $R^b$ | $R^c$ | Mol. Weight | M + H |
|---|---|---|---|---|---|
| 1151 | 4-F-benzyl | Methoxy | Benzyl | 555 | 555 |
| 1152 | 4-F-benzyl | Methoxy | 4-$NO_2$-berizyl | 600 | 600 |
| 1153 | Methyl | Benzyloxy | 4-Methoxybenzyl | 567 | 567 |
| 1154 | Methyl | Benzyloxy | 3,4-$Cl_2$-benzyl | 591 | 591 |
| 1155 | Methyl | Benzyloxy | 1-Naphthyl | 573 | 573 |
| 1156 | Methyl | Benzyloxy | Piperonyl | 567 | 567 |
| 1157 | Methyl | Benzyloxy | 2,4,5-Trimethoxyphenyl | 613 | 613 |
| 1158 | Methyl | Benzyloxy | 3-Hydroxybenzyl | 553 | 553 |
| 1159 | Methyl | Benzyloxy | 1 -Naphthylmethyl | 587 | 587 |
| 1160 | Methyl | Benzyloxy | Phenethyl | 551 | 551 |
| 1161 | Methyl | Benzyloxy | 3-Methoxyphenyl | 553 | 553 |
| 1162 | Methyl | Benzyloxy | N-Benzoylaminoethyl | 580 | 580 |
| 1163 | Methyl | Benzyloxy | Benzyl | 537 | 537 |
| 1164 | Methyl | Benzyloxy | 4-$NO_2$-benzyl | 582 | 582 |
| 1165 | Amino | Benzyloxy | 4-Methoxybenzyl | 568 | 568 |
| 1166 | Amino | Benzyloxy | 3,4-$Cl_2$-benzyl | 592 | 592 |
| 1167 | Amino | Benzyloxy | 1-Naphthyl | 574 | 574 |
| 1168 | Amino | Benzyloxy | Piperonyl | 568 | 568 |
| 1169 | Amino | Benzyloxy | 2,4,5-Trimethoxyphenyl | 614 | 614 |
| 1170 | Amino | Benzyloxy | 3-Hydroxybenzyl | 554 | 554 |
| 1171 | Amino | Benzyloxy | 1-Naphthylmethyl | 588 | 588 |
| 1172 | Amino | Benzyloxy | Phenethyl | 552 | 552 |
| 1173 | Amino | Benzyloxy | 3-Methoxyphenyl | 554 | 554 |
| 1174 | Amino | Benzyloxy | N-Benzoylaminoethyl | 581 | 581 |
| 1175 | Amino | Benzyloxy | Benzyl | 538 | 538 |
| 1176 | Amino | Benzyloxy | 4-$NO_2$-benzyl | 583 | 583 |
| 1177 | 3-Propenyl | Benzyloxy | 4-Methoxybenzyl | 593 | 593 |
| 1178 | 3-Propenyl | Benzyloxy | 3,4-$Cl_2$-benzyl | 617 | 617 |
| 1179 | 3-Propenyl | Benzyloxy | 1-Naphthyl | 599 | 599 |
| 1180 | 3-Propenyl | Benzyloxy | Piperonyl | 593 | 593 |
| 1181 | 3-Propenyl | Benzyloxy | 2,4,5-Trimethoxyphenyl | 639 | 639 |
| 1182 | 3-Propenyl | Benzyioxy | 3-Hydroxybenzyl | 579 | 579 |
| 1183 | 3-Propenyl | Benzyloxy | 1-Naphthylmethyl | 613 | 613 |
| 1184 | 3-Propenyl | Benzyloxy | Phenethyl | 577 | 577 |
| 1185 | 3-Propenyl | Benzyloxy | 3-Methoxyphenyl | 579 | 579 |
| 1186 | 3-Propenyl | Benzyloxy | N-Benzoylaminoethyl | 606 | 606 |
| 1187 | 3-Propenyl | Benzyloxy | Benzyl | 563 | 563 |
| 1188 | 3-Propenyl | Benzyloxy | 4-$NO_2$-benzyl | 608 | 608 |
| 1189 | Ethanoic acid | Benzyloxy | 4-Methoxybenzyl | 611 | 611 |
| 1190 | Ethanoic acid | Benzyloxy | 3,4-$Cl_2$-benzyl | 635 | 635 |
| 1191 | Ethanoic acid | Benzyloxy | 1-Naphthyl | 617 | 617 |
| 1192 | Ethanoic acid | Benzyloxy | Piperonyl | 611 | 611 |
| 1193 | Ethanoic acid | Benzyloxy | 2,4,5-Trimethoxyphenyl | 657 | 657 |
| 1194 | Ethanoic acid | Benzyloxy | 3-Hydroxybenzyl | 597 | 597 |
| 1195 | Ethanoic acid | Benzyloxy | 1-Naphthylmethyl | 631 | 631 |
| 1196 | Ethanoic acid | Benzyloxy | Phenethyl | 595 | 595 |
| 1197 | Ethanoic acid | Benzyloxy | 3-Methoxyphenyl | 597 | 597 |
| 1198 | Ethanoic acid | Benzyloxy | N-Benzoylaminoethyl | 624 | 624 |
| 1199 | Ethanoic acid | Benzyloxy | Benzyl | 581 | 581 |
| 1200 | Ethanoic acid | Benzyloxy | 4-$NO_2$-benzyl | 626 | 626 |
| 1201 | Propionic acid | Benzyloxy | 4-Methoxybenzyl | 625 | 625 |
| 1202 | Propionic acid | Benzyloxy | 3,4-$Cl_2$-benzyl | 649 | 649 |
| 1203 | Propionic acid | Benzyloxy | 1-Naphthyl | 631 | 631 |
| 1204 | Propionic acid | Benzyloxy | Piperonyl | 625 | 625 |
| 1205 | Propionic acid | Benzyloxy | 2,4,5-Trimethoxyphenyl | 671 | 671 |
| 1206 | Propionic acid | Benzyloxy | 3-Hydroxybenzyl | 611 | 611 |
| 1207 | Propionic acid | Benzyloxy | 1-Naphthylmethyl | 645 | 645 |
| 1208 | Propionic acid | Benzyioxy | Phenethyl | 609 | 609 |
| 1209 | Propionic acid | Benzyloxy | 3-Methoxyphenyl | 611 | 611 |

TABLE 3-continued

THE BETA-STRAND MIMETICS LIBRARY

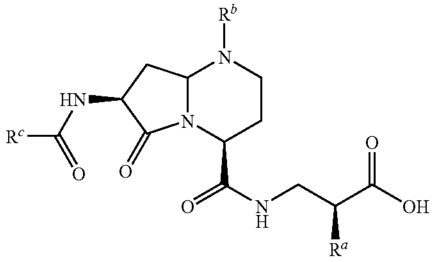

| No. | $R^a$ | $R^b$ | $R^c$ | Mol. Weight | M + H |
|---|---|---|---|---|---|
| 1210 | Propionic acid | Benzyloxy | N-Benzoylaminoethyl | 638 | 638 |
| 1211 | Propionic acid | Benzyloxy | Benzyl | 595 | 595 |
| 1212 | Propionic acid | Benzyloxy | 4-$NO_2$-benzyl | 640 | 640 |
| 1213 | 4-Vinylbenzyl | Benzyloxy | 4-Methoxybenzyl | 669 | 669 |
| 1214 | 4-Vinylbenzyl | Benzyloxy | 3,4-$Cl_2$-benzyl | 694 | 694 |
| 1215 | 4-Vinylbenzyl | Benzyloxy | 1-Naphthyl | 675 | 675 |
| 1216 | 4-Vinylbenzyl | Benzyloxy | Piperonyl | 669 | 669 |
| 1217 | 4-Vinylbenzyl | Benzyloxy | 2,4,5-Trimethoxyphenyl | 715 | 715 |
| 1218 | 4-Vinylbenzyl | Benzyloxy | 3-Hydroxybenzyl | 655 | 655 |
| 1219 | 4-Vinylbenzyl | Benzyloxy | 1-Naphthylmethyl | 689 | 689 |
| 1220 | 4-Vinylbenzyl | Benzyloxy | Phenethyl | 653 | 653 |
| 1221 | 4-Vinylbenzyl | Benzyloxy | 3-Methoxyphenyl | 655 | 655 |
| 1222 | 4-Vinylbenzyl | Benzyloxy | N-Benzoylaminoethyl | 682 | 682 |
| 1223 | 4-Vinylbenzyl | Benzyloxy | Benzyl | 639 | 639 |
| 1224 | 4-Vinylbenzyl | Benzyloxy | 4-$NO_2$-benzyl | 684 | 684 |
| 1225 | Piperonylmethyl | Benzyloxy | 4-Methoxybenzyl | 687 | 687 |
| 1226 | Piperonylmethyl | Benzyloxy | 3,4-$Cl_2$-benzyl | 712 | 712 |
| 1227 | Piperonylmethyl | Benzyloxy | 1-Naphthyl | 693 | 693 |
| 1228 | Piperonylmethyl | Benzyloxy | Piperonyl | 687 | 687 |
| 1229 | Piperonylmethyl | Benzyloxy | 2,4,5-Trimethoxyphenyl | 733 | 733 |
| 1230 | Piperonylmethyl | Benzyloxy | 3-Hydroxybenzyl | 673 | 673 |
| 1231 | Piperonyimethyl | Benzyloxy | 1-Naphthylmethyl | 707 | 707 |
| 1232 | Piperonylmethyl | Benzyloxy | Phenethyl | 671 | 671 |
| 1233 | Piperonylmethyl | Renzyioxy | 3-Methoxyphenyl | 673 | 673 |
| 1234 | Piperonylmethyl | Benzyloxy | N-Benzoylaminoethyl | 700 | 700 |
| 1235 | Piperonylmethyl | Benzyloxy | Benzyl | 657 | 657 |
| 1236 | Piperonylmethyl | Benzyloxy | 4-$NO_2$-benzyl | 702 | 702 |
| 1237 | 4-F-benzyl | Benzyloxy | 4-Methoxybenzyl | 661 | 661 |
| 1238 | 4-F-benzyl | Benzyloxy | 3,4-$Cl_2$-benzyl | 686 | 686 |
| 1239 | 4-F-benzyl | Benzyloxy | 1-Naphthyl | 667 | 667 |
| 1240 | 4-F-benzyl | Benzyloxy | Piperonyl | 661 | 661 |
| 1241 | 4-F-benzyl | Benzyloxy | 2,4,5-Trimethoxyphenyl | 707 | 707 |

The β-strand mimetic structures of the present invention may be used as bioactive agents, such as diagnostic, prophylactic, and therapeutic agents. Preferably, the compounds are formulated into a pharmaceutically acceptable form and then administered to a patient in need of treatment by the β-strand mimetic structures of the present invention.

Thus, the present invention provides a pharmaceutical composition containing a compound of structures (I") through (I'"). For the preparation of the pharmaceutical composition containing the present compounds, a skilled person in the art can use publicly known knowledge and techniques that are known in the pertinent art. Generally known varieties of carriers and other additives are used for the preparation of the composition of the present invention. The pharmaceutical compositions of this invention may be administered in a standard manner for the disease condition that is desired to be treated, for example by oral, rectal or parenteral administration.

For these purposes, the compounds of the present invention may be formulated by means known in the art into a form of, for example, tablets, capsules, aqueous or oily solutions or suspension, (lipid) emulsions, dispersible powders, suppositories, ointments, creams, drops and sterile injectable aqueous or oily solutions or suspensions.

A suitable pharmaceutical composition of the present invention is one suitable for oral administration in unit dosage form such as, for example a tablet or capsule that contains from about 1 mg to about 1 g of the compound of this invention.

In another aspect, a pharmaceutical composition of the present invention is one suitable for intravenous, subcutaneous or intramuscular injection. A patient may receive, for example, an intravenous, subcutaneous or intramuscular dose of about 1 μg/kg to about 1 g/kg of the compound of the present invention. The intravenous, subcutaneous and intramuscular dose may be given by means of a bolus injection. Alternatively the intravenous dose may be given by continuous infusion over a period of time.

Alternatively a patient will receive a daily oral dose which is approximately equivalent to the daily parenteral dose, the composition being administered 1 to about 4 times per day.

The following table illustrates representative pharmaceutical dosage forms containing the compound or pharmaceutically-acceptable salt thereof for therapeutics or prophylactic use in humans:

| | mg/tablet |
|---|---|
| Tablet 1 | |
| Compound | 100 |
| Lactose Ph. Eur. | 179 |
| Croscarmellose sodium | 12.0 |
| Polyvinylpyrrolidone | 6 |
| Magnesium stearate | 3.0 |
| Tablet 2 | |
| Compound | 50 |
| Lactose Ph. Eur. | 229 |
| Croscarmellose sodium | 12.0 |
| Polyvinylpyrrolidone | 6 |
| Magnesium stearate | 3.0 |
| Tablet 3 | |
| Compound | 1.0 |
| Lactose Ph. Fur. | 92 |
| Croscarmellose sodium | 4.0 |
| Polyvinylpyrrolidone | 2.0 |
| Mag nesiumstearate | 1.0 |
| Capsule | mg/capsule |
| Compound | 10 |
| Lactose Ph. Fur. | 389 |
| Croscarmellose sodium | 100 |
| Magnesium stearate | 1.0 |
| Injection I | (50 mg/ml) |
| Compound | 0.5% w/v |
| Isotonic aqueous solution | to 100% |

The pharmaceutical composition containing the compound of general formula (I) can be used for a variety of biologically desirable effects, including inhibiting a protease in a warm-blooded animal, modulating a cell signaling transcription factor related peptide in a warm-blooded animal, and for inhibiting a kinase in a warm-blooded animal. These effects may be achieved by a method comprising administering to the animal in need thereof an effective amount of the compound of formula (I).

Furthermore, and as discussed in detail below, the β-strand mimetic structures of the present invention may also be effective for inhibiting MHC-I and/or MHC-II presentation of peptides to T cell receptors in a warm-blooded animal; for inhibiting peptide binding to SH2 domains in a warm-blooded animal; for inhibiting peptide binding to SH3 domains in a warm-blooded animal; for inhibiting peptide binding to PTB domains in a warm-blooded animal; for modulating G protein coupled receptor (GPCR) and ion channel in a warm-blooded animal; and for modulating cytokines in a warm-blooded animal.

Kinase Inhibition (Including SH2 and SH3 Domain Inhibition)

In one aspect, the present invention provides a method for inhibiting a kinase in a warm-blooded animal. The method comprises administering to the animal an amount of a compound of the present invention, where the amount is effective to inhibit a kinase. Kinases (also known as protein kinases) are a class of enzymes that catalyze a reaction whereby a biomolecule (typically another enzyme) is phosphorylated. As many as 1000 kinases are thought to be encoded in the mammalian genome (Hunter, *Cell* 50: 823-829, 1987). The large number of kinases allow for rapid signal amplification and multiple points of regulation.

Phosophorylation is a very common covalent modification found in signal transduction processes, and causes an alteration in the activity of those proteins which become phosphorylated. Kinases are thus a critical component of signaling pathways. Kinases are typically organized into several modular functional regions, or "domains" (Cohen, G. B., et al. *Cell* 80: 237-248, 1995). One domain, known as "SH3," is a region of 55-70 amino acids that binds to proline-rich peptides, particularly extended strand. Another domain, known as "SH2," is a phosphotyrosine binding region of about 100 amino acids in length. These two domains are believed to be involved in recognizing and binding to the protein substrates. These, as well as other domains including myristoylation and palmitoylation sites, are responsible for assembling multiprotein complexes which guide the catalytic domain to the correct targets (Mayer et al. *Mol. Cell. Biol.* 12: 609-618, 1992; and Mayer and Baltimore, *Mol. Cell. Biol.* 14: 2883-2894, 1994). While SH2 and SH3 domains are known to be present in some kinases, these domains are also present in other proteins. The compounds of the present invention may be used to inhibit SH2- or SH3-mediated binding in kinase or other proteins.

Kinases are used by the body in a vast number of different, but often interrelated, intracellular signal transduction mechanisms. For example, growth factors, transcription factors, hormones, cell cycle regulatory proteins, and many other classes of cellular regulators utilize tyrosine kinases in their signaling cascades (see, e.g., Bolen et al. *FASEB J.* 6: 3403-3409, 1992; and Ullrich and Schlessinger, Cell 61:203-212, 1990). The serine/threonine kinases make up the majority of the remainder of the kinase family.

One important approach for determining the role, and understanding the function, of enzymes, both in vitro and in vivo, is the use of specific enzyme inhibitors. If one or more compounds can be found that will inhibit the enzyme, the inhibitor can be used to modulate the enzyme's activity, and the effects of that decrease can be observed. Such approaches have been instrumental in deciphering many of the pathways of intermediary metabolism, and have also been important in learning about enzyme kinetics and determining catalytic mechanisms. The present invention provides such compounds.

Regulation of many immune responses is mediated through receptors that transmit signals through tyrosine kinases containing SH2 domains. T-cell activation via the antigen specific T-cell receptor (TCR) initiates a signal transduction cascade leading to lymphokine secretion and cell proliferation. One of the earliest biochemical responses following TCR activation is an increase in tyrosine kinase activity. In particular, T-cell activation and proliferation is controlled through T-cell receptor mediated activation of $p56^{lck}$ and $p59^{fyn}$ tyrosine kinases, as well as ZAP-70 and Syk (Weiss and Litman, *Cell* 76: 263-274, 1994) which contain SH2 domains. Additional evidence indicates that several src-family kinases (lck, blk, fyn) participate in signal transduction pathways leading from B-cell antigen receptors and hence may serve to integrate stimuli received from several independent receptor structures. Thus, inhibitors that block interactions of these SH2 domain kinases with their cognate receptors could serve as immunosuppressive agents with utility in autoimmune diseases, transplant rejection or as anti-inflammatory agents as well as anticancer drugs in cases of lymphocytic leukemias.

Additionally, non-transmembrane PTPase containing SH2 domains are known and nomenclature refers to them as SH-PTP1 and SH-PTP2 (Neel, *Cell Biology* 4: 419-432, 1993) SH-PTP1 is identical to PTP1 C, HCP or SHP and SH-PTP2 is also known as PTP1 D or PTP2C. SH-PTP1 is expressed at high levels in hematopoietic cells of all lineages and all stages of differentiation. Since the SH-PTP1 gene was identified as responsible for the motheaten (me) mouse phenotype, this provides a basis for predicting the effects of inhibitors that would block its interaction with its cellular substrates. Thus, inhibition of SH-PTP1 function would be expected to result in impaired T-cell responses to mitogenic stimulation, decreased NK cell function, and depletion of B-cell precursors with potential therapeutic applications as described above.

The ability of a compound of the present invention to bind to the SH2 domain of STAT6, or to bind to the SH2 domain of the protein tyrosine phosphatase SH-PTP1, can be demonstrated by the procedures disclosed by Payne et al., *P.N.A.S. USA* 90: 4902-4906, 1993). Libraries of SH2 binding mimetics may be screened by the procedure of Songyang et al., *Cell* 72: 767-778, 1993. See also by the procedure of Songyang et al., *Current Biology* 4: 973-982, 1994), to test for the ability of a compound to act as a substrate or inhibitor of protein kinases.

Accordingly, in one aspect, the present invention provides a method for inhibiting a phosphatase in a warm-blooded animal, where the method comprises administering to the animal an amount of a compound of the present invention, where the amount is effective to inhibit the phosphatase.

In Type 2 (non-insulin dependent) diabetes, tyrosine phosphatases (PTP-1 b) counter-balance the effect of activated insulin-receptor kinases and may represent important drug targets. In vitro experiments show that injection of PTPase blocks insulin stimulated-phosphorylation of tyrosyl residues on endogenous proteins. Thus, compounds of the invention may be used to modulate insulin action in diabetes In another aspect, the present invention provides a method for inhibiting the binding of a phosphotyrosine residue in a first protein to an SH2 domain of a second protein. The method comprises contacting an amount of a compound of the present invention with a composition comprising the first and second protein. The amount is effective to mitigate the binding between the first and second protein that occurs via the SH2 domain of the second protein and the phosphotyrosine residue of the first protein.

Protease Inhibition

In another aspect, the present invention provides a method for inhibiting a protease in a warm-blooded animal. The method comprises administering to the animal an amount of a compound of the present invention as described herein. The amount is effective to inhibit a protease in the animal. In various embodiments: protease is a serine protease; the protease is a serine protease selected from thrombin, Factor X, Factor IX, Factor VII, Factor XI, urokinase, HCV protease, chymase tryptase and kallikrein; the protease is thrombin; the protease is Factor VII; and the protease is selected from an aspartic, cysteine and metallo protease.

With regard to protease inhibition, Cathepsin B is a lysosomal cysteine protease normally involved in proenzyme processing and protein turnover. Elevated levels of activity have been implicated in tumor metastasis (Sloane, B. F. et al., *Cancer Metastasis Rev.* 9: 333-352, 1990), rheumatoid arthritis (Werb, Z. *Textbook of Rheumatology,* Keller, W. N.; Harris, W. D.; Ruddy, S.; Sledge, C. S., Eds., 1989, W. B. Saunder Co., Philadelphia, PA., pp. 300-321), and muscular dystrophy (Katunuma and Kominami, *Rev. Physiol. Biochem. Pharmacol.* 108: 1-20, 1987).

Calpains are cytosolic or membrane bound $Ca^{++}$-activated proteases which are responsible for degradation of cytoskeletal proteins in response to changing calcium levels within the cell. They contribute to tissue degradation in arthritis and muscular dystrophy (see Wang and Yuen *Trends Pharmacol. Sci.* 15: 412-419, 1994).

Interleukin Converting Enzyme (ICE) cleaves pro-IL-1 beta to IL-1 beta, a key mediator of inflammation, and therefore inhibitors of ICE may prove useful in the treatment of arthritis (see, e.g., Miller B. E. et al., *J. Immunol.* 154: 1331-1338, 1995). ICE or ICE-like proteases may also function in apoptosis (programmed cell death) and therefore play roles in cancer, AIDS, Alzheimer's disease, and other diseases in which disregulated apoptosis is involved (see Barr and Tomei, *Biotechnol.* 12: 487-493, 1994).

HIV protease plays a key role in the life cycle of HIV, the AIDS virus. In the final steps of viral maturation it cleaves polyprotein precursors to the functional enzymes and structural proteins of the virion core. HIV protease inhibitors were quickly identified as an excellent therapeutic target for AIDS (see Huff, J. R., *J. Med. Chem.* 34: 2305-2314) and have already proven useful in its treatment as evidenced by the recent FDA approval of ritonavir, Crixivan, and saquinavir.

Hepatitis C virus (HCV) is the major cause of non-A and non-B hepatitis in the world today. It is estimated to infect up to 50 million people. Currently there is no satisfactory treatment available to halt the progression of this debilitating disease. During the life cycle of the virus, a polyprotein of about 3000 amino acids is produced and is proteolytically cleaved by host and viral proteases to produce the mature viral gene products. A serine proteinase located within the HCV NS3 protein cleaves at four specific sites to produce non-structural proteins considered essential for viral replication. Hence, inhibitors of HCV protease are attractive targets for drug design, and could be of great therapeutic benefit. (Neddermann et al., *Biol. Chem.* 378: 469-476, 1997.)

Angiotensin converting enzyme (ACE) is part of the renin-angiotensin system which plays a central role in the regulation of blood pressure. ACE cleaves angiotensin I to the octapeptide angiotensin II, a potent pressor agent due to its vasoconstrictor activity. Inhibition of ACE has proved therapeutically useful in the treatment of hypertension (Williams, G. H., N. *Engl. J. Med.* 319: 1517-1525, 1989).

Collagenases cleave collagen, the major constituent of the extracellular matrix (e.g., connective tissue, skin, blood vessels). Elevated collagenase activity contributes to arthritis (Krane et al., *Ann. N.Y. Acad. Sci.* 580: 340-354, 1990.), tumor metastasis (Flug and Kopf-Maier, *Acta Anat. Basel* 152: 69-84, 1995), and other diseases involving the degradation of connective tissue.

Trypsin-like serine proteases form a large and highly selective family of enzymes involved in hemostasis/coagulation (Davie and Fujikawa, *Ann. Rev.* 799-829, 1975) and complement activation (Muller-Eberhard, *Ann. Rev. Biochem.* 44: 697-724, 1975). Sequencing of these proteases has shown the presence of a homologous trypsin-like core with amino acid insertions that modify specificity and which are generally responsible for interactions with other macromolecular components (Magnusson et al., *Miami Winter Symposia* 11: 203-239, 1976).

Thrombin, a trypsin-like serine protease, acts to provide limited proteolysis, both in the generation of fibrin from fibrinogen and the activation of the platelet receptor, and thus plays a critical role in thrombosis and hemostasis (Mann, K. G., *Trends Biochem. Sci.* 12: 229-233, 1987). Thrombin exhibits remarkable specificity in the removal of fibrinopeptides A and B of fibrinogen through the selective cleavage of only two Arg-Gly bonds of the one-hundred and eighty-one Arg- or Lys-Xaa sequences in fibrinogen (Blomback, *Blood Clotting Enzymology,* Seeger, W. H. (ed.), Academic Press, New York, 1967, pp. 143-215).

Many significant disease states are related to abnormal hemostasis, including acute coronary syndromes. Aspirin and heparin are widely used in the treatment of patients with acute coronary syndromes. However, these agents have several intrinsic limitations. For example, thrombosis complicating the rupture of atherosclerotic plaque tends to be a thrombin-mediated, platelet-dependent process that is relatively resistant to inhibition by aspirin and heparin (Fuster et al., N. Engl. J. Med. 326:242-50, 1992).

Thrombin inhibitors prevent thrombus formation at sites of vascular injury in vivo. Furthermore, since thrombin is also a potent growth factor which initiates smooth muscle cell proliferation at sites of mechanical injury in the coronary artery, inhibitors block this proliferative smooth muscle cell response and reduce restenosis. Thrombin inhibitors would also reduce the inflammatory response in vascular wall cells (Harker et al., *Am. J. Cardiol.* 75: 122-16B, 1995).

Furthermore, at least two well-defined transcription factors, nuclear factor (NF) κB and activator protein (AP)-1, are regulated by the intracellular reduction-oxidation (redox) state. The regulation of gene expression by the redox state holds promising therapeutic implications. For example, binding sites of the redox-regulated transcription factors NF-κB and AP-1 are located in the promoter region of a large variety of genes that are directly involved in the pathogenesis of diseases, such as AIDS, cancer, atherosclerosis and diabetic complications (Sen and Packer, *FASEB Journal* 10: 709-720, 1996). More specifically, the binding of transcription factors such NF-κB and AP-1 to consensus sites on DNA is driven by oxidant-antioxidant homeostasis, especially by the thiol-disulfide balance.

In the case of NF-κB, a physiologically relevant thiol that plays a crucial role in the regulation of NF-κB function is reduced thioredoxin or a reduced thioredoxin-like protein. Thioredoxin is an important protein oxidoreductase with antioxidant functions. Thioredoxin has been found to upregulate DNA binding of activated NF-κB and thus augments gene expression (Schenk et al., *Proc. Natl. Acad. Sci. USA* 91: 1672-1676, 1994). Thioredoxin has been implicated in reducing activated cytosolic NF-κB (specifically reduction of cys-62), which may thus contribute to its nuclear translocation and DNA binding (Hayashi et at., *J. Biol. Chem.* 268: 11380-11388, 1993).

DNA binding activity of Fos and Jun in the AP-1 complex has also been found to be regulated by the redox state (Abate et al., *Science* 249: 1157-1162, 1990). Each protein contains a single conserved cysteine (flanked by lysine and arginine) in its DNA binding domain. This thiol does not appear to be part of a disulfide bond and may exist as a sulfenic or sulfinic acid in its oxidized form. Ref-1, a bifunctional nuclear protein also possessing endonuclease DNA repair activity, stimulates AP-1 DNA binding by reduction of this regulatory cysteine. A Fos mutant in which the critical cysteine was replaced with serine elicited a threefold increase in AP-1 DNA binding activity and was no longer subject to redox control (Okuno et al., *Oncogene* 8: 695-701, 1993). Hence, since at least four members of the fos family, 3 of the jun family, and at least 4 of the ATF/CREB family of transcription factors all contain this conserved cysteine, redox control of transcription factors appears widespread.

As mentioned above, the regulation of transcription factors such as NF-κB and AP-1 have important therapeutic implications. For example, AP-1 is an important mediator of tumor production (Yoshioka et al., *Proc. Natl. Acad. Sci. USA* 92: 4972-4976, 1995). Thus, compounds that repress AP-1 transcriptional activity have utility in the treatment of cancer. Furthermore, due to its direct role in regulating responses to inflammatory cytokines and endotoxins, the activation of NF-κB plays an important role in the development of chronic diseases such as rheumatoid arthritis and acute conditions such as septic shock. Autoimmune diseases, such as systemic lupus erythromatus (SLE), and Alzheimer's disease are also believed involved in activation of NF-κB. Similarly, NF-κB plays an important role in the activation of HIV gene expression. Further conditions which are believed to involve NF-κB include the flu, atherosclerosis, oncogenesis and ataxia telangiectasia (AT).

Oxidoreductase Inhibition

With respect to regulation of transcription factors, the compounds of this invention regulate transcription factors whose ability to bind to DNA is controlled by reduction of a cysteine residue by a cellular oxidoreductase. In one embodiment, the transcription factor is NF-κB. In this embodiment, the compounds of this invention have activity as mediators of immune and/or inflammatory responses, or serve to control cell growth. In another embodiment, the transcription factor is AP-1, and the cellular oxidoreductase is Ref-1. In this embodiment, the compounds of this invention have activity as anti-inflammatory and/or anticancer agents. In yet further embodiments, the transcription factor is selected from Myb and glucocorticoid receptor. Other transcription factors that may be regulated within the context of this invention also include: those of the NF-κB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43.

Accordingly, in one aspect the present invention provides a method for inhibiting an oxidoreductase in a warm-blooded animal, comprising administering to the animal an amount of a compound of the present invention, where the amount is effective to inhibit the oxidoreductase. Inhibition of oxidoreductase activity can be used as a means to regulate transcription.

CAAX Inhibition

In another aspect, the present invention provides a method for CAAX inhibition in a warm-blooded animal. The method comprises administering to the animal an amount of a compound of the present invention as described herein. The amount is effective to provide CAAX inhibition in the animal.

Ras, the protein product of the ras oncogene, is a membrane bound protein involved in signal transduction regulating cell division and growth. Mutations in the ras gene are among the most common genetic abnormalities associated with human cancers (Barbacid, M. *Annu Rev Biochem* 56: 779-827, 1987). These mutations result in a growth signal that is always "on," leading to a cancerous cell. In order to localize to the cell membrane, Ras requires prenylation of the cysteine within its C-terminal CAAX sequence by farnesyl transferase (FTase) where, in the sequence CAAX, "a" is defined as an amino acid with a hydrophobic side chain and "X" is another amino acid. This post-translational modification is crucial to its activity. Peptidyl inhibitors of FTase with the sequence CaaX have been shown to block or slow the growth of tumors in cell culture and in whole animals (Kohl et al., Science 260: 1934-1937, 1993; Buss and Marsters, *Chemistry and Biology* 2: 787-791, 1995).

Methods to screen for the activity of a compound to inhibit CAAX activity are known in the art. See, e.g., U.S. Pat. No. 6,391,574, which describes a method of identifying a compound which inhibits the proteolytic removal of an AAX tripeptide of a CAAX protein in a cell. See also U.S. Pat. No. 5,990,277, which discloses several suitable assays, and references Gibbs et al., *Cell* 77: 175, 1994; Gibbs, *Cell* 65: 1, 1991; Maltese, FASEB J. 4: 3319, 1990; Moores et al., *J. Biol. Chem.* 266: 14603, 1991; Goldstein et al., *J. Biol. Chem.* 266: 15575, 1991; European Patent 0 461 869 A2; Casey, J. Lipid Res. 33: 1731-1740, 1992; Cox et al., Curr. Opin. Cell Biol. 4: 1008-1016. 1992; Garcia et al., *J. Biol. Chem.* 268: 18415-18418, 1993; Vogt et al., *J. Biol. Chem.* 270: 660-664, 1995; Kohl et al., *Science,* 260: 1934-1937, 1993; Garcia et al., *J. Biol. Chem.,* 268: 18415-18418, 1993; and Vogt et al., *J. Biol. Chem.* 270: 660-664, 1995).

MHC Molecules

In another aspect, the present invention provides a method for inhibiting the binding of an antigenic peptide to either a class one or class two MHC molecule. The method comprises contacting a compound according to the present invention with a composition comprising an antigenic peptide and either a class one or class two MHC molecule. The compound is contacted with the antigen/molecule in an amount effective to reduce the binding affinity between the two species.

An important aspect of the immune system is the T cell response. This response requires that T cells recognize and interact with complexes of cell surface molecules, referred to as human leukocyte antigens ("HLA"), or major histocompatibility complexes ("MHCs"), and peptides (see, e.g., Male et al., Advanced Immunology (J. P. Lipincott Company, 1987). Antigens mobilize an immune response, at least in part, by being ingested by an antigen-presenting cell (APC) which contains on its surface a Class II glycoprotein encoded by a gene in the major histocompatibility complex (MHC). The antigen is then presented to a specific T helper cell in the context of the surface bound MHC glycoprotein, and by interaction of the antigen specific T cell receptor with the antigen—MHC complex, the T helper cell is stimulated to mediate the antigen-specific immune response, including induction of cytotoxic T cell function, induction of B cell function, and secretion of a number of factors aiding and abetting this response. In one aspect of the invention, the MHC molecule is HLA-A2.1, HLA-A1 or HLA-A3.1, or any other HLA allele that is present in melanoma patients.

The ability of a compound of the present invention to bind to MHC I molecules can be demonstrated essentially as described by Elliot et al., Nature 351: 402-406, 1991. Similarly, the ability of a compound of the invention to bind to MHC II molecules can be demonstrated by the procedure of Kwok et al., *J. Immunol.* 155: 2468-2476, 1995.

Protein With 14-3-3 Domain

In another aspect, the present invention provides a method for inhibiting the binding of a first peptide to a second pepetide that comprises a 14-3-3 domain, where the first peptide has a binding affinity to the 14-3-3 domain of the second peptide. The method comprises contacting a compound of the present invention with a composition comprising a (first) peptide that has a binding affinity to the 14-3-3 domain of the second protein.

Proteins having the 14-3-3 domain, and binding partners thereof, have been described in the literature. These peptides may be used in the method of the present invention. See, e.g., Dai and Murakami, *J Neurochem* 2003 January 84(1): 23-34; Lim et al., *J Biol Chem* Oct. 25, 2002, 277(43): 40997-1008; Parvaresch et al., *FEBS Lett* Dec. 18, 2002, 532(3): 357-62; Eilers et al., *Mol Cell Biol* 2002 December ; 22(24): 8514-26; Liu et al., *Cancer Res* Nov. 15, 2002, 62(22): 6475-80; Truong et al., Proteins Nov. 15, 2002, 49(3): 321-5; Birkenfeld et al., *Biochem J* Jan. 1, 2003, 369(Pt 1): 45-54; Espejo et al., *Biochem J* Nov. 1, 2002, 367(Pt 3): 697-702; and Benzing et al., *J Biol Chem* Sep. 6, 2002, 277(36): 32954-62.

In the practice of the methods of this invention, a therapeutically effective amount of a compound of this invention is administered to a warm-blooded animal in need thereof. For example, the compounds of this invention may be administered to a warm-blooded animal that has been diagnosed with, or is at risk of developing, a condition selected from any one or more of Chrohn's disease, asthma, rheumatoid arthritis, ischemia, reperfusion injury, graft versus host disease (GVHD), amyotrophic lateral sclerosis (ALS), Alzheimer's disease, allograft rejection and adult T-cell leukemia.

Tuberous Sclerosis Complex

Patients having tuberous sclerosis complex (TSC) typically develop multiple focal lesions in the brain, heart, kidney and other tissues (see, e.g., Gomez, M. R. *Brain Dev.* 17(suppl): 55-57, 1995). Studies in mammalian cells have shown that overexpression of TSC1 (which expresses hamartin) and TSC2 (which expresses tuberin) negatively regulates cell proliferation and induces $G_1$/S arrest (see, e.g., Miloloza, A. et al., *Hum. Mol. Genet.* 9: 1721-1727, 2000). Other studies have shown that hamartin and tuberin function at the level of the β-catenin degradation complex, and more specifically that these proteins negatively regulate beta-catenin stability and activity by participating in the beta-catenin degradation complex (see, e.g., Mak, B. C., et al. *J. Biol. Chem.* 278(8): 5947-5951, 2003). Beta-catenin is a 95-kDa protein that participates in cell adhesion through its association with members of the membrane-bound cadherin family, and in cell proliferation and differentiation as a key component of the Wnt/Wingless pathway (see, e.g., Daniels, D. L., et al., *Trends Biochem. Sci.* 26: 672-678, 2001). Disruption of this pathway has been shown to be oncogenic in humans and rodents. The present invention provides compounds that modulate β-catenin activity, and particularly its interactions with other proteins, and accordingly may be used in the treatment of TSC.

The following examples are provided for purposes of illustration, not limitation.

EXAMPLES

In the Preparation Examples and Examples, the following abbreviations are used:

BMS: Boron dimethyl sulfide

CbzOSu: Benzyloxycarbonyl N-hydroxysuccinimide

DIC: 1,3-Diisopropylcarbodiimide

DIEA: N,N-Diisopropylethylamine

DIPEA: N,N-Diisopropylethylamine

DMAP: N,N-Dimethylaminopyridine

DMF: Dimethylformamide

DMSO: Dimethyl sulfoxide

EA: Ethyl acetate

EDC: 1-Ethyl-3-(3-dimethylaminopropyl)carbodiimide hydrochloride

EDCI: 1-Ethyl-3-(3-dimethylaminopropyl)carbodiimide hydrochloride

FmocOsu: 9-Fluorenyloxycarbonyl N-hydroxysuccinimide

HATU: [2-(1H-9-azabenzotriazole-1-yl)-1,1,3,3-tetramethyluronium hexaflurophosphate]

Hex.: Hexane

HOBT: N-Hydroxybenzotriazole

MC: Methylene chloride

MeOH: Methanol

-OBn:—O-benzyl

PPTS: Pyridinium p-toluenesulfonate

PyBOP: Benzotriazole-1-yl-oxy-tris-pyrrolidino-phosphonium hexafluorophosphate p-TsOH: p-Toluenesulfonic acid THF: Tetrahydrofuron TLC: Thin Layer Chromatography Preparative Example 1

(1) Preparation of Naphthalene-2-Carboxylic Acid Amide

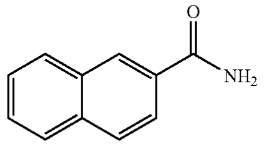

To a solution of 2-naphthoic acid (25 g, 0.145 mol) in MC (200 ml), oxalyl chloride (38 ml, 0.4356 mol) and a catalytic amount of DMF were added and stirred at room temperature for 2 hrs. After the solvent was evaporated, the crude acyl chloride was diluted with MC (200 ml), to which a solution of ammonium hydroxide in water (160 ml) was dropwise added at an ice bath temperature. After stirring for 1 hr, the precipitated product was collected by suction filtration, triturated in hexane and dried to obtain the title compound, which was used next step without further purification.

(2) Preparation of Naphthalene-2-Yl-Methylamine

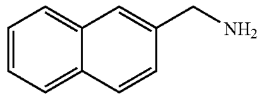

To a solution of the crude amide obtained in the above step (1) in THF (100 ml), BMS (27.5 ml, 0.2904 mol) was slowly added at 0° C. The resulted reaction mixture was heated to 60° C. for 3 hrs, quenched with 5% HCl at 0° C., extracted with EA and washed with 5% HCl. The aqueous layers were combined and basified with 1N NaOH, and again extracted with EA. The organic layers were combined and concentrated to give the title compound (13 g) as white solid.

TLC System 1: MC/MeOH=90:10 v/v; Rf=0.23

$^1$H-NMR (300 MHz, $CDCl_3$) δ ppm: 4.07(s, 2H), 7.48 (m, 3H), 7.79 (m, 4H)

Preparative Example 2

(1) Preparation of 1H—Indole-2-Carboxylic Acid Amide

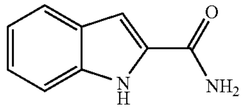

To a solution of indole-2-carboxylic acid (1 g, 6.21 mmol) in MC (30 ml), oxalyl chloride (1.64 ml, 0.18.62 mmol) and a catalytic amount of DMF were added and stirred at room temperature for 2 hrs. After the solvent was evaporated, the crude acyl chloride was diluted with MC (20 ml), to which a solution of ammonium hydroxide in water (7 ml) was dropwise added with cooling in an ice bath. After stirring for 1 hr, the precipitated product was collected by suction filtration, triturated in hexane and dried to give the title compound, which was used in the next step without further purification.

(2) Preparation of (1H—Indol-2-Yl)-Methylamine

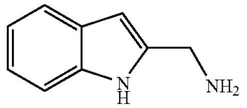

To a solution of the crude amide obtained in the above step (1) in THF (30 ml), BMS (1.18 ml, 12.42 mmol) was slowly added at 0° C. The resulting reaction mixture was heated to 60° C. for 3 hrs, quenched with 5% HCl at 0° C., extracted with EA, and washed with 5% HCl. The aqueous layers were combined and basified with 1N NaOH, and again extracted with EA. The organic layers were combined and concentrated to obtain the title compound (0.28 g) as yellow oil.

TLC System 1: MC/MeOH=90:10 v/v; Rf=0.15

$^1$H-NMR (300 MHz, $CDCl_3$) δ ppm: 3.98(s, 2H), 7.08 (m, 3H), 7.26 (m, 1H), 7.58(d, 1H), 9.10(brs, 1H)

Preparative Example 3

(1) Preparation of 2-Benzyloxycarbonylamino-4-Oxo-Butyric Acid Benzyl Ester

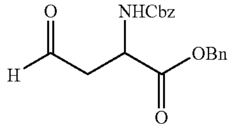

To a solution of Z-Asp-OBn (10 g, 0.028 mol) in MC (200 ml), oxalyl chloride (2.93 ml, 0.0336 mol) and a catalytic amount of DMF were added at 0° C. and stirred at room temperature for 2 hrs. After the solvent was evaporated, the crude acyl chloride was dissolved in benzene (400 ml), and tributyltin hydride (15.1 ml, 0.056 mol) and a catalytic amount of Pd(0) were added slowly at 0° C. and stirred at room temperature overnight. After the solvent was evaporated, ether (100 ml)/10% KF in water (100 ml) was added and stirred at room temperature for 2 hrs, followed by filtration to give a biphasic solution. The organic layer was separated and concentrated to give a crude product, which was purified by column chromatography to obtain the title compound, Z-Asp-OBn aldehyde (6 g) as pale-yellow oil.

Rf: 0.29 in Hexane/EA (2/1)

(2) Preparation of 2-Benzyloxycarbonylamino-4,4-Dimethoxy-Butyric Acid Benzyl Ester

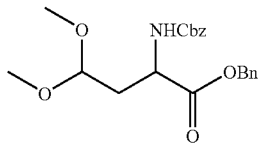

To a solution of Z-Asp-OBn aldehyde (6 g, 17.58 mmol) obtained in the above step (1) in MeOH (100 ml), a catalytic amount of p-TsOH was added and stirred at room temperature for 5 hrs. After the reaction was complete, the solvent was evaporated to give a crude product, which was purified by column chromatography to obtain the title compound, Z-Asp-OBn acetal, (5 g) as pale-yellow oil.

Rf: 0.32 in Hexane/EA (2/1)

(3) Preparation of 2-Benzyloxycarbonylamino-4,4-Dimethoxy-Butyric Acid

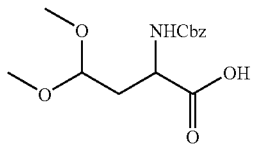

The Z-Asp-OBn acetal (0.5 g, 1.29 mmol) obtained in the above step (2) was dissolved in THF (20 ml)/NaOH (0.11 g, 2.1 mmol) in water (20 ml) and stirred at room temperature for 30 min. After the starting material had disappeared completely, the reaction mixture was concentrated by evaporation and then diluted with water/EA. The aqueous layer was separated, acidified very carefully to pH 4-5 with 1N HCl at 0° C., and again extracted with EA. The organic layers were combined and concentrated to obtain the title compound, Z-Asp-OBn acetal, (0.27 g) as pale-yellow oil.

TLC System 1: Hexane/EA=20:10 v/v; Rf=0.10

$^1$H-NMR (300 MHz, $CDCl_3$) δ ppm: 2.20(s, 2H), 3.35(d, 6H), 4.52 (m, 2H), 5.19(t, 2H), 5.80(d, 1H), 7.37(brs, 5H)

(4) Preparation of 2-Amino-4,4-Dimethoxy-Butyric Acid

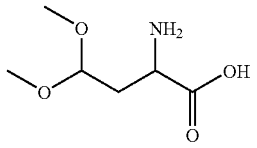

In a reaction vessel equipped with a hydrogen gas balloon, a solution of the Z-Asp-OBn acetal (2.22 g, 5.73 mmol) obtained in the above step (3) in acetic acid (20 ml) and Pearlman's catalyst was added and stirred at room temperature overnight. The resulting reaction mixture was filtered, concentrated and lyophilized to give a crude product, which was used in the next step without further purification.

(5) Preparation of 2-(9H-Fluoren-9-Ylmethoxycarbonylamino)-4,4-Dimethoxy-Butyric Acid

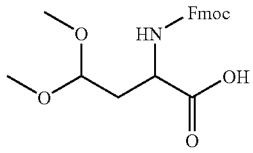

To a solution of the crude Asp-OH acetal obtained in the above step (4) in THF (100 ml)/water (100 ml), FmocOsu (2.13 g, 6.3 mmol)/sodium bicarbonate (1.93 g, 22.92 mmol) was added and stirred at room temperature overnight. The resulting reaction mixture was concentrated and diluted with water/EA. The aqueous layer was separated, acidified very carefully to pH 4-5 with 1N HCl at 0° C., and again extracted with EA. The organic layers were combined and concentrated to give a crude product, which was purified by column chromatography to obtain the title compound (1.5 g) as a foamy solid.

Rf: 0.15 in Hexane/EA (2/1)

Preparative Example 4

(1) Preparation of 2-Benzyloxycarbonylamino-Pentadioic Acid

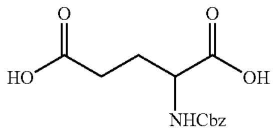

To a solution of L-glutamic acid (20 g, 136 mmol) in water/THF (1/1, 400 ml), sodium bicarbonate (45.7 g, 544 mmol) was added and cooled to 0° C. in an ice bath. To the reaction mixture, CbzOSu (37.3 g, 150 mmol) was added and stirred overnight at room temperature. After the reaction was completed, the resulting reaction mixture was extracted with EA. The aqueous layer was separated, acidified to pH 2 with conc. HCl at 0° C., and again extracted with EA (4 times). The organic layers were concentrated to give a crude product, which was purified by column chromatography to obtain the title compound (16 g) as colorless oil.

Rf: 0.2 in MC/MeOH (9/1)

(2) Preparation of 4-(2-Carboxy-Ethyl)-5-Oxo-Oxazolidine-3-Carboxylic Acid Benzyl Ester

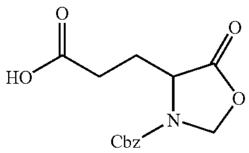

In a Dean-Stark apparatus, N-Cbz-L-glutamic acid (4 g, 14.22 mmol) obtained in the above step (1), paraformaldehyde (5 g), a catalytic amount of pTsOH, molecular sieves (5 g), and toluene (100 ml) were placed and refluxed until the starting material disappeared. The resultant reaction mixture was cooled to room temperature, filtered and concentrated to give a crude product, which was purified by column chromatography to obtain the title compound (2 g) as colorless oil.

Rf: 0.45 in only EA (3) Preparation of 5-oxo-5-(3-Oxo-Propyl)-Oxazolidine-3-Carboxylic Acid Benzyl Ester

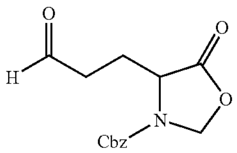

To a solution of the di-protected glutamic acid (2 g, 6.82 mmol) obtained in the above step (2) in MC (200 ml), oxalyl chloride (0.7 ml, 7.5 mmol) and a catalytic amount of DMF were added at 0° C. and stirred at room temperature for 2 hrs. After the solvent was evaporated, the resultant crude acyl chloride was dissolved in THF (400 ml), to which tributyltin hydride (3.86 ml, 14.34 mmol) and a catalytic amount of Pd (0) were slowly added at 0° C. and stirred at room temperature overnight. After the solvent had been evaporated, ether (100 ml)/10% KF in water (100 ml) was added and stirred at room temperature for 2 hrs, followed by filtration to give a biphasic solution. The organic layer was separated and concentrated to give a crude product, which was purified by column chromatography to obtain the title compound (0.7 g) as colorless oil.

Rf: 0.23 in hexane/EA (4/1)

(4) Preparation of 4-(3,3-Dimethoxy-Propyl)5-Oxo-Oxazolidine-3-Carboxylic Acid Benzyl Ester

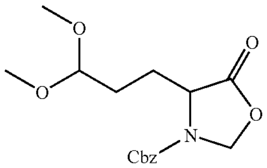

To a solution of di-protected aldehyde (0.7 g, 2.53 mmol) obtained in the above step (3) in MeOH (30 ml), a catalytic amount of pTsOH was added and stirred at room temperature for 7 hrs. After the reaction was complete, the reaction mixture was concentrated by evaporation of solvent to give a crude product, which was purified by column chromatography to obtain the title compound (0.5 g) as colorless oil.

Rf: 0.33 in Hexane/EA (4/1)

(5) Preparation of 2-Benzyloxycarbonylamino-5,5-Dimethoxy-Pentanoic Acid

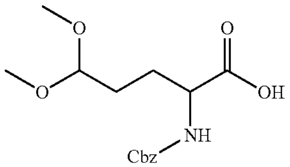

The diprotected acetal (0.456 g, 1.411 mmol) obtained in the above step (4) was dissolved in MeOH (20 ml)/1N NaOH (10 ml) and stirred at room temperature overnight. After the starting material had disappeared completely, the reaction mixture was concentrated by evaporation of solvent and diluted with water/EA. The aqueous layer was separated, acidified very carefully to pH 4-5 with 1N HCl at 0° C., and again extracted with EA. The organic layers were combined and concentrated to obtain the title compound (0.35 g) as colorless oil.

Rf: 0.1 in Hexane/EA (1/1)

(6) Preparation of 2-Amino-5,5-Dimethoxy-Pentanoic Acid

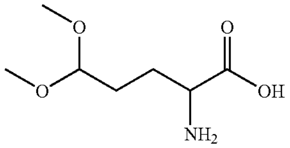

In a reaction vessel equipped with a hydrogen gas balloon, a solution of the Cbz-acetal (0.35 g, 1.13 mmol) obtained in the above step (5) in MeOH (10 ml) and a catalytic amount of 10% Pd/C was added and stirred at room temperature overnight. The resultant reaction mixture was filtered and concentrated to give a crude product (0.2 g) as colorless oil, which was used in the next step without further purification.

Rf: 0.01 in Hexane/EA (1/1)

(7) Preparation of 2-(9H-Fluoren-9-Ylmethoxycarbonylamino)-5,5-Dimethoxy-Pentanoic Acid

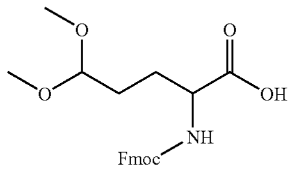

To a solution of the crude Glu-OH acetal obtained in the above step (6) in THF (10 ml)/water (10 ml), FmocOsu (0.42 g, 1.24 mmol)/sodium bicarbonate (0.5 g, 5.9 mmol) was added and stirred at room temperature overnight. After solvent was evaporated, the resultant reaction mixture was diluted with water/EA. The aqueous layer was separated and acidified very carefully to pH 4-5 with 1N HCl at 0° C., and again extracted with EA. The organic layers were combined and concentrated to obtain the title compound (0.19 g) as colorless oil.

TLC System 1: only EA; Rf=0.25

$^1$H-NMR (300 MHz, $CDCl_3$) δ ppm: 1.75(br m, 4H), 3.28 (d, 6H), 3.43(q, 1H), 4.20(t, 1H), 4.38 (m, 3H), 5.62(d, 1H), 7.31 (m, 4H), 7.65(d, 2H), 7.75(d, 2H)

Preparative Example 5

(1) Preparation of 2-Tert-Butoxycarbonylamino-4-Methoxycarbonyl-Amino-Butyric Acid

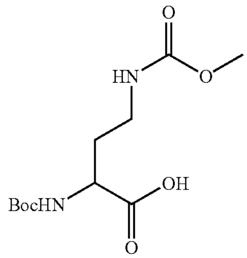

To a solution of Boc-Dab-OH (3 g, 13.75 mmol) in $H_2O$ (50 mL), NaOH (2.75 g, 68.75 mmol, 5 equiv.) was slowly added until pH>11, to which methyl chloroformate (2.6 g, 27.5 mmol, 2 equiv.) in toluene (50 mL) was added. The resultant reaction mixture was stirred for 2 hrs. For the TLC checking, a small amount of aqueous phase was taken out and acidified with 1N HCl. After confirming the reaction completion by TLC, the organic phase was separated and the aqueous phase was acidified with 10% HCl solution and extracted by EA (5 mL X 2). The organic phases were combined, dried over anhydrous $Na_2SO_4$ and concentrated in vacuo to give a crude product (3.277 g, 11.86 mmol, 86%) as a colorless oil.

TLC System: EA only; Rf=0.2

$^1$H-NMR (300 MHz, $CDCl_3$) δ ppm: 1.30~1.50 (bs, 9H), 2.00~2.30 (m, 2H), 3.10~3.30 (m, 2H), 3.70 (bs, 3H), 4.35 (m, 1H), 5.40 (m, 1H), 5.65 (bs, 1H).

(2) Preparation of (1-Benzylcarbamoyl-3-Methoxycarbonylamino-Propyl)-Carbamic Acid Tert-Butyl Ester

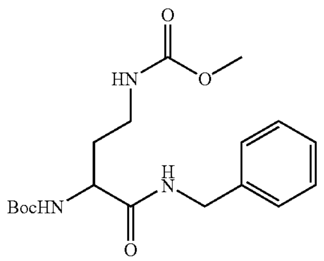

To a solution of 2-tert-Butoxycarbonylamino-4-methoxycarbonylamino-butyric acid (1.1 g, 3.98 mmol) obtained in the above step (1) in DMF (20 mL), EDCI (763 mg, 3.98 mmol, 1 equiv.), HOBT (538 mg, 3.98 mmol, 1 equiv.) and DIEA (1.4 mL, 7.96 mmol, 2 equiv.) were added at 5° C. and stirred for 1 day. After the confirming the reaction completion by the TLC checking, the reaction solution was acidified by 10% HCl at 5° C. (until pH ~4) and extracted by EA (20 mL). The organic phases were combined and washed with sat $NaHCO_3$ and brine, dried over anhydrous $Na_2SO_4$ and concentrated in vacuum to give a residue, which was solidified by adding EA and n-Hexane and purified by column chromatography to obtain the title compound (620 mg, 1.7 mmol, 43%) as a white solid.

Rf=0.7 (EA)

$^1$H-NMR (300 MHz, $CDCl_3$) δ ppm: 1.45 (bs, 9H), 1.75~2.10 (m, 2H), 3.05 (m, 1H), 3.45 (m, 1H), 3.65 (s, 3H), 4.25 (m, 1H), 4.45 (d, 2H, J=5.7 Hz), 5.45 (m, 1H), 7.05 (m, 1H), 7.20~7.45 (m, 5H).

(3) Preparation of (3-Amino-3-Benzylcarbonyl-Propyl)-Carbamic Acid Tert-Butyl Ester Hydrochloride

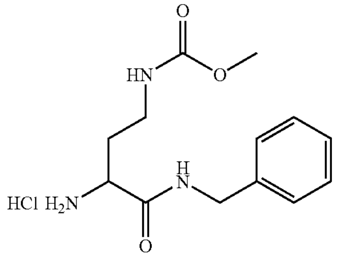

To a solution of (1-Benzylcarbamoyl-3-methoxycarbonylamino-propyl)-carbamic acid tert-butyl ester (1 g, 2.7 mmol) obtained in the above step (2) in 1,4-dioxane (10 mL), 4N HCl in 1,4-dioxane (6.8 mL, 27 mmol) were added and stirred for 2 hours. After the confirming the reaction completion by the TLC checking, the reaction solution was concentrated and dried in vacuum to afford the title compound as a white solid.

Example 1

1-Benzyl-7-Methyl-6-Thioxo-Hexahydro-Pyrimido[1,6-a]Pyrimidin-2-One (A) Preparation of N-Benzyl-3-[3-(2-[1,3]Dioxolan-2-yl-Ethyl)-3Methyl-Thioureido]-propionamide

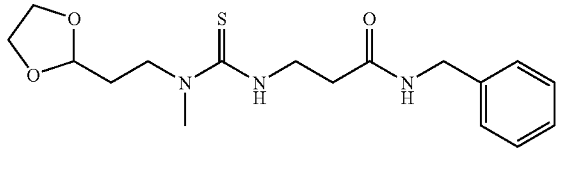

A suspension of β-alanine benzylamido hydrochloride (1.0 eq) and N-methylmorpholine (2.2 eq) in dichloromethane was treated with thiophosgene (1.2 eq) at 0° C. for 10 min. The reaction mixture was allowed to warm to room temperature and stirred for additional 2 hrs. The clear solution was diluted with ethyl acetate and washed with 10% $KHSO_4$ solution, distilled water, and sat. NaCl solution. The organic layer was dried over $Na_2SO_4$ and concentrated to give an oily residue.

This product was dissolved in dichloromethane and treated with 2-(N-methyl-2aminoethyl)-1,3-dioxolane (0.9 eq) at 0° C. for 10 min. The reaction mixture was allowed to warm to room temperature and stirred for additional 4 hrs. The reaction was diluted with ethyl acetate and washed with 10% $KHSO_4$ solution, distilled water, sat. $NaHCO_3$ solution, distilled water, and sat. NaCl solution. The organic layer was dried over $Na_2SO_4$ and concentrated to give an oily residue. This crude product was purified by column chromatography (silica gel, ethyl acetate/hexane=5/2) to give the pure product.

$^1$H-NMR (500 MHz, $CDCl_3$) δ ppm; 2.02 (m, 2H), 2.60 (m, 2H), 3.18 (s, 3H), 3.82 (m, 2H), 3.88 (m, 2H), 4.03 (m, 4H), 4.44 (m, 2H), 4.91 (m, 1H), 6.84 (br.s, 1H), 7.25-7.38 (m, 5H);

MS (m/z, ESI), 352 ($MH^+$)

(B) Preparation of 1-Benzyl-7-Methyl-6-Thioxo-Hexahydro-Pyrimido[1,6-a]Pyrimidin-2-One

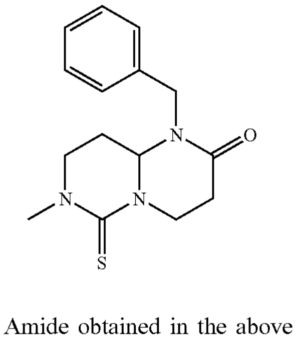

Amide obtained in the above step (A) was treated with formic acid at 60° C. for 4 days. After evaporation of formic acid under reduced pressure, the residue was purified by preparative TLC (silica gel, ethyl acetate/methanol=5/1) to give the pure title product.

$^1$H-NMR (500 MHz, $CDCl_3$) δ ppm: 2.05 (m, 1H), 2.36 (m, 1H), 2.64(d, 1H), 2.96 (m, 1H), 3.30 (m, 3H), 3.44(s, 3H), 4.42(d, 1H), 4.86(br.s, 1H), 5.08(d, 1H), 5.49 (m, 1H) 7.25-7.38 (m, 5H);

MS (m/z, ESI), 290 ($MH^+$), 311 ($M^+Na$)

Example 2

1,7-Dibenzyl-6-Thioxo-Hexahydro-Pyrimido[1,6-a]Pyrimidin-2-One (A) Preparation of N-Benzyl-3-[3-Benzyl-(3,3-Diethoxy-Propyl)-Thioureido]-Propionamide

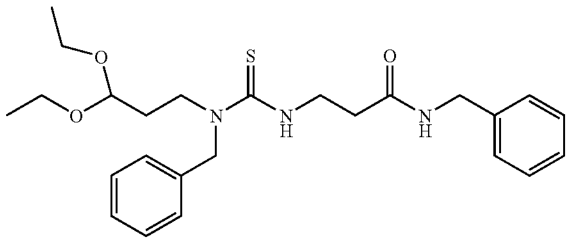

A suspension of α-alanine benzylamido hydrochloride (1.0 eq) and N-methylmorpholine (2.2 eq) in dichloromethane was treated with thiophosgene (1.2 eq) at 0° C. for 10 min. The reaction mixture was allowed to warm to room temperature and stirred for additional 2 hrs. The clear solution was diluted with ethyl acetate and washed with 10% $KHSO_4$ solution, distilled water, and sat. NaCl solution. The organic layer was dried over $Na_2SO_4$ and concentrated to give an oily residue. This product was dissolved in dichloromethane and treated with 2-(N-benzyl-1-amino-3,3-diethoxy propane (0.9 eq) at 0° C. for 10 min. The reaction mixture was allowed to warm to room temperature and stirred for additional 6 hrs. The resulting reaction mixture was diluted with ethyl acetate and washed with 10% $KHSO_4$ solution, distilled water, sat. $NaHCO_3$ solution, distilled water, and sat. NaCl solution. The organic layer was dried over $Na_2SO_4$ and concentrated to give an oily residue. This crude product was purified by column chromatography (silica gel, ethyl acetate/hexane=2/1) to give the pure title product.

$^1$H-NMR (400 MHz, $CDCl_3$) δ ppm; 1.22(t, 6H), 1.95 (m, 2H), 2.60 (m, 2H), 3.46 (m, 2H), 3.60(br. t, 2H), 3.63 (m, 2H), 3.97 (m, 2H), 4.38 (m, 2H), 4.52 (m, 1H), 5.07((br.s, 2H), 6.16(br.s, 1H), 6.98(br.s, 1H), 7.25-7.38 (m, 10H); MS (m/z, ESI), 458($MH^+$)

(B) Preparation of 1,7-Dibenzyl-6-Thioxo-Hexahydro-Pyrimido[1,6-a]Pyrimidin-2-One

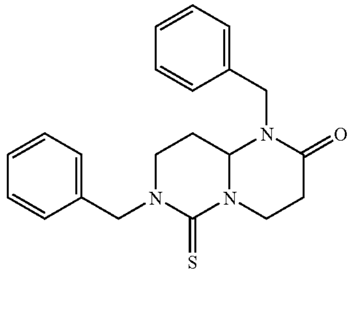

Amide obtained in the above step (A) was treated with formic acid at 60° C. for 4 days. After evaporation of formic acid under reduced pressure, the residue was purified by preparative TLC (silica gel, ethyl acetate/methanol=5/1) to give the pure product.

$^1$H-NMR (500 MHz, $CDCl_3$) δ ppm: 1.94 (m, 1H), 2.24 (m, 1H), 2.62 (m, 1H), 3.01 (m, 1H), 3.18 (m, 1H), 3.43 (m, 1H), 3.62 (m, 1H), 4.39(d, 1H), 4.51 (m, 1H), 4.91 (m, 1H), 5.02(d, 1H), 5.26(d, 1H), 5.53 (m, 1H), 7.25-7.40 (m, 10H);

MS (m/z, APCI), 366($MH^+$)

Example 3

1,7-Dibenzyl-Hexahydro-Pyrimido[1,6-a]Pyrimidin-2,6-Dione (A) Preparation of N-Benzyl-3-[3-Benzyl-(3,3-Diethoxy-Propyl)-Thioureido]-Propionamide

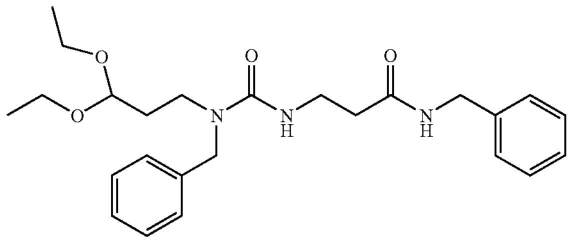

A suspension of β-alanine benzylamido hydrochloride (1.0 eq) and N-methylmorpholine (3.2 eq) in dichloromethane was treated with triphosgene (0.7 eq) at 0° C. for 10 min. The reaction mixture was allowed to warm to room temperature and stirred for additional 2 hrs. The clear solution was diluted with ethyl acetate and washed with 10% $KHSO_4$ solution, distilled water, and sat. NaCl solution. The organic layer was dried over $Na_2SO_4$ and concentrated to give an oily residue. This product was dissolved in dichloromethane and treated with 2-(N-benzyl-1-amino3,3-diethoxy propane (0.9 eq) at 0° C. for 10 min. The reaction mixture was allowed to warm to room temperature and stirred for additional 4 hrs. The resulted reaction mixture was diluted with ethyl acetate and washed with 10% $KHSO_4$ solution, distilled water, sat. $NaHCO_3$ solution, distilled water, and sat. NaCl solution. The organic layer was dried over $Na_2SO_4$ and concentrated to give an oily residue. This crude product was purified by column chromatography (silica gel, ethyl acetate/hexane=2/1) to give the pure title product.

$^1$H-NMR (400 MHz, $CDCl_3$) δ ppm: 1.23(t, 6H), 1.87 (m, 2H), 2.55 (m, 2H), 3.24 (m, 2H), 3.49 (m, 2H), 3.59 (m, 2H), 3.65 (m, 2H), 4.45-4.58 (m, 5H), 5.62(br.s, 1H), 6.57(br.s, 1H), 7.25-7.48 (m, 10H);

MS (m/z, ESI), 442($MH^+$)

(B) Preparation of 1,7-Dibenzyl-Hexahydro-Pyrimido[1,6-a]Pyrimidin-2,6-Dione

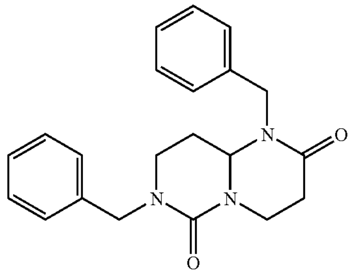

Amide obtained in the above (A) was treated with formic acid at 60° C. for 4 days. After evaporation of formic acid under reduced pressure, the residue was purified by preparative TLC (silica gel, ethyl acetate) to give the titled compound.

$^1$H-NMR (400 MHz, $CDCl_3$) δ ppm; 1.89 (m, 1H), 2.19 (m, 1H), 2.58 (m, 1H), 2.75 (m, 1H), 3.02 (m, 3H), 4.42(d, J=12.4 Hz, 1H), 4.55(d, J=2.4 Hz, 2H), 4.65 (m, 1H), 4.78 (m, 1H), 4.98(d, J=12.4 Hz, 1H), 7.25-7.38 (m, 10H);

MS (m/z, ESI), 350($MH^+$)

Example 4

1,7-Dibenzyl-6-Oxo-Octahydro-Pyrimido[1,6-a]Pyrimidin-2-One (A) Preparation of (3-Bromo-1-Methoxypronpan-1-oxy)-Linked ArgoGel Resin

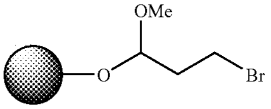

A suspension of dry ArgoGel resin and pyridinium para-toluensulphonate (240 mg, 0.96 mmol) in 1,2-dichloroethane (15 mL) was heated to reflux while continuously removing the solvent and traces of water. After removing about 5 mL of the distillate, a solution of 3-bromo-1,1-dimethoxypropane (700 mg, 3.84 mmol) in 1,2-dichloroethane (5 mL) was added and the mixture was kept at reflux for 4h with continuous removal of EtOH/EDC, after which the resin was washed with DMF and dioxane followed by lyophilization to give the desired product.

(B) Preparation of (3-Benzylamino-1-Methoxypropan-1-oxy)-Linked ArgoGel Resin

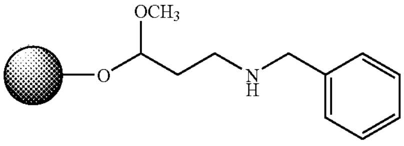

A solution of benzyl amine (520 mg, 4.85 mmol) in DMSO (4 mL) was added to the bromoacetal resin (1 g, 0.48 mmol) and the suspension was shaken at 60° C. for 15 hrs. The resulted resin was filtered, washed with DMSO, MeOH and MC, and dried in vacuo overnight. The secondary amine was detected by chloranil test.

(C) Preparation of β-Alanine Benzyl Amine Urea

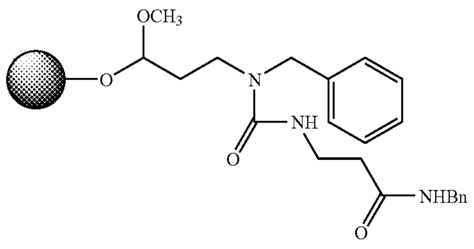

To a solution of β-alanine benzyl amide HCl (80 mg, 0.36 mmol) in N-methyl morpholine (120 μi) and MC (2 mL), triphosgene (0.72 mmol) was added at room temperature. After 10 minutes, the resulted isocyanate solution was added to a suspension of the secondary amine resin obtained in above step (2) (100 mg, 0.048 mmol) and kept shaking for 3 hrs at room temperature. The resin was washed with DMF, MeOH and MC, and the completion of reaction was checked with chloranil test.

(D) Preparation of 1,7-Dibenzyl-6-oxo-Octahydro-Pyrimido [1,6-a]Pyrimidin-2-One

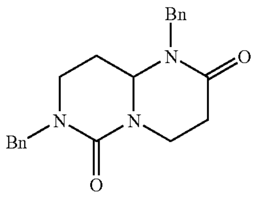

The thiourea group-containing resin of step (C) was treated with formic acid and kept shaking for 15 hrs. The resin was filtered off and the filtrate was concentrated and purified by chromatography (silica gel) to obtain the title compound.

$^1$H-NMR (500 MHz, $CDCl_3$) δ ppm: 1.94 (m, 1H), 2.24 (m, 1H), 2.62 (m, 1H), 3.01 (m, 1H), 3.18 (m, 1H), 3.43 (m, 1H), 3.62 (m, 1H), 4.39(d, 1H), 4.51 (m, 1H), 4.91 (m, 1H), 5.02(d, 1H), 5.26(d, 1H), 5.53 (m, 1H), 7.25-7.40 (m, 1 OH);

MS (m/z, APCI), 366($MH^+$)

Example 5

1,7-Dibenzyl-2-oxo-6-Thioxo-Octahydro-Pyrimido [1,6-a]Pyrimidine-4-Carboxylic Acid Benzyl Ester (A) Preparation of 2-Isothiocyanato-Succinic Acid 1-Benzyl Ester 4-(9H-Fluoren-9-ylMethyl) Ester

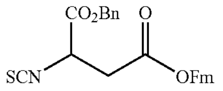

To a solution of 2-tert-butoxycarbonylamino-succinic acid 1-benzyl ester (1 g, 3.09 mmol) in MC, DIC (532 μl, 1.1 eq), DMAP (188 mg, 0.5 eq) and fluorenyl methanol (635 mg, 1.05 eq) were added. After the reaction was completed, the resultant reaction mixture was washed with 1N HCl and sat. $NaHCO_3$ solution, and purified by column chromatography (silica gel) to obtain the fluorenyl methyl ester (400 mg).

This ester was diluted in dioxane (10 ml) and a 4N HCl solution of dioxane was added and kept stirring for 2 hrs to remove the Boc protection group. After completion of the reaction, the solution was evaporated to dryness. The HCl salt of the amine was diluted with MC and N-methyl morpholine, and thiophosgene (1.2 eq) was added at ca. 0° C. After the reaction was complete, the mixture was washed with 10% $KHSO_4$ solution, distilled water, sat. $NaHCO_3$ solution, distilled water, and sat. NaCl solution. The organic layer was dried over $Na_2SO_4$ and concentrated to give an oily residue. This crude product was purified by column chromatography (silica gel, ethyl acetate/hexane=1/1) to give the pure title product.

(C) Aspartic Acid Benzyl, Fluorenyl Ester Thiourea

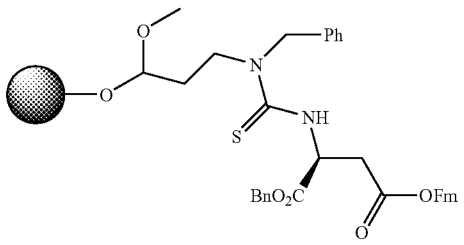

A MC solution of the isocyanate (0.5 mmol) obtained in the above step (A) with N-methyl morpholine was added to a suspension of the secondary amine resin (200 mg, 0.04 mmol) as obtained in step (B) of Example 4 and kept shaking for 3 hrs at room temperature. The resultant resin was washed with DMF, MeOH and MC, and the completion of reaction was checked with chloranil test.

(C) Aspartic Acid Thiourea Benzylamide

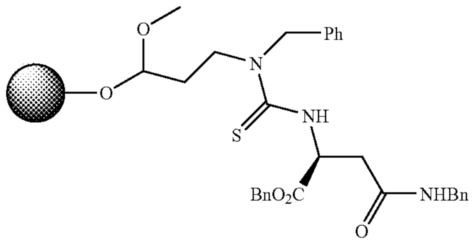

The resin obtained in the above step (C) was swelled for 30 min in DMF (4 mL), and a 25% piperidine solution was added to cleave the fluorenyl methyl protection. The resultant resin was washed with DMF, MeOH and MC. The resin was dried under reduced pressure and swelled again, to which DIC (8 μL, 0.05 mmol), HOBt (8 mg, 0.05 mmol) and DIEA (18 μL, 0.1 mmol) were added to activate the acid. After shaking for 30 min, benzyl amine was added and kept shaking overnight to obtain the desired benzyl amide resin.

(D) Preparation of 1,7-Dibenzyl-2-oxo-6-Thioxo-Octahydro-Pyrimido[1,6-a]Pyrimidine-4-Carboxylic Acid Benzyl Ester

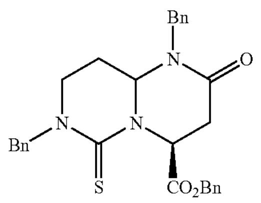

The resin obtained in the above step (C) was swelled in MC (4 mL), to which PPTS (10 mg) was added and heated for 4 hrs at 60° C. to obtain the title compound. MS (m/z, ESI), 500 ($MH^+$).

Example 6

7-Benzyl-6-Thioxo-Hexahydro-Pyrimido[1,6-a]Pyrimidine-1-Carboxylic Acid Benzyl Ester (A) Preparation of {3-[3-Benzyl-3-(3,3-Diethoxy-Propyl)-Thioureido]-Propyl}-Carbamic Acid Benzyl Ester

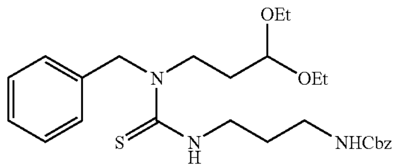

A suspension of Cbz-diamino propane HCl (1.0 eq) and N-methylmorpholine (2.2 eq) in MC was treated with thiophosgene (1.2 eq) at 0° C. for 10 min. The resulting solution was allowed to warm to room temperature and stirred for additional 2 hrs. The resulting clear solution was diluted with ethyl acetate and washed with 10% $KHSO_4$, water, and sat. NaCl. The organic layer was dried over $Na_2SO_4$ and concentrated to give an oily residue, which was dissolved in MC and treated with N-benzyl-1-amino-3,3-diethoxy propane (0.9 eq) at 0° C. for 10 min, and then allowed to warm to room temperature and stirred for additional 6 hrs. The resulting reaction mixture was diluted with ethyl acetate and washed with 10% $KHSO_4$ solution, water, sat. $NaHCO_3$, water, and sat. NaCl. The organic layer was dried over $Na_2SO_4$ and concentrated to give an oily residue, which was then purified by column chromatography (silica gel, ethyl acetate/hexane, 2/1) to give the title compound.

$^1$H-NMR (400 MHz, $CDCl_3$) δ ppm: 1.17 (t, 6H), 1.5 (bs, 2H), 1.75(t, 2H), 1.92 (m, 2H), 3.20 (q, 2H), 3.45 (m, 2H), 3.60 (m, 4H), 3.75 (q, 2H), 4.51 (t, 1H), 5.06 (s, 4H), 6.75 (br.s, 1H), 7.25-7.38 (m, 10H);

MS (m/z, ESI), 442 ($M-OEt^+$).

(B) Preparation of 7-Benzyl-6-Thioxo-Hexahydro-Pyrimido[1,6-a]Pyrimidine-1-Carboxylic Acid Benzyl Ester

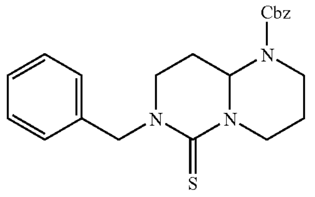

To a solution of the amide obtained in the above step (A) in MC, PPTS was added and stirred at 70° C. overnight. The resulting reaction mixture was concentrated under a reduced pressure to give a residue, which was purified by preparative TLC (ethyl acetate only) to obtain the title compound.

$^1$H-NMR (400 MHz, $CDCl_3$) δ ppm: 1.89 (m, 2H), 1.95 (m, 1H), 2.63 (m, 1H), 2.80 (m, 1H), 3.10 (m, 1H), 3.45 (m, 1H), 3.89 (m, 1H), 4.01 (m, 1H), 4.39(d, 1H), 4.51 (m, 1H), 4.92 (m, 2H), 5.10 (m, 2H), 7.16-7.4 (m, 10H);

MS (m/z, ESI): 396($MH^+$)

Example 7

8-Acetyl-6-Oxo-Hexahydro-Pyrazino[1,2-a]Pyrimidine-1-Carboxylic Acid Benzyl Ester (A) Preparation of [Acetyl-(2,2-Dimethoxy-Ethyl)-Amino]-Acetic Acid

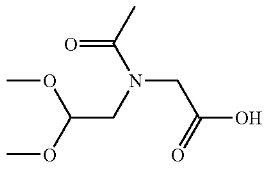

To a solution of benzyl glycine HCl salt (1 eq) in MeOH, dimethoxy acetaldehyde (1.05 eq) and then $NaCNBH_3$ (1.2 eq) were added at room temperature and stirred for 5 hrs. The resulting reaction mixture was concentrated under reduced pressure to give an oily residue, which was dissolved in MC and washed with sat. $NaHCO_3$ solution, water, and sat. NaCl solution. The organic layer was dried over $Na_2SO_4$ and concentrated to give an oily residue, which was dissolved in MC and treated with triethyl amine (3eq) and acetyl chloride (1.1eq) at 0° C.

After the reaction was complete, the resulting reaction mixture was washed with sat. $NaHCO_3$ solution, water, and sat. NaCl solution. The organic layer was dried over $Na_2SO_4$ and concentrated to give an oily residue, which was purified by column chromatography (silica gel, ethyl acetate) to give the pure product. This product was hydrogenolyzed with 10% Pd/C and an $H_2$-containing balloon to obtain the title compound, which was used in the next step without further purification.

$^1$H-NMR (400 MHz, $CDCl_3$) δ ppm: 2.09(s, 1H), 2.20 (s, 2H), 3.40 (d, 6H), 3.48 (d, 2H), 4.16 (s, 2H), 4.44 (m, 1H)

(B) Preparation of (3-{2-[Acetyl-(2,2-Dimethoxy-Ethyl)-Amino]-Acetylamino}-Propyl)-Carbamic Acid Benzyl Ester

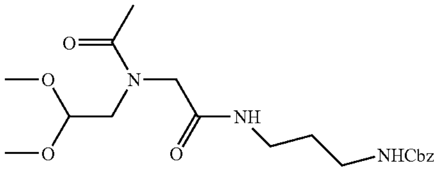

To a solution of the acid (1 eq) obtained in the above step (A) in MC, HATU (1 eq), DIPEA (3 eq) and Cbz-diamino propane HCl (1.0 eq) were added and stirred for 3 hrs at room temperature. The reaction mixture was concentrated under a reduced pressure to give an oily residue, which was purified by preparative TLC to obtain the title compound.

$^1$H-NMR (400 MHz, $CDCl_3$) δ ppm: 1.60 (m, 2H), 2.01(s, 1H), 2.20 (s, 2H), 3.20(d, 2H), 3.24 (m, 2H), 3.40 (d, 6H), 3.50(d, 2H), 4.06 (s, 2H), 4.44 (m, 1H), 5.08(s, 2H), 5.18(d, 1H), 6.91(brd, 1H), 7.16(brs, 5H);

MS (m/z, ESI): 396($MH^+$)

(C) Preparation of 8-Acetyl-6-oxo-Hexahydro-Pyrazino[1,2-a]Pyrimidine-1-Carboxylic Acid Benzyl Ester

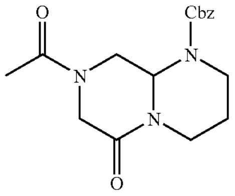

To a solution of the Cbz protected amide precursor obtained in the above step (B) in MC, PPTS (1 eq.) was added at room temperature and heated to 70° C. for 5 hrs. The resulting reaction mixture was concentrated to give a residue, which was characterized as follows.

$^1$H-NMR (400 MHz, $CDCl_3$) δ ppm: 1.90 (m, 2H), 2.10(s, 1H), 2.30 (s, 2H), 2.61 (m, 1H), 2.82 (m, 1H), 3.15 (m, 1H) 3.50 (m, 1H), 3.9 (m, 1H), 4.0 (m, 1H), 4.2 (m, 1H), 4.3(s, 1H), 4.47 (m, 1H), 5.08-5.18 (m, 2H), 5.28(br s, 1H), 7.16(br s, 5H);

MS (m/z, ESI): 332($MH^+$)

Example 8

7-Benzoylamino-4-Benzylcarbamoyl-6-Oxo-Hexahydro-Pyrrolo[1,2-a]Pyrimidine-1-Carboxylic Acid Methyl Ester (A) Preparation of [1-(1-Benzylcarbamoyl-3-Methoxycarbonylamino-Propylcarbamoyl)-3,3-Dimethoxy-Propyl]-Carbamic Acid Benzyl Ester

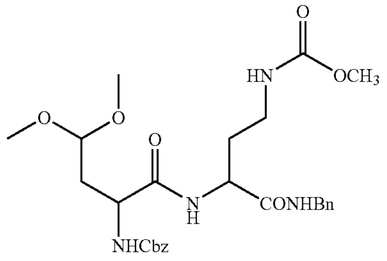

To a solution of the Cbz protected amino acid acetal (100 mg, 1.3eq) obtained in the Preparative Example 3(3) in MC, PyBOP (1 eq to acid), DIPEA (6 eq to acid) and HOBt (1.3 eq) were added and stirred for 30 min. To the reaction mixture, amino benzyl amide HCl salt (71 mg, 0.27 mmol) was added and stirred for 7 hrs. The resulting reaction mixture was washed with sat. $NaHCO_3$, water, and sat. NaCl. The organic layer was dried over $MgSO_4$ and concentrated to give an oily residue, which was purified by column chromatography (silica gel, ethyl acetate) to obtain the title compound (50 mg, yield: 35%).

$^1$H-NMR (300 MHz, $CDCl_3$) δ ppm: 2.1(t, 2H), 3.05 (m, 1H), 3.50(ss, 6H), 3.45 (m, 1H), 3.75(s, 3H), 4.25(q, 1H), 4.41 (m, 2H), 4.55 (m, 1H), 5.0(q, 2H), 5.3 (m, 1H), 5.95 (m, 1H), 7.2-7.4 (m, 10H)

(B) Preparation of 4-Benzylcarbamoyl-7-Benzyloxycarbonylamino-6-oxo-Hexahydro-Pyrrolo[1,2-a]Pyrimidine-1-Carboxylic Acid Methyl Ester

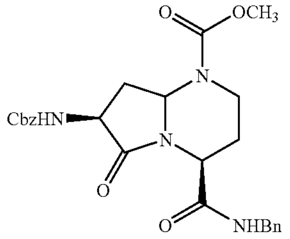

The acetal amide cyclization precursor (5 mg, 0.009 mmol) obtained in the above step (A) was dissolved in formic acid (1 mL) and stirred overnight. The resulting reaction mixture was concentrated to dryness, which is used in the next step without further purification.

$^1$H-NMR (300 MHz, $CDCl_3$) δ ppm: 2.25 (m, 2H), 2.61(t, 2H), 3.24 (m, 1H), 3.50(s, 3H), 3.55 (m, 1H), 3.95 (m, 1H), 4.45 (m, 2H), 4.65(d, 1H), 4.8 (m, 2H), 5.3 (m, 1H), 5.7(d, 1H), 7.15-7.4 (m, 10H), 7.85 (m, 1H)

(C) Preparation of 7-Benzoylamino-4-Benzylcarbamoyl-6-oxo-Hexahydro-Pyrrolo[1,2-a]Pyrimidine-1-Carboxylic Acid Methyl Ester

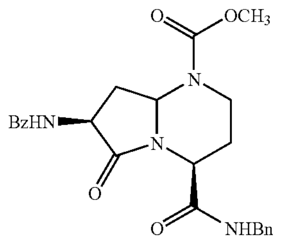

In a reaction vessel equipped with a hydrogen gas balloon, a solution of the Cbz bicyclic ring compound obtained in the above step (B) in MeOH and Pd/C (1 mg) were placed at room temperature and stirred for 2 hrs. After the reaction was complete, the reaction mixture was filtered by celite filter to remove Pd/C and the solvent was evaporated under reduced pressure. The resulting oily residue was dissolved in MC, to which a solution of benzoic acid (1.1 eq) in MC and PyBOP (1.1 eq), HOBt (1.1 eq) and DIPEA (3 eq) were added and stirred for 30 min. To the resulting solution of the activated acid, an amine solution was added and kept stirring for 3 hrs. The resulting reaction mixture was concentrated under reduced pressure to give oily residue, which was purified by preparative TLC to obtain the title compound.

$^{1}$H-NMR (300 MHz, $CDCl_3$) δ ppm: 2.25 (m, 2H), 2.65 (m, 2H), 3.27 (m, 1H), 3.70(s, 3H), 3.6 (m, 1H), 4.10 (m, 1H), 4.54 (m, 2H), 4.8(t, 1H), 5.45 (m, 1H), 7.15-7.42 (m, 10 H), 7.9(d, 1H), 8.31 (t, 1H)

Example 9

Figure 3:
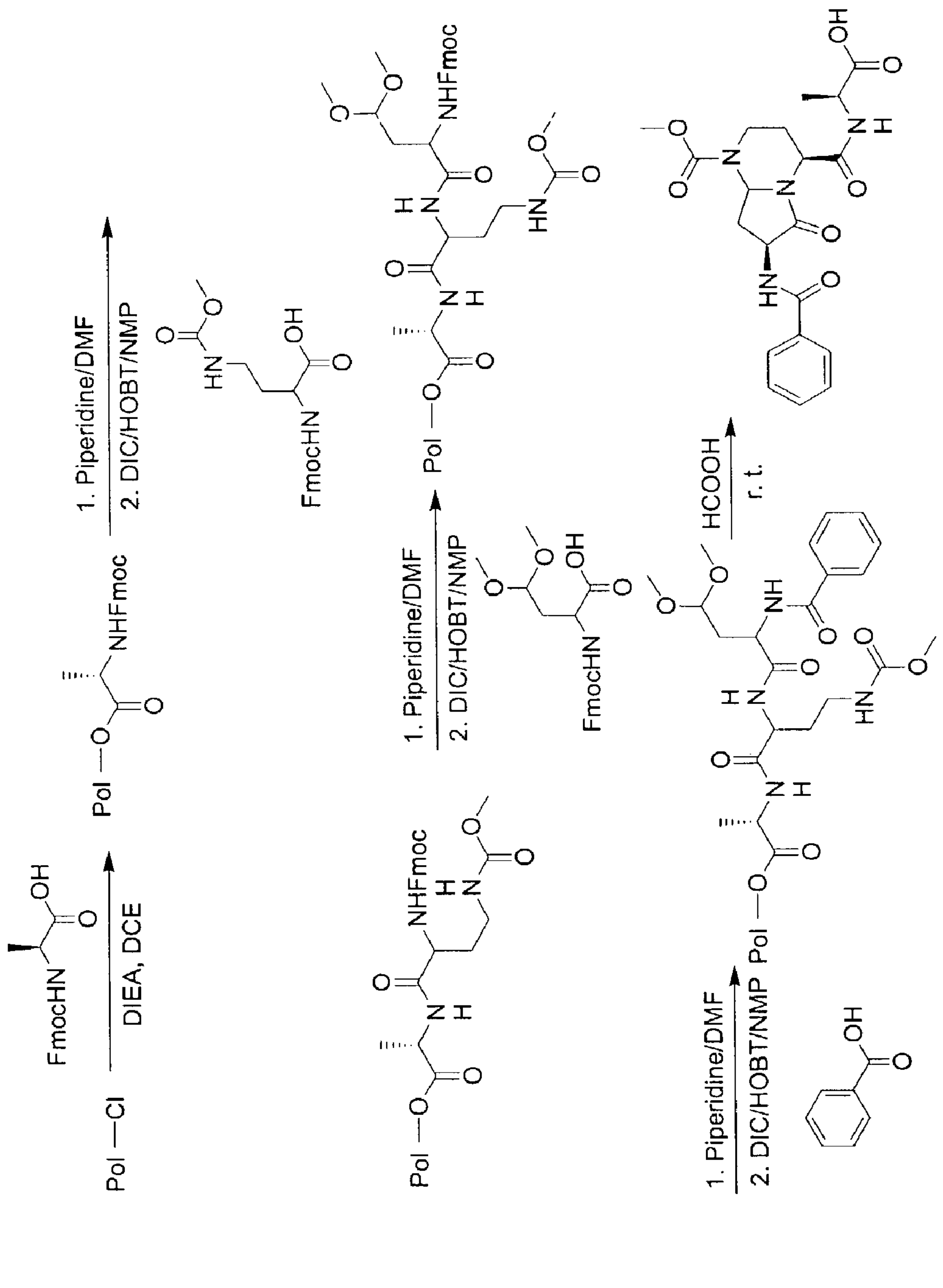
FIG. 3 illustrates synthetic methodology for preparing a library of the present invention, and compounds of the present invention, as more thoroughly described in Example 9.

7-Benzoylamino -4-(1-Carboxy -Ethylcarbamoyl)-6-Oxo-Hexahydro-Pyrrolo[1,2-a ]Pyrimidine -1-Carboxylic Acid Methyl Ester A synthetic scheme showing the methodology of Example 9 is presented in FIG. 3.

2-Chlorotrityl chloride resin (200 mg, 1 mmol/g) and a solution of Fmoc-Alanine (1.5 equiv. commercially available) and DIEA (2 equiv.) in DCE (2 mL) were placed in vial with screw cap. The reaction mixture was shaken at room temperature for 12 hours. The resin was collected by filtration and washed with DMF, MeOH, and then DCM, to provide a first component piece.

To the resin swollen by DMF before reaction was added 25% piperidine in DMF. Thereafter, the reaction mixture was shaken for 30 min at room temperature. The deprotection step was repeated and then the product mixture was washed with DMF, MeOH, and then DCM. A solution of 2-(9H-fluoren-9-ylmethoxycarbonylamino)-4-methoxycarbonylamino-butyric acid (1.5 equiv. $2^{nd}$ component piece), DIC (1.5 equiv.), HOBT (1.5 equiv.) in NMP was added to the resin. After the reaction mixture was shaken for 12 hours at room temperature, the resin was washed with DMF, MeOH, and then DCM.

To the resin swollen by DMF before reaction was added 25% piperidine in DMF. Thereafter, the reaction mixture was shaken for 30 min at room temperature. The deprotection step was repeated and the product mixture was washed with DMF, MeOH, and then DCM. A solution of 2-(9H-fluoren-9yl-methoxycarbonylamino)-5,5-dimethoxy-pentanoic acid (1.5 equiv.), DIC (1.5 equiv.), HOBT (1.5 equiv.) in NMP was added to the resin. After the reaction mixture was shaken for 12 hours at room temperature, the resin was washed with DMF, MeOH, and then DCM.

To the resin swollen by DMF before reaction was added 25% piperidine in DMF. Thereafter, the reaction mixture was shaken for 30 min at room temperature. The deprotection step was repeated and then the product mixture was washed with DMF, MeOH, and then DCM. A solution of commercially available benzoic acid (1.5 equiv.), DIC (1.5 equiv.), HOBT (1.5 equiv.) in NMP was added to the resin. After the reaction mixture was shaken for 12 hours at room temperature, the resin was washed with DMF, MeOH, and then DCM.

The resin was treated with formic acid (1.2 mL each well) for 18 hours at room temperature. Thereafter, the resin was removed by filtration and the filtrate was condensed under reduced pressure to give the product as oil.

$^{1}$H-NMR (300 MHz, MeOH-$d_4$) δ 1.40 (d, 3H), 1.90 (m, 1H), 2.20 (m, 1H), 2.30~2.50 (m, 2H), 3.15 (m, 1H), 3.20 (m, 1H), 3.45 (s, 3H), 3.40~3.60 (m, 1H), 4.20~4.40 (m, 2H), 4.70 (t, 1H), 5.40 (t, 1H), 7.25~7.45 (m, 3H), 7.75 (d, 2H);

MS(m/z, ESI) 433 ($MH^+$), 455 ($MNa^+$)

Example 10

Figure 4:
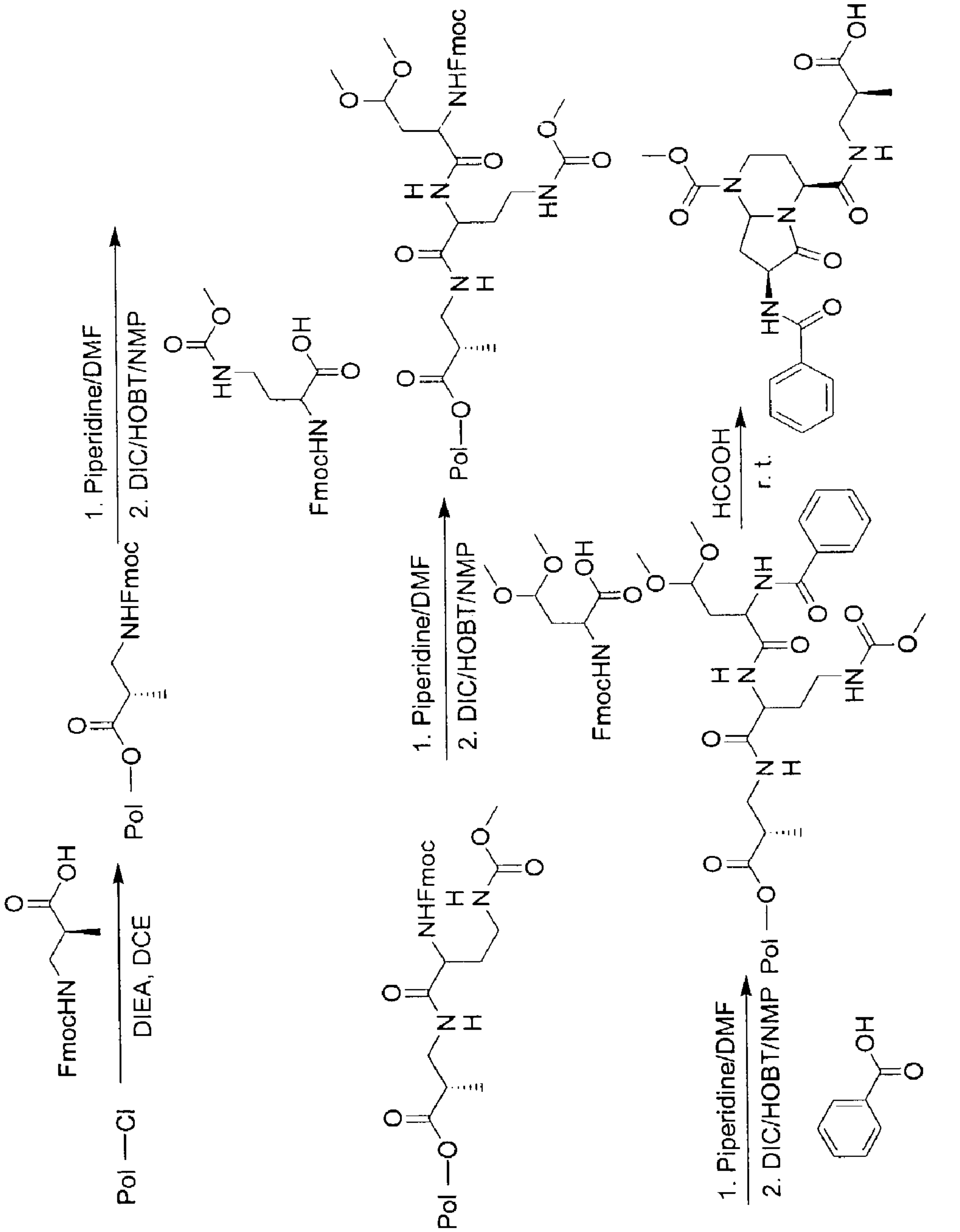
FIG. 4 illustrates synthetic methodology for preparing a library of the present invention, and compounds of the present invention, as more thoroughly described in Example 10.

7-Benzoylamino-4-(2-Carboxy-Propylcarbamoyl)-6-Oxo-Hexahydro-Pyrrolo[1,2-a]Pyrimidine-1-Carboxylic Acid Methyl Ester A synthetic scheme showing the methodology of Example 10 is presented in FIG. 4.

2-Chlorotrityl chloride resin (200 mg, 1 mmol/g) and a solution of Fmoc-beta-alanine (1.5 equiv.) and DIEA (2 equiv.) in DCE (2 mL) were placed in a vial with screw cap. The reaction mixture was shaken at room temperature for 12 hours. The resin was collected by filtration and washed with DMF, MeOH, and then DCM, to provide a first component piece.

To the resin swollen by DMF before reaction was added 25% piperidine in DMF. Thereafter, the reaction mixture was shaken for 30 min at room temperature. The deprotection step was repeated and the product mixture was washed with DMF, MeOH, and then DCM. A solution of 2-(9H-fluoren-9yl-methoxycarbonylamino)-4-methoxycarbonylamino-butyric acid (1.5 equiv. $2^{nd}$ component piece), DIC (1.5 equiv.), and HOBT (1.5 equiv.) in NMP was added to the resin. After the reaction mixture was shaken for 12 hours at room temperature, the resin was washed with DMF, MeOH, and then DCM.

To the resin swollen by DMF before reaction was added 25% piperidine in DMF. Thereafter, the reaction mixture was shaken for 30 min at room temperature. The deprotection step was repeated and then the product mixture was washed with DMF, MeOH, and then DCM. A solution of 2-(9H-fluoren-9-ylmethoxycarbonylamino)-5,5-dimethoxy-pentanoic acid (1.5 equiv.), DIC (1.5 equiv.), and HOBT (1.5 equiv.) in NMP was added to the resin. After the reaction mixture was shaken for 12 hours at room temperature, the resin was washed with DMF, MeOH, and then DCM.

To the resin swollen by DMF before reaction was added 25% piperidine in DMF. Thereafter, the reaction mixture was shaken for 30 min at room temperature. The deprotection step was repeated and then the product mixture was washed with DMF, MeOH, and then DCM. A solution of commercially available benzoic acid (1.5 equiv.), DIC (1.5 equiv.), and HOBT (1.5 equiv.) in NMP was added to the resin. After the reaction mixture was shaken for 12 hours at room temperature, the resin was washed with DMF, MeOH, and then DCM.

The resin was treated with formic acid (1.2 mL in each well) for 18 hours at room temperature. After the resin was removed by filtration, the filtrate was condensed under reduced pressure to give the product as oil.

$^1$H-NMR (300 MHz, MeOH-$d_4$) δ 1.40 (d, 3H), 1.90 (m, 1H), 2.20 (m, 1H), 2.30~2.50 (m, 2H), 3.15 (m, 2H), 3.35 (s, 3H), 3.40~3.60 (m, 3H), 4.20~4.40 (m, 2H), 4.70 (t, 1H), 5.40 (t, 1H), 7.25~7.45 (m, 3H), 7.75 (d, 2H);

MS(m/z, ESI): 447 ($MH^+$), 469 ($MNa^+$)

Various references are set forth herein, which describe in detail certain procedures, compounds and/or compositions, and are incorporated by reference in their entirety.

It will be appreciated that, although specific embodiments of the invention have been described herein for the purposes of illustration, various modifications may be made without departing from the spirit and scope of the invention. Accordingly, the invention is not limited except by the appended claims.

We claim:

1. A compound having the following structure:

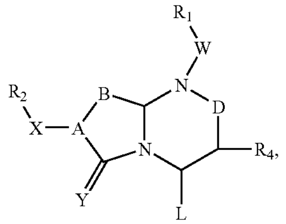

wherein

A is —(CH),

B is —($CH_2$)—or —($CH_2$—$CH_2$)—,

D is ($CH_2$)—,

W is —(C═O)—, or a bond,

X is —NH(C═O)—,

Y is oxygen or sulfur,

L is —C(═O)$NHR_3$, $R_4$ is hydrogen, and $R_1$, $R_2$, and $R_3$, are the same or different and independently selected from hydrogen, an amino acid side chain moiety, $C_{1-12}$ alkyl, $C_{6-12}$ aryl, $C_{7-12}$ arylalkyl, substituted $C_{1-12}$ alkyl, substituted $C_{6-12}$ aryl, substituted $C_{7-12}$ arylalkyl, amino$C_{2-5}$alkyl, guanidino$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy, phenyl, substituted phenyl (where the substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), benzyl, substituted benzyl (where the substituents on the benzyl are independently selected from one or more of amino, amidino, guanidino, hydrazino, amidrazonyl, $C_{1-4}$alkylamino, $C_1$ dialkylamino, halogen, perfluoro $C_{1-4}$alkyl, $C_{1-3}$alkoxy, nitro, carboxy, cyano, sulfuryl, or hydroxyl), naphthyl, substituted naphthyl (where the substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), bis-phenyl methyl, substituted bis-phenyl methyl (where the substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), pyridyl, substituted pyridyl (where the substituents are independently selected from one or more of amino amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), pyrimidyl$C_{1-4}$alkyl, substituted pyrimidyl$C_{1-4}$alkyl (where the pyrimidine substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), triazin-2-yl-$C_{1-4}$alkyl, substituted triazin-2-yl-$C_{1-4}$alkyl (where the triazine substituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), imidazo$C_{1-4}$alkyl, substituted imidazol $C_{1-4}$alkyl (where the imidazole sustituents are independently selected from one or more of amino, amidino, guanidine, hydrazine, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, or hydroxyl), imidazolinyl$C_{1-4}$alkyl, N-amidinopiperazinyl-N-$C_{0-4}$alkyl, hydroxy$C_{2-5}$alkyl, $C_{1-5}$alkylamino $C_{2-5}$alkyl, $C_{1-5}$dialkyl-amino$C_{2-5}$alkyl, N-amidinopiperidinyl$C_{1-4}$alkyl, and 4-aminocyclohexyl$C_{0-2}$alkyl.

2. The compound of claim 1 wherein B is —($CH_2$)—, and the compound has the following structure:

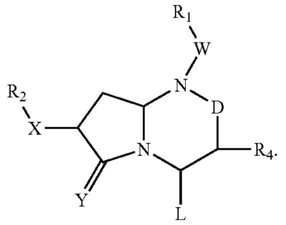

3. The compound of claim 2 wherein Y is oxygen.

4. A pharmaceutical composition comprising a compound of claim 1 and a pharmaceutically acceptable carrier.

* * * * *

UNITED STATES PATENT AND TRADEMARK OFFICE

CERTIFICATE OF CORRECTION

PATENT NO. : 7,662,960 B2
APPLICATION NO. : 10/449822
DATED : February 16, 2010
INVENTOR(S) : Michael Kahn It is certified that error appears in the above-identified patent and that said Letters Patent is hereby corrected as shown below:

Column 89
Line 36, "D is $(CH_2)$-" should read -- D is $-(CH_2)-$ --.

Column 89
Line 58, "$C_1$ dialkylamino" should read -- $C_{1-4}$ dialkylamino --.

Column 90
Line 45, "the compound has the following structure: 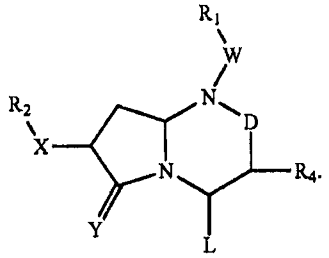 " should read -- the compound has the following structure: 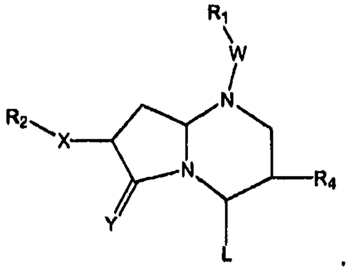 --.

Signed and Sealed this

Seventh Day of September, 2010

David J. Kappos
*Director of the United States Patent and Trademark Office*